US011382655B2

(12) United States Patent
Bouazza-Marouf et al.

(10) Patent No.: US 11,382,655 B2
(45) Date of Patent: Jul. 12, 2022

(54) NEEDLE GUIDES

(71) Applicant: LOUGHBOROUGH UNIVERSITY, Loughborough (GB)

(72) Inventors: Kaddour Bouazza-Marouf, Loughborough (GB); Atul Gaur, Loughborough (GB)

(73) Assignee: AGBM TECHNOLOGIES LTD, Leicester (GB)

( * ) Notice: Subject to any disclaimer, the term of this patent is extended or adjusted under 35 U.S.C. 154(b) by 317 days.

(21) Appl. No.: 16/071,411

(22) PCT Filed: Jan. 20, 2017

(86) PCT No.: PCT/EP2017/051257
§ 371 (c)(1),
(2) Date: Jul. 19, 2018

(87) PCT Pub. No.: WO2017/125594
PCT Pub. Date: Jul. 27, 2017

(65) Prior Publication Data
US 2019/0282262 A1 Sep. 19, 2019

(30) Foreign Application Priority Data

Jan. 20, 2016 (GB) .................................... 1601056
May 27, 2016 (GB) .................................... 1609414

(51) Int. Cl.
*A61B 17/34* (2006.01)
*A61B 8/00* (2006.01)
(Continued)

(52) U.S. Cl.
CPC ........ *A61B 17/3403* (2013.01); *A61B 8/0841* (2013.01); *A61B 8/4455* (2013.01);
(Continued)

(58) Field of Classification Search
CPC ............ A61B 17/3403; A61B 18/1477; A61B 2017/3407; A61B 2017/3413;
(Continued)

(56) References Cited

U.S. PATENT DOCUMENTS

| 6,216,029 B1 * | 4/2001 | Paltieli | A61B 8/0833 |
| | | | 600/427 |
| 7,223,238 B2 * | 5/2007 | Swanbom | A61B 5/6842 |
| | | | 600/437 |

(Continued)

FOREIGN PATENT DOCUMENTS

| WO | 2012/178109 A1 | 12/2012 |
| WO | 2014/133665 A1 | 9/2014 |
| WO | 20147/138918 A1 | 9/2014 |

OTHER PUBLICATIONS

International Search Report and Written Opinion dated Jul. 3, 2017 in PCT/EP2017/051257, all pages.

(Continued)

*Primary Examiner* — Yi-Shan Yang
*Assistant Examiner* — Alexei Bykhovski
(74) *Attorney, Agent, or Firm* — Kilpatrick Townsend & Stockton LLP

(57) ABSTRACT

A needle guide system for use with an ultrasound probe, the system comprising a surface marking guide and a needle guide. The surface marking guide includes an attachment portion for attaching the marking guide to an ultrasound probe, and a surface contact portion fixed to the attachment portion and including one or more features for identifying to a user where to mark a surface when the ultrasound probe is held against the surface. The needle guide includes a base to support the needle guide on the surface, one or more features on the base for alignment with marks made on the surface, and a needle support mounted on the base and having a needle channel through which a needle can extend, the (Continued)

needle channel having a known position and orientation relative to the base. We also describe a needle guide for use with an ultrasound probe to guide a needle along a predetermined path relative to the ultrasound probe.

20 Claims, 59 Drawing Sheets

(51) Int. Cl.
  *A61B 8/08* (2006.01)
  *A61B 90/11* (2016.01)
  *A61B 90/50* (2016.01)
  *A61B 90/00* (2016.01)
  *A61B 18/14* (2006.01)

(52) U.S. Cl.
  CPC .............. *A61B 90/11* (2016.02); *A61B 90/50* (2016.02); *A61B 18/1477* (2013.01); *A61B 2017/3407* (2013.01); *A61B 2017/3413* (2013.01); *A61B 2090/062* (2016.02); *A61B 2090/067* (2016.02); *A61B 2090/0811* (2016.02); *A61B 2090/378* (2016.02)

(58) Field of Classification Search
  CPC ........ A61B 2090/062; A61B 2090/067; A61B 2090/0811; A61B 2090/378; A61B 8/0841; A61B 8/4455; A61B 90/11; A61B 90/50

See application file for complete search history.

(56) References Cited

U.S. PATENT DOCUMENTS

| | | |
|---|---|---|
| 2003/0120154 A1 | 6/2003 | Sauer et al. |
| 2012/0069965 A1* | 3/2012 | Scheffer ................. A61B 90/11 378/162 |
| 2014/0005542 A1 | 2/2014 | Bizzell et al. |
| 2014/0276081 A1* | 9/2014 | Tegels .................... A61B 8/085 600/461 |
| 2016/0007956 A1* | 1/2016 | Mauldin, Jr. ........ A61B 8/0841 600/443 |

OTHER PUBLICATIONS

International Preliminary Report on Patentability dated Jul. 24, 2018 in PCT/EP2017/051257, all pages.

* cited by examiner

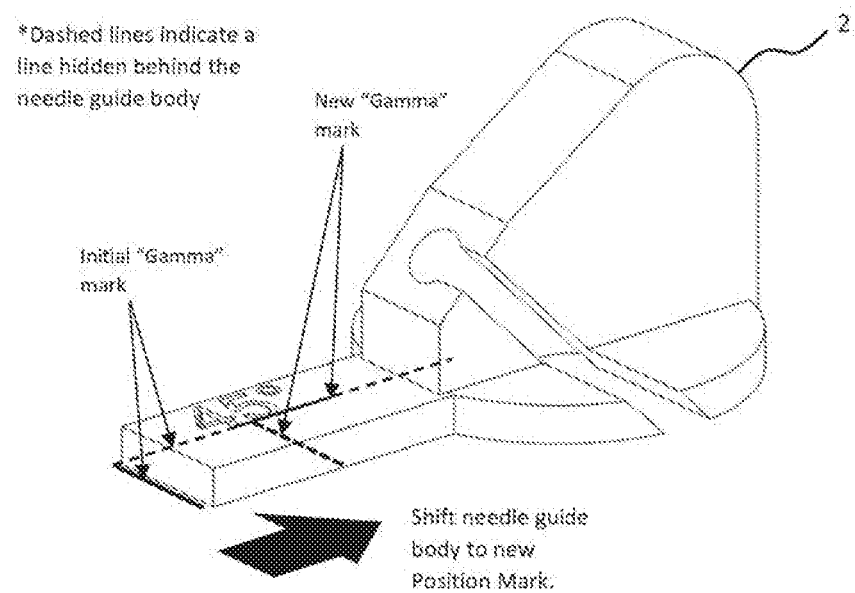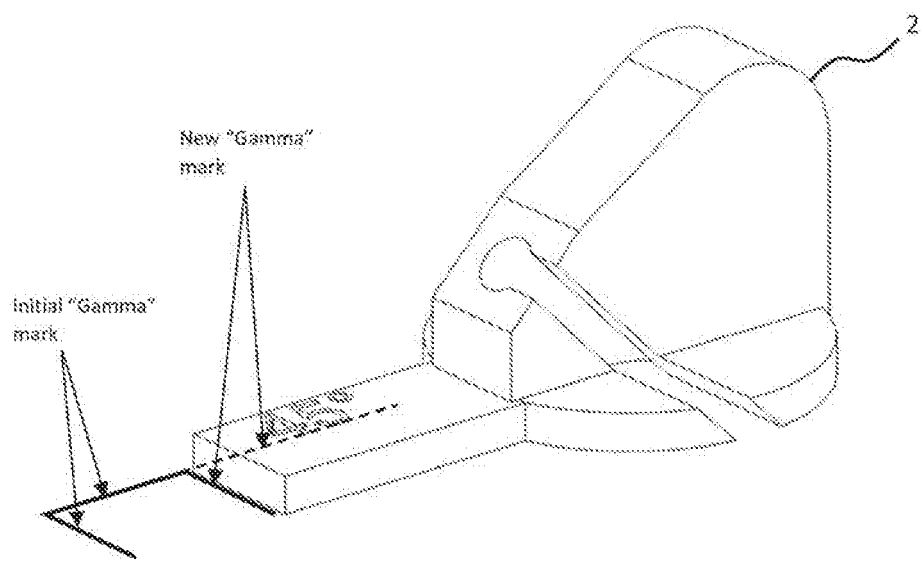
Figure 18

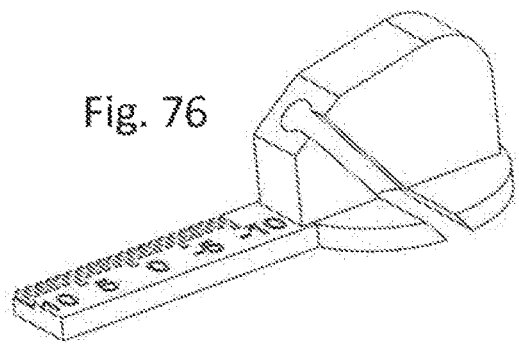
Fig. 76
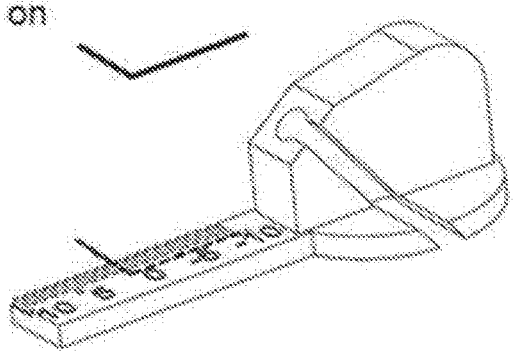
Fig. 77
Mark made on the body
Position of needle guide when no shift is necessary
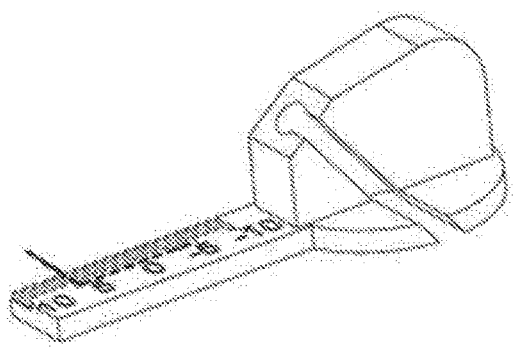
Needle guide shifted towards the US probe central axis
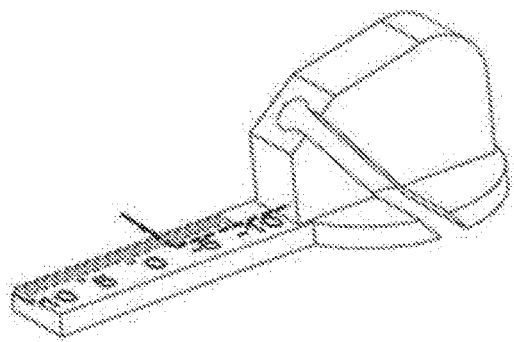
Needle guide shifted away from the US probe central axis

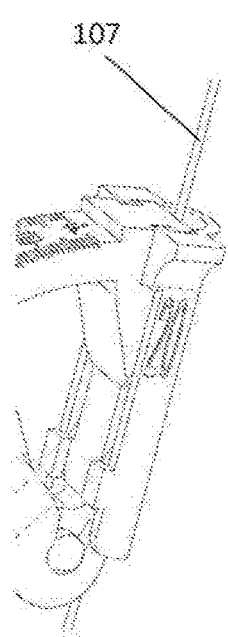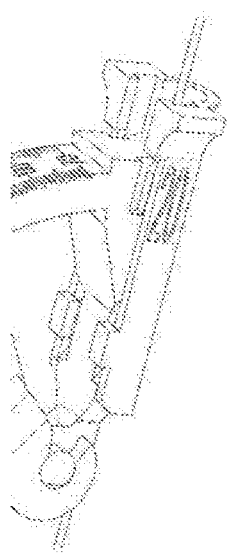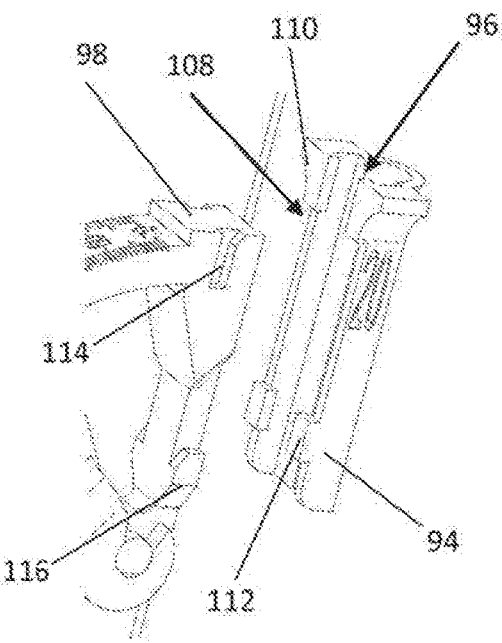
(a)  (b)  (c)
Fig. 101
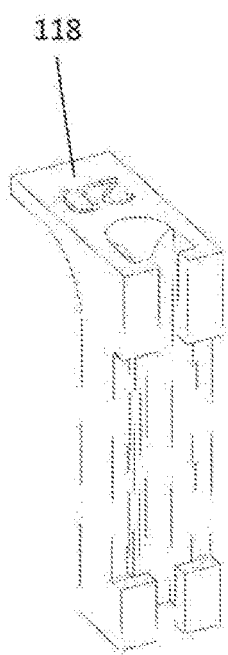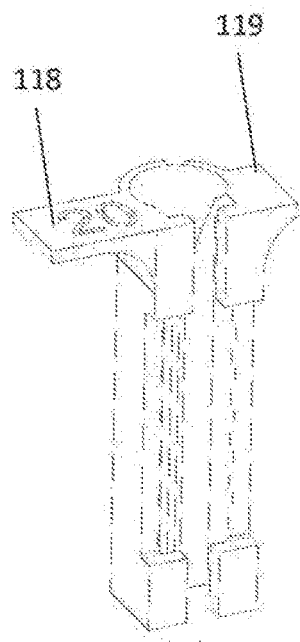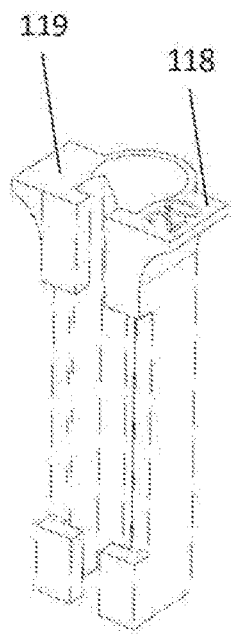
(a)  (b)  (c)
Fig. 102

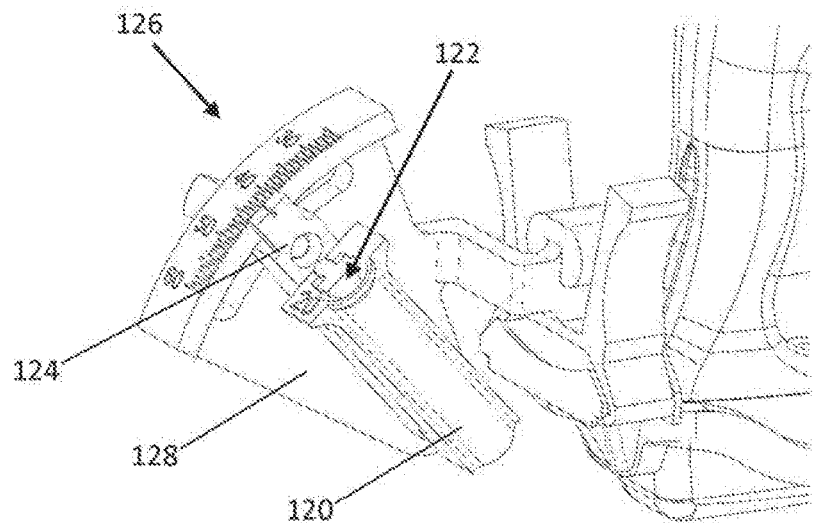
Fig. 103
Fig. 104
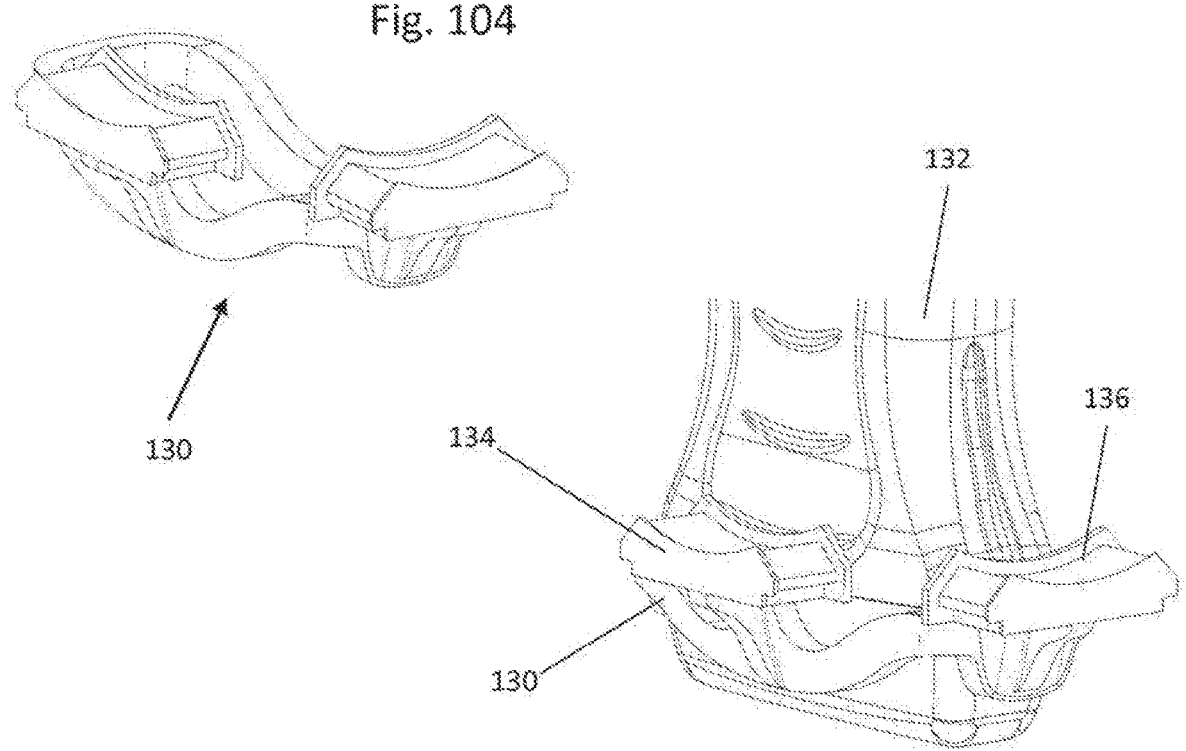
Fig. 105

(a)  (b)

NEEDLE GUIDES

CROSS-REFERENCE TO RELATED APPLICATIONS

This application is a U.S. National Stage of PCT Application No. PCT/EP2017/051257, filed Jan. 20, 2017, which claims priority to Foreign Application No. 1601056.3 GB, filed in the UK Intellectual Property Office on Jan. 20, 2016, and Foreign Application No. 1609414.6 GB, filed in the UK Intellectual Property Office on May 27, 2016, the disclosures of each of these applications is hereby incorporated by reference in its entirety for all purposes.

TECHNICAL FIELD

The present invention relates generally to needle guides to assist accurate placement of needles or instruments in objects, especially in the human or animal body, or in other medical or industrial use where ultrasound guidance is used to localise a target.

BACKGROUND

Accurate needle placement is vital for performing safe and efficient procedures such as biopsy, drug delivery, vascular access, regional anaesthetic blocks e.g. central and peripheral nerve blocks, and other such medical and non-medical procedures. Also, image guided minimally invasive surgical interventions require the accurate placement of instruments e.g. percutaneous tracheostomy, maternal-fetal interventions, radiofrequency ablation etc.

Ultrasound (US) scanning can identify and localise the target structure inside the body which can help carrying out an intervention more accurately e.g. needling procedure. Ultrasound guidance is used to improve successful insertion of needle and/or catheter; it provides relevant information e.g. the size of the target, best angle to insert the needle at, the direction of approach, and the depth of the target, along with the length of the needle needed to be inserted, etc. Pre-puncture ultrasound, or pre-intervention imaging guidance is usually used for two main procedures: vascular access, and neuraxial blocks. It can also be used for other procedures, including drainage of cavities, supra pubic catheterisation of the urinary bladder, localization of nerves or other important structures prior to surgery, percutaneous surgical interventions, foreign body/prosthesis localization, joint injections, etc.

When imaging a vessel or nerve as the target structure for a needling procedure, the US probe can either be held in the longitudinal orientation, or transverse orientation. The longitudinal orientation is gained when the long axis of the target structure lines up with the long axis of the footprint of the US probe; whereas the transverse orientation is gained by aligning the short axis of the target structure with the long axis of the footprint of the US probe. In this following, 'longitudinal' and 'transverse' will refer to positioning with respect to the target structure, and 'long axis' and 'short axis' will refer to positioning with respect to the US probe. 'Long axis' and 'short axis' will only be used when referring to marking guides in this document.

The use of US to assist needling procedures can take two different forms: real-time, and pre-puncture ultrasound scan.

When carrying out a real-time US procedure, the needle is advanced in conjunction with US imaging, meaning that the ultrasound guides the progress of the needle insertion or other intervention in real time.

Ultrasound beams are planar; both an in-plane technique (the longitudinal axis of the inserted needle would be in the same plane as the ultrasound beam) and an out-of-plane technique (the longitudinal axis of the inserted needle would be in a plane perpendicular to the ultrasound beam) are commonly used techniques in real-time ultrasound guided needle interventions. FIGS. 91(a) and 91(b) show pictorial representations of out-of-plane and in-plane techniques respectively. Both in-plane and out-of-plane injection techniques have associated advantages and disadvantages, and thus preference as to which technique to use is left to the clinical scenario and discretion of the clinician.

Oblique needle placement is also a possibility. This is not a common procedure; it is performed by expert users to reach a difficult target.

It is not an easy task to insert the needle freehand at a required angle and to the required depth using real-time ultrasound guidance. These procedures require skills obtained through training and experience. Consequently, a needle guidance system may be used by clinicians to help guide a needle into a patient in a more accurate and precise manner with better needle visualisation, reducing the time taken to place the needle.

Examples of needle guidance systems are described in: U.S. Pat. No. 4,058,114; US 2005/0113816; U.S. Pat. No. 8,073,529; WO 2006/060657; U.S. Pat. Nos. 8,449,531; 5,941,889 and US 2010/0160787.

In pre-puncture ultrasound procedures, the clinician/operator/interventionist (clinician) first carries out a scout US scan. The pre-puncture ultrasound examination is performed to gather information such as (a) location the target, its size, depth etc. (b) assessment of the suitability of the target (c) selection of a safe needle entry point and (d) decision on the plane of needling. Once this is done, the clinician marks the skin before proceeding to insert the needle free-hand using aseptic technique, without real-time guidance of US. When marking the skin, the clinician can either mark in the long axis or the short axis of the US probe.

The choice of a pre-puncture ultrasound technique over a real-time one can be due to many factors, including: the size of the target structure, availability of space for performing the procedure, the entry point of the needle with respect to the transducer placement, equipment constraints, clinical situation, skill of the clinician, the clinician's preferred method and local clinical practice, etc.

The pre-puncture scan can enhance the safety and accuracy of interventions when compared to landmark guided techniques in many situations; e.g. in large build ups of fluid or air, or when the target is large, the pre-puncture technique may be an alternative. This is because a large collection of air or fluid can be confidently drained using a pre-puncture ultrasound technique. Procedures that may be performed using a pre-puncture ultrasound technique include: pleurocentesis, pericardiocentesis, and abscess drainage.

The pre-puncture ultrasound technique may be suitable when there are constraints related to space, such as using adult size ultrasound probes in very small patients or where there is a limited area to scan and perform a real-time ultrasound guided procedure. During central venous catheter (CVC) insertion landmark guided technique, it is possible to miss the internal jugular vein (IJV) and instead puncture the internal carotid artery (ICA), which normally runs medially to it, this can cause potentially life-threatening complications. The use of imaging guidance is expected to reduce/alleviate such complication rate. Also, there can be spatial constraints e.g. in the forearm where the curvature or body shape can make a real-time ultrasound guided procedure difficult, in which case a pre-puncture ultrasound approach would offer some help, and be beneficial to the patient when compared to landmark guided techniques.

In spinal interventions, such as epidural drug delivery, the pre-puncture ultrasound method is recommended to assess the depth and direction of the epidural space or ligamentum flavum-dura complex prior to needling procedure. Also, the realtime ultrasound guided procedure is not very convenient and safe to perform due to technical difficulties including the fact that the path of the needle follows the central line of the transducer. The pre-puncture ultrasound needle guide, as described below, may be of great help in this situation.

When carrying out an invasive procedure like needling, it is important that aseptic technique is used. Normally the US probe is placed inside a sterile cover for use in real-time US procedures, and a sterile US gel should be used. If the clinician has no access to these resources, they can still carry out a pre-puncture ultrasound procedure if they wish to use some US assistance. Also, when delivering a neuraxial block, the use of real-time US using ultrasound gel is of concern as the "neurotoxicity of US gel is unclear" [1].

It has been documented that multiple attempts to deliver spinal or epidural anaesthesia are associated with a greater incidence of complications such as post dural-puncture headache, paraesthesia, haematoma, and spinal injury, and so reducing the number of attempts will save time, reduce complications and enhance patient care and satisfaction besides improving work flow and operator comfort. The use of pre-puncture ultrasound in epidural anaesthesia is gaining popularity and has been documented in case studies and case series, as well as in randomised control trials by Grau et al [2]. Also, Chin et al [3] note that the "first-attempt success rate was twice as high in group US than in group LM" whereby 'group US' used pre-puncture US guided technique, and 'group LM' used landmark guided technique. In addition, the number of needle insertions and number of needle passes were reduced by approximately half in group US compared to group LM. So the use of US guidance is clearly beneficial to patient safety and wellbeing.

U.S. Pat. No. 4,733,661 describes a guidance device for CT guided drainage and biopsy procedures. U.S. Pat. No. 5,100,387 describes a disposable universal needle guide apparatus (for amniocentesis). U.S. Pat. No. 7,223,238 describes a method and device for marking skin during an ultrasound examination. U.S. Pat. No. 8,123,689 describes a device for locating and marking contact point between skin of a patient and centre of ultrasound transducer. U.S. Pat. No. 6,200,274 describes a removable needle rule for ruling the depth of penetration of a needle.

SUMMARY OF THE INVENTION

A general aim of the present invention is to improve the success rate of real-time and pre-puncture ultrasound guidance.

Especially for pre-puncture ultrasound guidance, a general aim is to reduce the number of passes needed by providing a "needle guide" that can be accurately positioned, subsequent to a US scan, to guide a needle into a patient (or other object) from a desired needle entry/puncture point and at a desired angle and length to reach a target. The Needle guide system in accordance with embodiments of the present invention will be of great help to a wide range of clinicians interventionists, from newly trained to well experienced, when using pre-puncture ultrasound guided procedures, as it provides alternatives to, and also removes some of the technical difficulties of real-time US guidance, whilst having the potential of maintaining the accuracy and precision needed to minimise patient discomfort and improve the outcome.

In a first aspect, the invention provides a needle guide system for use with an ultrasound probe, the system comprising:
(i) a surface marking guide; and
(ii) a needle guide (to guide a needle or a surgical instrument, etc.);
the surface marking guide including:
(a) an attachment portion for attaching the marking guide to an ultrasound probe, and
(b) a surface contact portion fixed to the attachment portion and including one or more features for identifying to a user where to mark a surface when the ultrasound probe is held against the surface while pre-scanning; and
the needle guide including:
(a) a base to support the needle guide on the surface;
(b) one or more features on the base for alignment with marks made on the surface; and
(c) a needle support mounted on the base and having a needle channel through which a needle can extend, the needle channel having a known position and orientation relative to the base.

It should be noted that the term "needle guide" is used herein to refer to a structure that can serve to guide a needle or other similar items, including probes, micro-blades, surgical instruments and other instruments for performing interventions, including interventions other than vascular access and nerve block. The terms "needle guide", "needle" and other terms employing the word "needle" used herein should be construed accordingly.

In some embodiments, the one or more features on the base of the needle guide are intended for alignment with a mark or marks made on the surface using the surface marking guide.

Another variable that requires consideration is the orientation in which the US probe is held with regards to the plane of the direction of travel of the needle. When marking in the long axis of the footprint of the probe, the mark would be made on the skin further away from the midline of the image and so the angle of entry must be smaller in order for the needle to enter the target at the location that was scanned. The opposite is true whilst marking in the short axis, as the mark will be closer, so the angle of entry needs to be greater. However, we can modify this angle of insertion by moving the guide itself either closer to, or further from, the centre point of the US probe.

Thus, in other embodiments, the system further comprises a second marking guide that has a first set of one or more features for alignment with marks made using the surface marking guide and a second set of one or more features (e.g. a ruled edge with length markings, or marks transfer adaptor) for identifying to a user where to mark a surface to make secondary marking offset from the marking made using the surface marking guide. In this case, the one or more features on the base of the needle guide are then intended for alignment with a mark or marks made on the surface using the second marking guide. This offsetting of the markings may be desirable in some case, for example to allow a different angle of insertion and to reach other targets within the US image. This offsetting of the markings may also be desirable to allow needle insertion at any position on the surface in between the long axis and short axis of the US probe footprint.

The second marking guide may be integral with the surface marking guide or separate from it. It may, for example, be a simple rule. Alternatively, it could be a slidable extension strip that can be extended from the surface marking guide. Another possibility is that the second marking guide is an optical device that projects guide features onto the surface.

The difference between marking in the long axis and short axis can also be accommodated by differing the distance from the scanned plane to the marking guide, making the long axis marking guide closer, the short axis marking guide further away, or both, as described further below.

In some embodiments, the one or more features of the surface contact portion of the surface marking guide define a position relative to a centre line of the ultrasound probe and an orientation of the probe.

The features may take any of a number of appropriate forms that are able to define a position and an orientation. Examples include, but are not limited to one or any combination of two or more of:

a pair of edges at a fixed angle relative to one another;
an opening defining a point and an edge;
an edge with defined end points;
a corner;
a slot; and
two openings defining two points.

In some embodiments, the marking guide can be a laser/light guide attached to the probe. Such optical device project a feature (similar to above) on the skin, which is used to mark the appropriate feature on the surface of the skin using a marker.

In some embodiments, the features on the base of the needle guide are the same as the features on the surface contact portion of the surface marking guide.

In some embodiments the base of the needle guide and/or the surface contact portion of the surface marking guide may be 'sticky' (e.g. have an adhesive layer or substance applied to them) in order to help provide a stable placement once positioned on the skin and/or to hold the component in place even when not being held by hand. This may be particularly beneficial for the base of the needle guide, for helping to keep the needle guide stable during needle insertion. Similarly, any other skin contacting elements of the system may, if desired, have an adhesive layer or substance applied to them to help provide stable placement on the skin and/or to hold the component in place even when not being held by hand.

The angle of needle insertion and length to which the needle must be inserted can be determined, for a given needle insertion point, from the pre-puncture ultrasound. The desired angle will typically differ depending on the procedure and the clinician's preference. For example, with vascular access, the entry angle is important to allow for successful cannulation with reduced or no complications, such as a catheter or guide-wire kink. It would therefore be advisable for the pre-puncture ultrasound needle guide assistance to use angles such as 25°, 35°, and 45° or thereabouts. For nerve blocks, on the other hand, the angle may be less important unless a catheter is inserted along the long axis of nerve to provide continuous block, hence target depth, adjacent structures and spatial constraints become more important parameters. Thus, for pre-puncture ultrasound needle guide assistance, a wide range of angles may be used, including angles such as 65° and 85°. Taking into account both vascular access and nerve block like procedures, this gives a typical range of angles of 25°, 35°, 45°, 65°, and 85° or thereabouts.

To cater for different needle insertion angles, in some embodiments the needle guide system includes a plurality of needle guides in which the angle of the needle channels relative to the bases of the needle guides are different from one another.

In other embodiments, a single needle guide may cater for multiple needle insertion angles. More specifically, the needle guide can be configured so that a needle channel can be provided at a plurality of different angles relative to the base of the needle guide.

For example, a needle guide may be provided in which the needle support can be selectively mounted at any one of a plurality of discrete needle support mounting positions on the base, the angle of the needle channel being different at each mounting position.

Alternatively, the needle support may be pivotably mounted on the base of the needle guide, whereby the angle of the needle channel relative to the base can be varied by pivoting the needle support relative to the base. Where the angle is variable, markings can be provided on the needle guide to indicate the appropriate angular position of the needle channel for a given desired needle insertion angle and/or target depth. This can cater for insertion of the needle at any chosen angle or to reach any chosen depth along the centre line of the US probe.

It may sometimes be desirable to insert one, two or more needles close to each other, and parallel to each other or at other angular orientations, during the same pre-puncture ultrasound guided procedure. Therefore, the needle guide may have one, two or more needle channels, which are parallel to each other or at other angular configurations.

To cater for different gauge needles, the system may be provided with a plurality of needle supports, each needle support having a needle channel adapted to receive a needle of a different gauge to the other needle supports. In some embodiments, the needle supports (e.g. a needle gauge insert) can, for example, be formed in two parts that can be separated and placed around the needle, or can be manufactured using a flexible material with a vertical split, to allow for non-uniform needles or surgical instrument, such as the Tuohy needle, to be used.

In some embodiments, the surface marking guide and needle guide are configured so that when the needle is in the needle channel with the needle guide located by the marks on the surface, the needle is aligned with the US probe axis, the probe axis being the axis that was through the centre line of the US probe when the probe was positioned on the surface and the surface was marked using the surface marking guide.

In some embodiments, the surface contact portion of the surface marking guide is fixed to the attachment portion via a curved arm, a centre of curvature of the curved arm being located at a mid-point of the US probe footprint when the surface marking guide is mounted on the probe. The length of the curved arm is preferably adjustable to change the angle of the surface contact portion relative to the attachment portion. In such embodiments, the needle support of the needle guide is also attached to the base of the needle guide via a curved arm that has the same radius of curvature as the curved arm connecting the surface contact portion of the surface marking guide to the attachment portion of the surface marking guide. This can enable the needle entry point on the skin to be at the centre of the US probe used in the pre-scan. In this example, the surface contact portion of the surface marking guide and the base of the needle guide may be identical or the same component.

As noted above, to accurately place the tip of a needle at a target, as well as inserting the needle at a defined angle, it is also important to insert the needle to a specific depth. It is a combination of the needle entry point, needle angle and insertion length that determine the final position of the needle tip. In some embodiments, the needle guide system also includes a needle insertion length rule that can be used to mark a needle with a desired needle insertion length.

In some embodiments, the needle itself is also supplied as part of the system. That is, the system can be a kit of parts including the surface marking guide, the needle guide, an introducer needle, and the needle, in some cases including a plurality of needle guides for different angles and/or target depths, and/or a plurality of needle supports for different gauge needles. Preferably, the needle guides have markings to identify the needle angle and/or depth they are to be used for.

In a second aspect, the invention provides a method of positioning a needle guide on a surface, the method comprising:
positioning an ultrasound probe on the surface, the ultrasound probe having a surface marking guide attached thereto;
marking the surface on or adjacent the marking guide with one or more primary marks;
removing the ultrasound probe; and
aligning a base of the needle guide with the one or more primary marks to position the needle guide on the surface.

In some embodiments, the surface marking guide comprises an optical guide attachment on the probe and features projected onto the surface by this optical guide attachment. In this case the primary marks are made on the surface on or adjacent to the projected features. In other embodiments, the step of marking the surface may comprise transferring a marking element (e.g. a sticker) from the marking guide to the surface.

In some embodiments, the method uses a second marking guide to make one or more secondary marks on the surface at a predetermined position relative to said one or more primary marks. In this case, the step of aligning the base comprises aligning the base of the needle guide with one or more of the primary and/or secondary marks.

In some embodiments, a chart or software associated with the US probe is used to indicate the required needle insertion angle, needle insertion length and other details to reach a target at a specific depth on the centre line of the US probe. The chart or software may indicate the required needle insertion angle and needle insertion length taking account of needle insertion points at different off-sets from the US probe centre line. The chart or software associated with the US probe may provide the appropriate needle guide to be used; this can be a needle guide with a specific needle insertion angle, or a needle guide with appropriate configuration to reach any target position on the US image.

In some embodiments the needle guide is removed once the needle has been inserted. This may be achieved using a needle guide in which the needle support can be separated from the needle guide base, for example; or by using a needle guide in which the needle channel is open on one side so that it can be removed laterally from the needle, with the needle passing through the open side.

A needle guide system according to the first aspect above can be used for the method of the second aspect.

In a third aspect, the invention provides a needle guide for use with an ultrasound probe (also known as ultrasound transducer) to guide a needle or instrument (in real-time, i.e. whilst the probe is in position on a patient) along a predetermined path relative to the ultrasound probe, the needle guide comprising:
a needle guide body configured to be coupled to the ultrasound probe; and
a needle support having a needle channel therein for receiving and guiding the needle and configured for releasable attachment to the needle guide body whilst the needle is received in the needle channel.

Embodiments of this aspect of the invention have the advantage that it becomes possible to remove the needle support completely from the needle during a procedure whilst the needle is in situ in the patient. In some embodiments it is also possible to remove the entire needle guide from the needle and the ultrasound probe whilst maintaining the needle in situ and the ultrasound probe in position.

In some embodiments, in order to attach the needle support to the needle guide body, these two parts may comprise cooperating engagement features that can be releasably engaged with one another. For example, a protuberance may be formed on one of the components with a socket into which the protuberance can be received on the other component. The protuberance may be formed on the needle guide body and the socket on the needle support or vice versa.

In some embodiments using a socket/protuberance type engagement between the needle support and the needle guide body the socket is defined between the inner faces of two opposed arms that can be moved apart to receive the protuberance therebetween and closed around the protuberance to secure it in the socket.

In some embodiments the cooperating engagement features are configured so that they can be disengaged from one another by moving the needle support relative to the needle guide body in a direction generally in line with the needle axis when the needle is engaged in the needle channel. For example, the needle support may include a cylindrical barrel within which the needle channel is formed along the axis of the barrel and the needle guide body may have a cylindrical socket within which the barrel of the needle support can be received. Alternatively, the needle support may include one or more tabs that can be engaged with and disengaged from complementary slots in the needle guide body by moving the needle support relative to the needle guide body generally in line with the needle axis.

In some embodiments, the needle channel within the needle support is open on the side that faces the needle guide body. In this case, the open side of the channel can be closed off by the needle guide body when the needle support and needle guide body are attached to one another, to securely hold the needle in the desired position. However, by having an open sided channel in the needle support it becomes possible to easily release the needle once the needle support is disengaged from the needle guide body.

In some embodiments, the needle guide is configured such that, with a needle in place in the needle channel and inserted into a patient, when the needle support is disengaged from the needle guide body, the needle becomes disengaged from the needle guide body and can be manipulated freely relative to the needle guide body. The needle can be manipulated with the needle support still in place around the needle. Alternatively, the needle support may be removed from the needle prior to manipulation of the needle.

In some embodiments the needle support is also configured to be removable laterally from the needle (i.e. without having to slide the needle support off the end of the needle) when the needle support is disengaged from the needle guide body. For example, the needle support may comprise a pair of opposed arms with the needle channel defined between opposed faces of the arms. In this way, the arms may be moved apart from one another to open the channel and allow the needle to be released laterally from the channel.

In some embodiments in which the needle support comprises two opposed arms, opposed faces of the arms may define a socket in the needle support for engaging a protuberance on the needle guide body and may also define the needle channel. In such arrangements, when the arms are moved apart the needle support can be detached from the needle guide body and the needle at the same time.

In embodiments in which the needle support comprises two opposed arms as proposed above, the arms may be biased towards one another, for example by a spring.

In order to facilitate opening of the arms of the needle support for release from the needle guide body and/or for opening the needle channel, the arms may be pivoted to one another. Grip portions of the arms may be provided to the opposite side of the pivot from the socket and/or needle channel to facilitate opening of the arms (e.g. against a biasing force) to move the opposed faces of the arms apart from one another.

In some embodiments, the needle support comprises a needle support body and a needle channel insert that is mountable on and detachable from the needle support body, the needle channel being formed in the needle channel insert. In this way, it is possible to accommodate different needle sizes simply by selecting a needle channel insert with an appropriately sized needle channel.

In embodiments in which the needle support comprises a pair of opposed arms, the needle channel insert may be formed in two parts, each part mountable on a respective one of the arms so that when the arms are closed together the two parts of the needle channel insert are held together to form the needle channel therebetween. For convenience, in some embodiments the two parts of the needle channel insert are held together prior to use with a connector element (e.g. a weak link element) that can be broken or removed once the two parts are in place.

In some other embodiments, rather than the needle channel being formed between opposed faces of the two arms of the needle support or within a needle channel insert, the needle channel may be provided between an inside surface of one of the arms and a needle channel insert mounted on that arm. The needle channel insert may be mounted on the arm by a sliding connection or a pivot connection, for example. This configuration has the advantage that it is potentially possible to release the needle from the needle channel independently of releasing the needle support from the needle guide body. It is possible to adapt the needle support to different needle sizes by selecting a needle channel insert with an appropriately sized needle channel.

In some embodiments, the angle of the needle channel is adjustable relative to the needle guide body, whereby in use any of a number of different angles of attack for a needle relative to the ultrasound probe can be selected. Whilst the needle guide may be configured to dictate a plurality of discrete angles for the needle channel, in some embodiments the angle of the needle guide is adjustable in a continuous range between two end points.

In some embodiments, in which the needle support is releasably attached to the needle guide body by cooperating engagement features, the cooperating engagement feature on the needle guide body may be pivotable to change the angle of this feature relative to the needle guide body, thereby to change the angle of the needle support, and the needle channel therein, relative to the needle guide body. For example, the needle guide body may comprise a main body part and a pivot arm pivotally attached to the main body part, with the cooperating engagement feature being provided on the pivot arm. In this way, pivoting the pivot arm relative to the main body part adjusts the angle of the engagement feature and hence ultimately the angle of attack of the needle in use.

In some embodiments, in order that the needle angle can be accurately set, the needle guide comprises scale markings and a marker that moves along the scale markings with the changing angle of the needle channel to indicate a current angle of the needle channel relative to the needle guide body (and hence relative to the axis of the ultrasound probe in use). For example, in the case where the needle guide body comprises a main body part and a pivot arm, the scale markings may be formed on the main body part and a marker on the pivot arm can indicate the angle (or the pivot arm itself may serve as the marker).

The scale markings for adjustment of the needle guide can be either:

a. Angles—The angular position for in-plane or out-of-plane procedures can be obtained from a chart (e.g. a paper chart or an electronic chart or equivalent displayed on a device such as a tablet or a smartphone, for example within an app installed on the device) or calculated by the ultrasound system and, for example, displayed automatically, superimposed on the real time ultrasound image; or b. Depths of the target taken along the centreline of the ultrasound probe—taking this approach the depth measurement along the ultrasound probe axis is used directly to adjust the angular position of the guide. However, two scales would typically need to be displayed, one for in-plane procedures and one for out-of-plane procedures because the distance between the needle support and the centre line of the probe may vary (normally shorter) for out-of-plane procedures. In some embodiments, it is possible to use the same scale for in-plane and out-of-plane procedures by setting the distance from the needle guide attachment to the probe central axis to be the same for both procedures.

Whilst the needle guide of the third aspect may be configured for direct attachment to the ultrasound probe, it is more preferred that the attachment is via a bracket. In this way, different brackets may be configured for attachment to different models of ultrasound probe so that the same needle guide may be used with multiple probe models simply by selecting the appropriate bracket.

Accordingly, in a fourth aspect, the invention provides a needle guide system, comprising a needle guide according to the first aspect above and a bracket for mounting the needle guide to the ultrasound probe.

In some embodiments the bracket is adapted to engage with the ultrasound probe in a specific fixed orientation and position relative to the probe and the bracket comprises at least one needle guide mount on which the needle guide can be mounted at a specific position on the bracket and at a specific orientation relative to the bracket. In this way, the position and angle of the needle channel in the needle guide relative to the ultrasound probe can be accurately repeated every time.

The bracket may be a single-piece component that can be mounted on the ultrasound probe (e.g. by pushing onto the bottom of the probe, placing over the top of the probe or pushing on from a side of the probe. Alternatively, the bracket may comprise two or more parts that can be mounted on the probe and held in position, in a fixed orientation, using an appropriate locking mechanism.

In some cases, it may be desirable to introduce the needle from different positions around the ultrasound probe, for example to gain the advantages of oblique needle placement. Accordingly, in some embodiments the bracket comprises a plurality of needle guide mounts for mounting the needle guide on the bracket at a corresponding plurality of specific positions. The bracket may be configured, for example, to extend at least partially around the ultrasound probe in a plane perpendicular to the plane of the ultrasound beam produced by the probe, with the plurality of needle guide mounts spaced along the bracket. The bracket may, for example, have mounts spaced apart at 45 degree intervals around the bracket, 30 degree intervals around the bracket or some other regular or irregular interval. Additionally or alternatively, the bracket may have a plurality of guide mounts side-by-side along the bracket, all oriented in the same direction.

In a further alternative embodiment, the bracket may include a needle guide mount that takes the form of a continuous rail extending around a segment of (or the whole of) the bracket, so that the needle guide can be mounted at any location along the rail. The rail may, for example, have a semi-circular/semi elliptic or circular/elliptic form to wrap around two or more sides of the ultrasound probe when the bracket is mounted on the ultrasound probe. The rail (or a portion of the bracket adjacent the rail) may have markings to indicate positions around the perimeter of the ultrasound probe to help ensure accurate placement of the needle guide and hence the needle itself.

The position of the bracket around the ultrasound probe can be changed manually.

In some embodiments, the bracket further comprises a needle support mount on which the needle support can be mounted when it is detached from the needle guide body.

In a fifth aspect, the invention provides a kit of parts for a needle guide or a needle guide system, the kit of parts comprising:
- a needle guide according to the first aspect above or needle guide system according to the second aspect above for use with an ultrasound probe to guide a needle along a predetermined path relative to the ultrasound probe; and
- a needle insertion length pointer configured to be mounted on the needle at a chosen position to indicate a desired depth of insertion for the needle.

In some embodiments, the kit of parts according to this aspect includes a plurality of needle depth pointers adapted for use with different gauge needles.

In some embodiments, the needle itself and an introducer needle are also supplied as part of the system. That is, the system can be a kit of parts including the needle guide, (optionally) an introducer needle, and the needle itself. In some cases the kit may include a plurality of introducer needles of different lengths and gauges, and/or a plurality of needle supports for different gauge needles.

An example of a needle rule that can be used in conjunction with a depth guide for setting an insertion length on the needle is described in U.S. Pat. No. 6,200,274.

Where practicable, features described above in the context of pre-puncture embodiments can also be used in conjunction with real-time embodiments and vice versa.

BRIEF DESCRIPTION OF THE DRAWINGS

FIG. 15(*b*) is a sectioned view of an ultrasound probe positioned on a skin surface and a section view showing a target and trajectory lines of a Centre Line Fixed Depth needle guide system and illustrates a shift of needle entry point required for the system shown in FIG. 15(*a*).

FIG. 19 illustrates the positioning of a needle guide at a shifted mark.

FIG. 37 shows an exploded view of the surface marking guide and ultrasound probe of FIG. 36a.

FIG. 57b illustrates two needle inserts which may be utilised in the Needle Insertion Guidance System of FIGS. 56 and 57a.

FIG. 58b is a different perspective view of the Needle Insertion Guidance System of FIG. 58a.

FIG. 58c is a side view of the Needle Insertion Guidance System of FIG. 58a.

FIG. 59b illustrates the insertion of a needle into the needle insert of FIG. 59a.

FIG. 76 illustrates an alternative needle guide incorporating a rule.

FIG. 77 illustrates the manner in which the needle guide shown in FIG. 76 can be used to move the point of needle insertion relative to a mark on the patient's skin.

FIG. 100 shows the needle guide system of FIG. 98 mounted on an ultrasound probe in an out-of-plane configuration;

Figure 95:
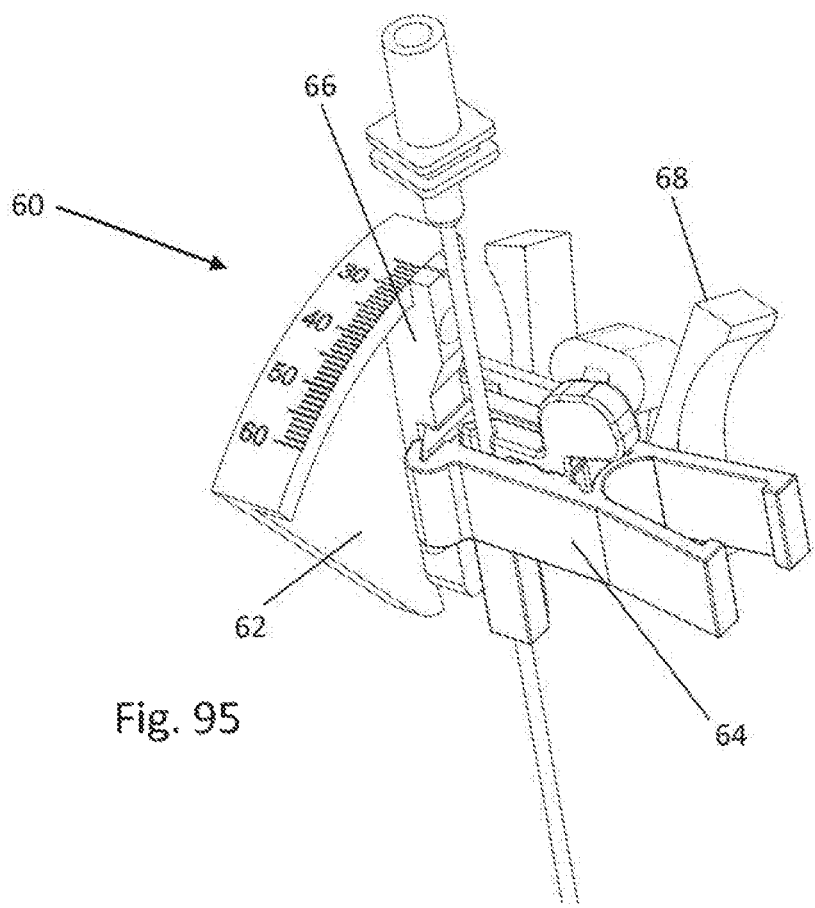
FIG. 95 shows a needle guide in accordance with another embodiment of the invention.
Figure 96:
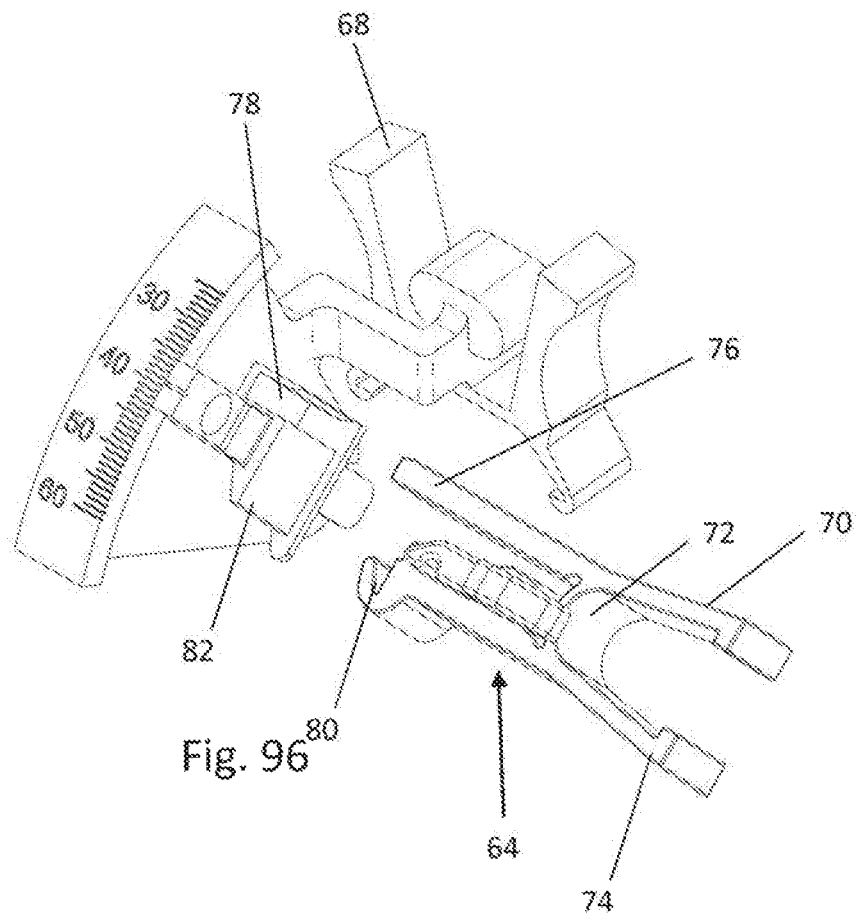
FIG. 96 shows an exploded view of the needle guide seen in FIG. 95 (with the needle omitted)
Figure 97:
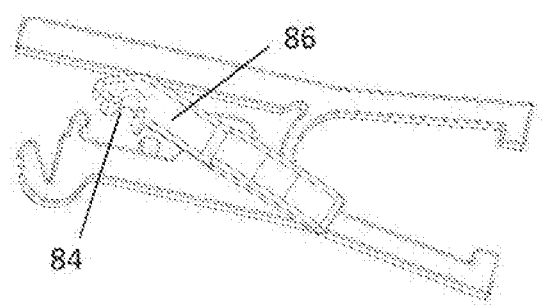
FIG. 97 shows, on an enlarged scale, the needle support clip of the needle guide seen in FIG. 95.
Figure 98:
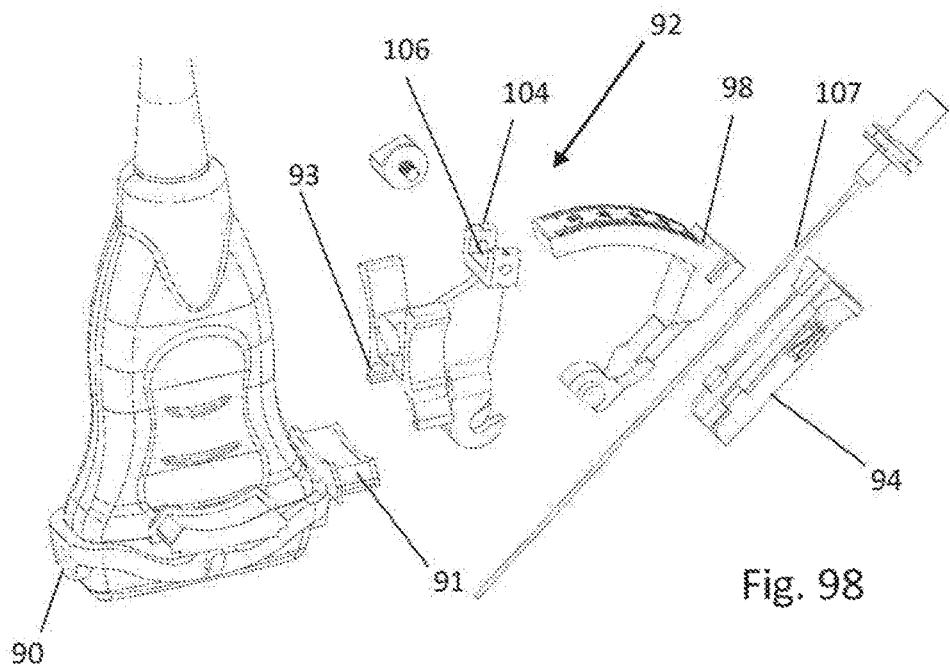
FIG. 98 shows an exploded view of another needle guide system in accordance with an embodiment of the invention.
Figure 106:
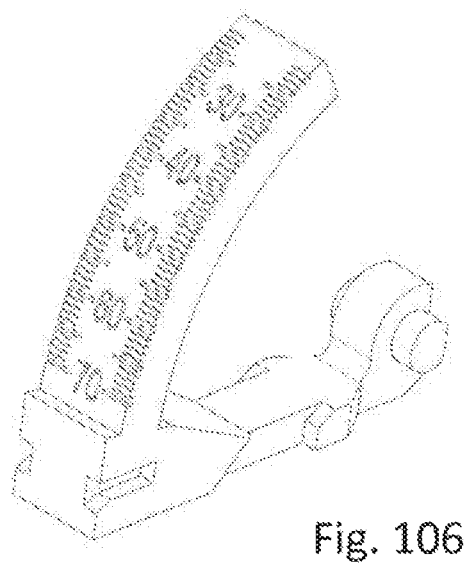
Figure 107:
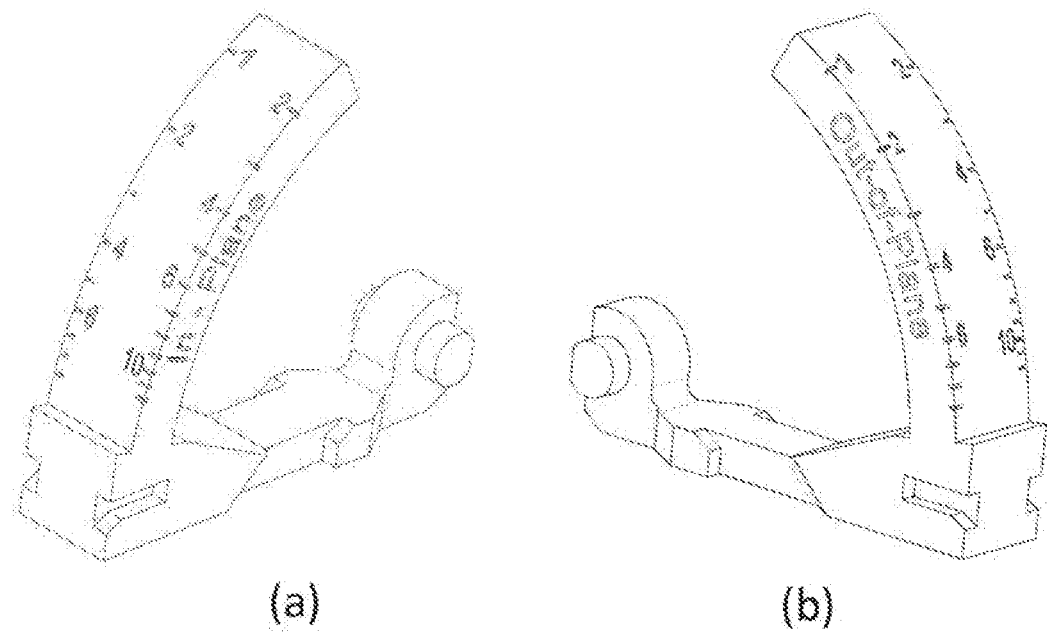
Figure 108:
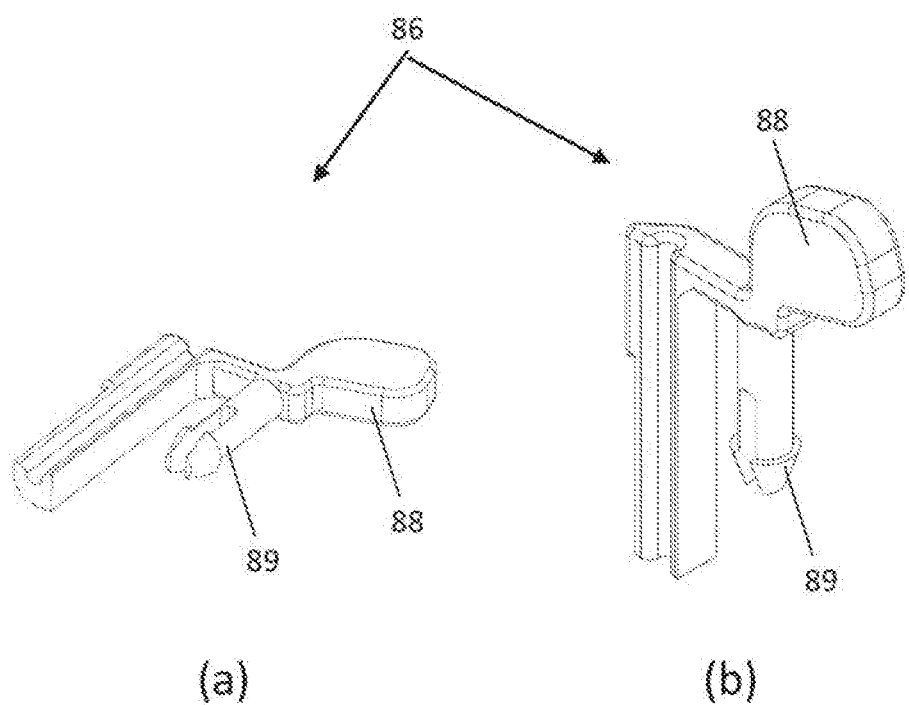

FIGS. 101 (a) to (c) illustrates the manner in which the needle support of the system of FIG. 98 is detached from the needle guide body;

FIGS. 102(a) to (c) show three variants of a needle support suitable for use with the needle guide systems in accordance with embodiments of the invention, for example as shown in FIG. 103;

FIG. 103 shows a needle guide system in accordance with yet another embodiment of the invention;

FIG. 104 shows the bracket of the needle guide system of FIG. 103 (and FIG. 95, FIG. 99 and FIG. 100) used to mount the needle guide to an ultrasound probe;

FIG. 105 shows the bracket of FIG. 104 mounted on an ultrasound probe;

FIG. 106 shows one form of angle measuring scale that can be used with embodiments of the present invention;

FIGS. 107(*a*) and (*b*) show another form of measuring scales that can be used with embodiments of the present invention (the scales represent the depths of the target taken along the centreline of the ultrasound probe, one scale for in-plane procedures and one for out-of-plane procedures); and FIGS. 108(*a*) and (*b*) show an example of a needle channel insert for use with the embodiment of FIGS. 95 to 97.

Figure 109:
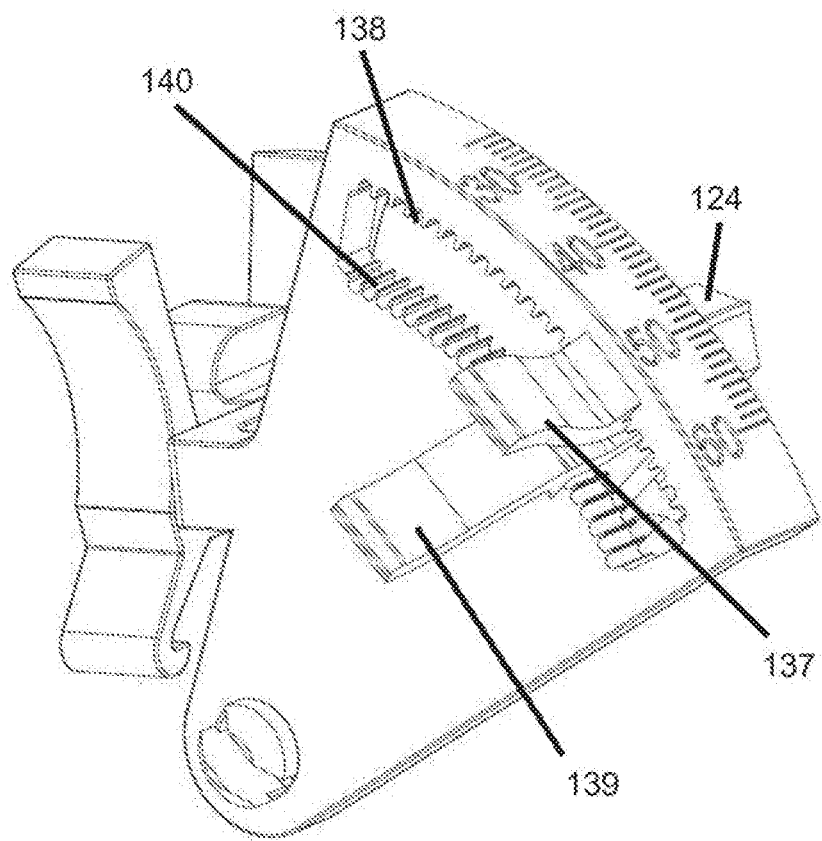

FIG. 109 illustrates an alternate locking mechanism for adjusting and locking the angle of the needle guide.

Figure 110:
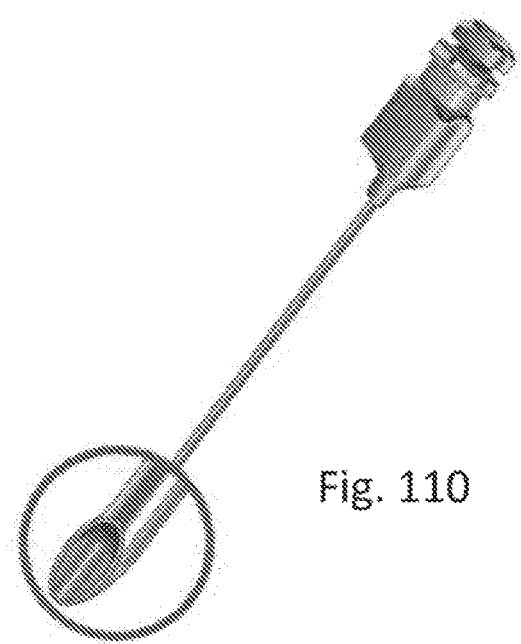

FIG. 110 shows a Tuohy needle.

DETAILED DESCRIPTION

The invention will now be further described with reference to the following non-limiting Figures and Examples. Other embodiments of the invention will occur to those skilled in the art in the light of these. Embodiments of pre-puncture needle guides are discussed first, followed by embodiments of real-time needle guides.

Pre-Puncture Needle Guides

Two types of pre-puncture guides have been developed and examples of each type are described below: one system for universal pre-puncture ultrasound needle guidance, referred to as "The Universal Guide", and one specific for certain procedures, such as epidural procedures, where the US probe placement may hinder the needle insertion point and needle trajectory in real time guidance, for example, when there is a need to insert the needle at the centre of the US probe footprint at any angle; this is referred to as "The Epidural System" for ease of reference, although it has wider applicability. A more generic name can be "inter-probe base variable pose guide system".

The pre-puncture ultrasound Universal Guide systems are designed to be as simple and streamlined as possible to provide quick and effective needle guidance for situations that prohibit or do not necessitate the use of more advanced systems, or where realtime ultrasound guidance is not possible, or where the target size is large (i.e. criticality of high accuracy is reduced), etc. It should also be noted that the proposed systems allow for the needle to be inserted both, outside of, or within, the footprint of the US probe. The Epidural System can be used with different types of ultrasound probe e.g. linear, curvilinear etc., and is specifically targeted for procedures which necessitate the insertion of the needle at the centre of the US probe footprint within a range of angles. For ease of reference, it is referred to in this document as "Epidural System" as it will be most commonly used for epidurals. However, it can be used for other procedures which involve the same needle insertion requirements, including spinal anaesthesia, abscess drainage, biopsies, etc.

The general process of using the Loughborough University (LU) Pre-Puncture Ultrasound Needle Guide system is as follows. First, a US scan of the target area is performed and the target is located. The surface of the body is then marked relative to the US probe using a probe attachment (i.e. a surface marking guide). The LU needle guide is then aligned to the mark (or marks made on the surface using the second marking guide), and finally the needle is inserted using the needle guide.

The skilled person will appreciate that the needle guides illustrated in the Figures and described above are examples embodying inventive concepts described herein and that many and various modifications can be made without departing from the invention.

Universal Guide System

Figure 1:
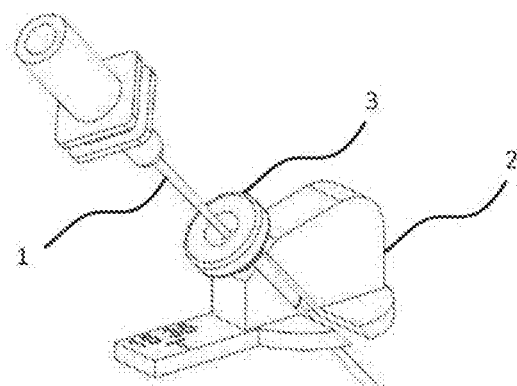
FIG. 1 illustrates an example needle guide which may be utilised in a needle guide system or method of the present invention.
Figure 2:
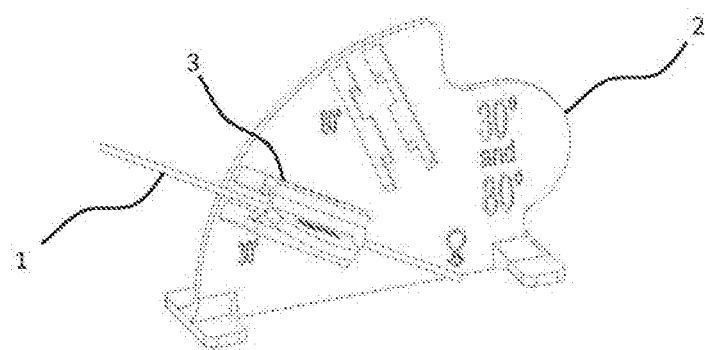
FIG. 2 illustrates another example needle guide which may be utilised in a needle guide system or method of the present invention.

Three types of the universal guide system have been developed,

1. Centre Line Fixed Depth (CLFD) System
2. Centre Line Fixed Angle (CLFA) System
3. Variable Angle and Depth (VAD) System The Centre Line Fixed Depth and the Centre Line Fixed Angle systems can be used with two universal guide types, the Key System and the Protractor System. Here, the 'Depth' refers to the depth of the target, on the ultrasound image, with respect to the body surface; and the 'Angle' refers to the needle insertion angle with respect to the body surface. Typical images of the universal guide demonstrating the main principles of the system are shown in FIG. 1 (Key System) and FIG. 2 (Protractor System). Full description and method of use for both systems are discussed below. It should be noted that while the Protractor System is described below for Fixed Angle use, it can also be used for Fixed Depth.

Figure 3:
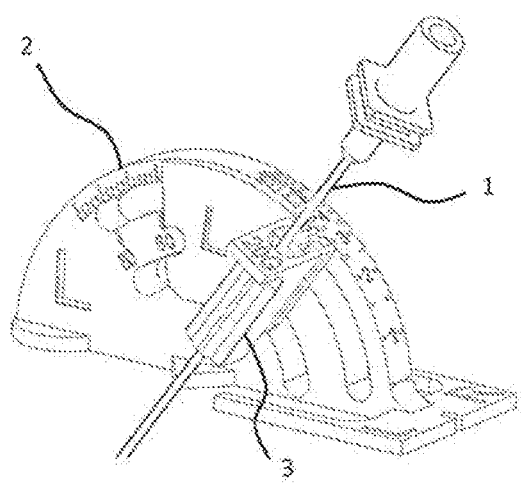
FIG. 3 illustrates another example needle guide which may be utilised in a needle guide system or method of the present invention.

The Variable Angle and Depth (VAD) System works on the same principle as the CLFA and the CLFD systems, but allows one guide to be used for a range of depths and angles. FIG. 3 shows a typical VAD system.

Figure 4:
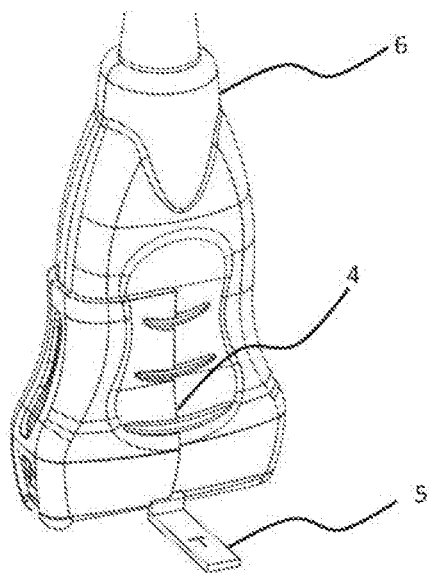
FIG. 4 illustrates an example surface marking guide which may be utilised in the present invention attached to an ultrasound probe.
Figure 5:
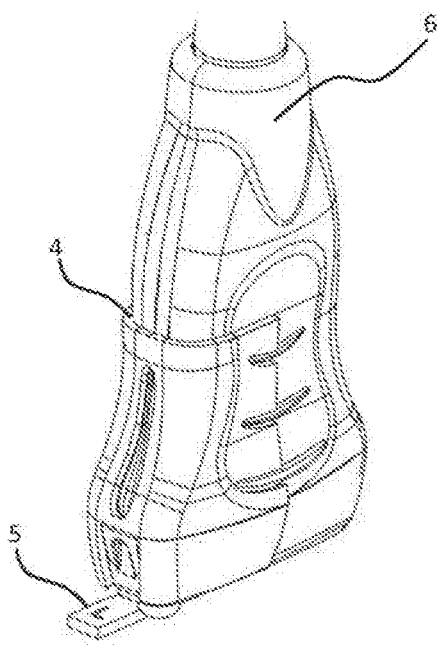
FIG. 5 illustrates another example surface marking guide which may be utilised in the present invention attached to an ultrasound probe.
Figure 6:
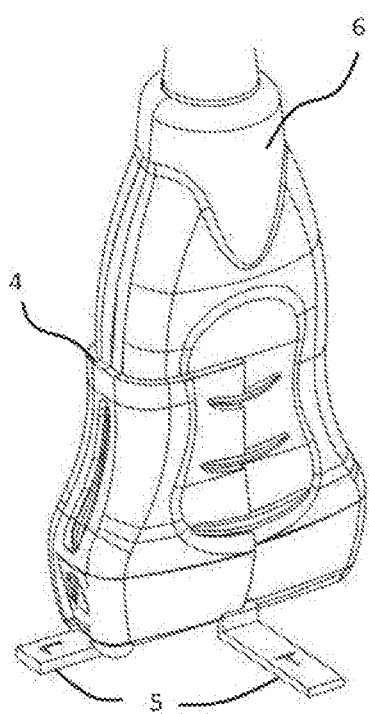
FIG. 6 illustrates the surface marking guides of FIGS. 4 and 5, both attached to an ultrasound probe.

The pre-puncture ultrasound needling procedure is undertaken by first scanning the area. The target is then located, depth measured (on the US monitor) and any structures which can complicate the procedure are determined. Secondly a marking strip attached to the US probe such as typically shown in FIG. 4 and FIG. 5 is used to create a mark on the skin using a marker pen (alternatively, a "transferable marking sticker" may be transferred from the marking strip to the skin when the marking strip is pressed against the skin). The "L" (referring to the Long axis of the US probe) and "T" (referring to the Short axis of the US probe) are used throughout the design as a means to quickly identify the relevant needle guide for the marking strip; different letters may be used for such identification. It should be noted that the marking strip attachment to the probe may be done differently and will depend on the US probe shape and size, which differ depending on the manufacturer. FIG. 6 shows an alternative design of the marking guide which features both L and T marking strips.

Next the needle guide 2 is aligned to the mark on the skin and the needle 1 is inserted. This process differs for the Key and Protractor systems and are discussed further below.

The Universal Guide systems can be used for:

a) Transverse Scanning with Transverse Needle Insertion

This is when the US probe 6 is held transverse to the target structure, and the L marking guide 4 (shown in FIG. 5) is used, so that the needle 1 is inserted transversely to the target (e.g. nerve block).

b) Transverse Scanning with the Longitudinal Needle Insertion

This is when the US probe 6 is held transverse to the target structure, and the T marking (shown in FIG. 4) guide is used, so that the needle 1 is inserted longitudinally with the target (e.g. vascular access).

c) Longitudinal Scanning with Longitudinal Needle Insertion

This is when the US probe 6 is held longitudinal to the target structure, and the L marking guide 4 is used, so that the needle 1 is inserted longitudinally with the target (e.g. vascular access).

d) Longitudinal Scanning with Transverse Needle Insertion

This is when the US probe 6 is held longitudinal to the target structure, and the T marking guide 4 is used, so that the needle 1 is inserted transversely to the target (e.g. nerve block).

e) Longitudinal or Transverse scanning with needle insertion between L and T axes, referred to here as Off-Axis (OA) needle insertion. Users, especially advanced users, will sometimes want to introduce the needle 1 this way to avoid one or more structures on the trajectory to the target. Either the aforementioned second marking guide 4 is used here or a marking strip 5 of a different orientation with respect to the L and T strips is attached to the marking guide. It must be noted that marking strips at varying angles with respect to the L (or T) strip can be attached to the marking guide 4.

The choice between the methods is based on the target structure, clinical decision, and on the experience and/or choice of the clinician.

Figure 7:
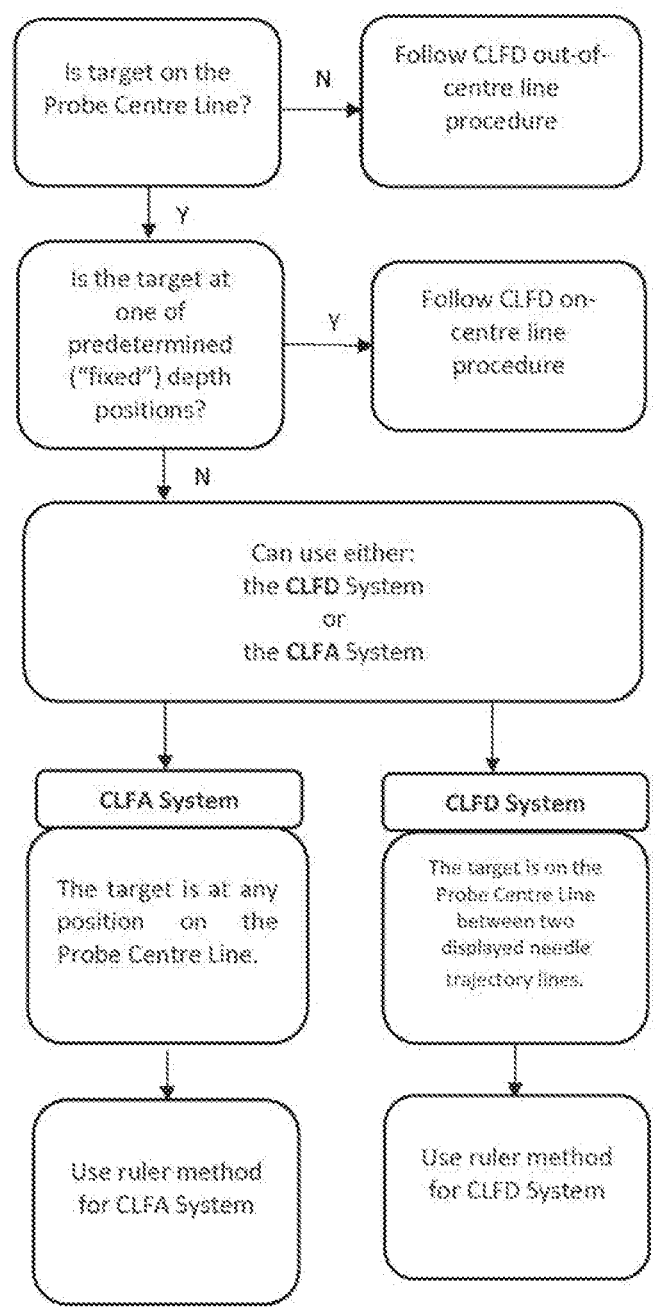
FIG. 7 illustrates a flow chart depicting the process to be followed when selecting the appropriate needle guide system.

Looking now specifically at the Key system (e.g. as seen in FIG. 1), the flow chart in FIG. 7, depicts which process to follow for the Key system depending on the position of the target with respect to the US probe centre line 10 and the needle trajectory line(s) and/or choice of the operator. It should be noted that the needle trajectory lines can be shown automatically on the US screen image once a guide is selected, i.e. software/programming will be embedded within the US software or on a different device, for example as an app on a smartphone or tablet device.

A typical key system is composed of a needle guide 2 as shown in FIG. 1 and a marking guide 4 as shown in any of FIGS. 4, 5 and 6.

The needle guide 2, is for guiding a needle 1 (or an introducer needle) and includes:

an introducer needle and needle 1 of chosen gauge;
a Needle Gauge Insert 3—corresponding to the gauge of the needle/introducer needle 1; these may be colour coded in line with existing universal colour code for gauge of needles, e.g. green for 18 gauge, grey for 16 gauge, etc.;
a Depth Label—The first value gives the depth of the target when the target is on the centre line 10 of the US probe 6; the second value gives the needle insertion length (with respect to the needle guide body) to reach the target on the centre line 10 of the probe 6. These values can be marked at other locations on the guide;
a Needle Guide Body; and
an Alignment strip section of the needle guide body.

In some embodiments, the needle gauge insert 3 may be composed of two parts, which are mounted on the needle before it is inserted into the channel. In other embodiments, the insert may be formed from a flexible material and with a vertical split. These forms of insert may be useful when the needle tip is not uniform with respect to the rest of the cylindrical section of the needle, for example a Tuohy needle (See FIG. 110).

The marking guide 4 is attached to a US probe 6 and includes:

a Marking Guide Body; and
one or more Marking Strips 5 (which in this example is/are an integral part of the Marking Guide Body).

Figure 8:
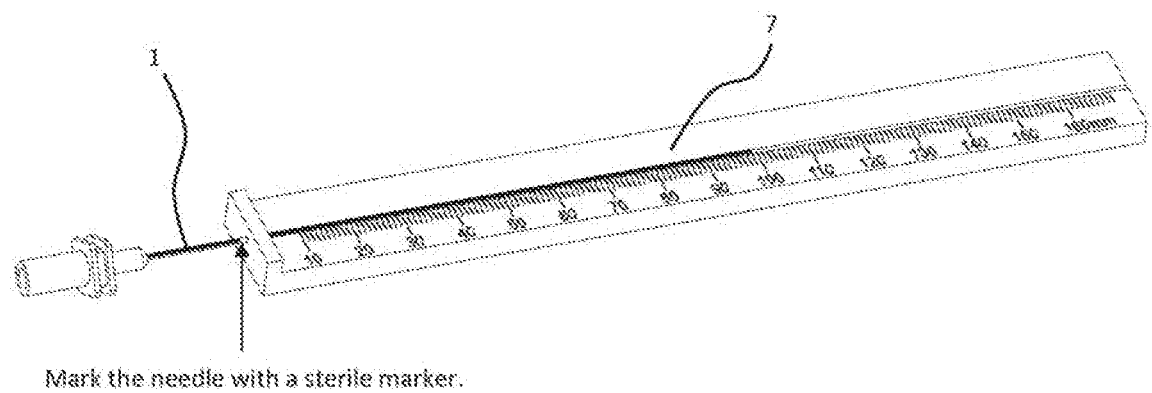
FIG. 8 illustrates a needle insertion length rule.

The kit may also include a depth gauge 7 to be used when the user wants to mark the needle insertion length on the needle—see FIG. 8.

The key pre-puncture ultrasound guide body will come in a sterile pack. The needle gauge insert may be supplied separately to the guide body, either independently or in a pack with an introducer needle and a needle 1 of corresponding gauge, and will also come in a sterile pack. The needle gauge inserts, which are needle gauge (or introducer needle gauge) specific, will be available for a range of needle gauges. The needle guide body can be used for different needle gauges as the outside dimensions of the inserts are all identical. The Key pre-puncture ultrasound guide body and the Needle Gauge Insert are designed to be single use and disposable. However, the Marking guide 4 can be reusable and needs only cleaning (instead of sterilising) as it is attached to a non-sterile US probe 6.

FIGS. 4, 5 and 6 show the marking guides fitted to a linear US probe 6. While the marking guides are shown with a linear US probe 6 the system can also be used with a curvilinear, or any other, US probe 6 by attaching an appropriate marking guide 4 to suit the shape and size of the probe 6.

Centre Line Fixed Depth (CLFD) System—Target on US Probe Centre Line

The Centre Line Fixed Depth (CLFD) pre-scan system is intended to provide a simple needle guidance system. An assembly of the CLFD Key system is composed of the Key Guide assembly, shown in FIG. 1 and the Marking Guide assembly shown in one of FIGS. 4, 5 and 6. The CLFD Key system provides a guide for the needle 1 to reach a target on the centre line 10 of the US probe 6 when such a target is at the depth indicated on the Key System Needle Guide body. Both the US probe centre line target depth and the needle insertion length (with respect to the needle guide body to reach the centre line target) are fixed for each guide and can be given on the guide body.

A Key Needle Guide body could be provided for target depth increments of 5 mm (or other increments), and for each US probe centre line depth increment the respective needle insertion length can be marked on the guide body below or adjacent to the centre line depth value.

The process of using the system is as follows:

1. The clinician will first attach the chosen marking guide 4 (L, T, Dual, or multi) to the US probe 6 and perform a pre-scan of the patient.
2. The area surrounding the target is examined to establish if there are any critical regions which could cause complications, such as important blood vessels, to be avoided. If any such complications are discovered the clinician must make a judgement as to which procedure is most suitable (see Flowchart in FIG. 7, or using the OA needle insertion method).
3. Similar to existing commercial products for Real-Time Guidance, it is aimed that needle trajectory lines are displayed on the US image for Key Needle Guide bodies of different target depths, i.e. there will be embedded software to display the needle trajectory lines (adapted for different manufacturer US probes), in addition to other information, e.g. needle insertion depth. The clinician must orientate the US probe 6 correctly so that the target is located on the centre line 10 of the probe 6, with the marking strip 5 'pointing' towards the area of correct approach direction (i.e. a left or right hand approach for L marking guide, or either side of the probe 6 for the T marking guide). If the target is at the intersection of the US probe centre line 10 and one of the needle trajectory lines, the target depth is measured; this corresponds to a specific Key Guide. If the needle trajectory lines do not go through the target when it is placed on the US probe centre line 10 then methods described further below can be followed.

Figure 9:
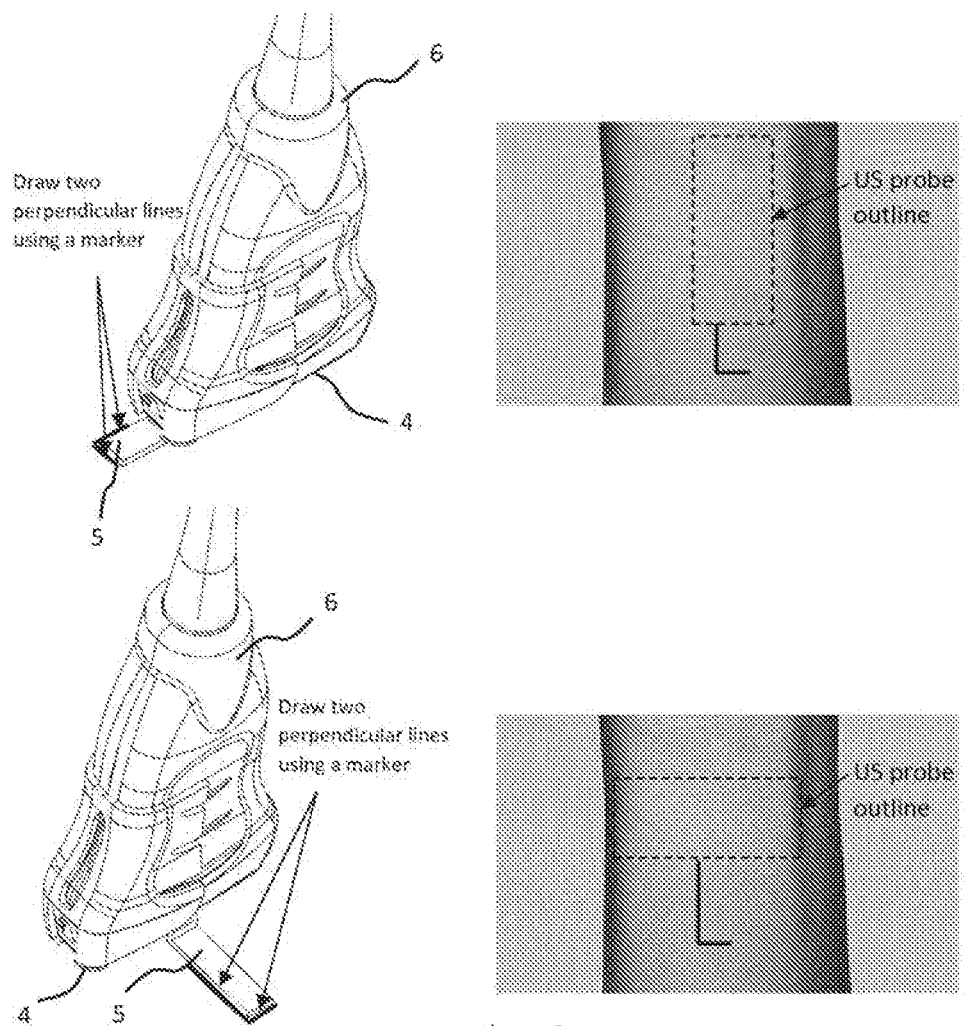
FIG. 9 illustrates the surface marking guides and ultrasound probes of FIGS. 4 and 5 along with corresponding marks made on skin when the guides are utilised in accordance with the present invention.
Figure 10:
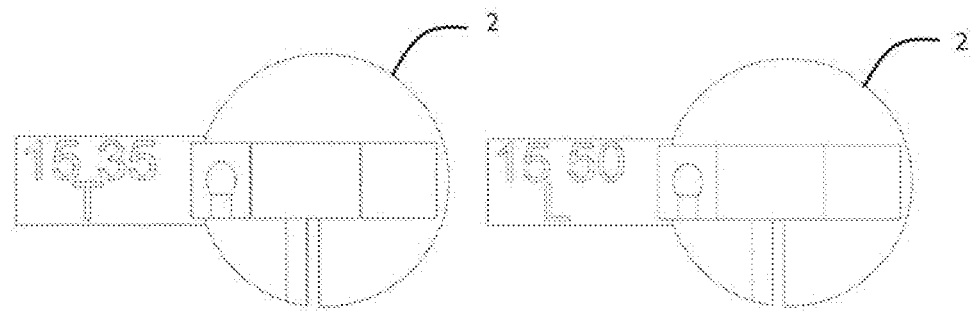
FIG. 10 is top view of two needle guides which may be utilised in a needle guide system or method of the present invention.

4. The clinician then makes a mark on the skin using the marking strip 5 part of the Marking Guide body attached to the US probe 6 as shown in FIG. 9. A marker pen is used to create this mark on the skin. Alternatively, a "transferable marking sticker" may be transferred from the marking strip to the skin when the marking strip is pressed against the skin.
5. The marking on the skin may be covered over using a sterile transparent tape (so that it does not rub off when the skin is cleaned). The skin is then disinfected using the appropriate technique.
6. The clinician then selects the appropriate needle guide 2 corresponding to the measured depth on the US probe centre line 10, as noted from Step 3 above. The outside of the sterile packaging will indicate the target depth. Once removed from the packaging there is more information on the guide itself, such as the needle insertion length, as shown in FIG. 10. The 'T' and 'L' notations may be replaced by any two letters that are easy to differentiate. The positions of the numbers and letter marking may of course change.

Figure 11:
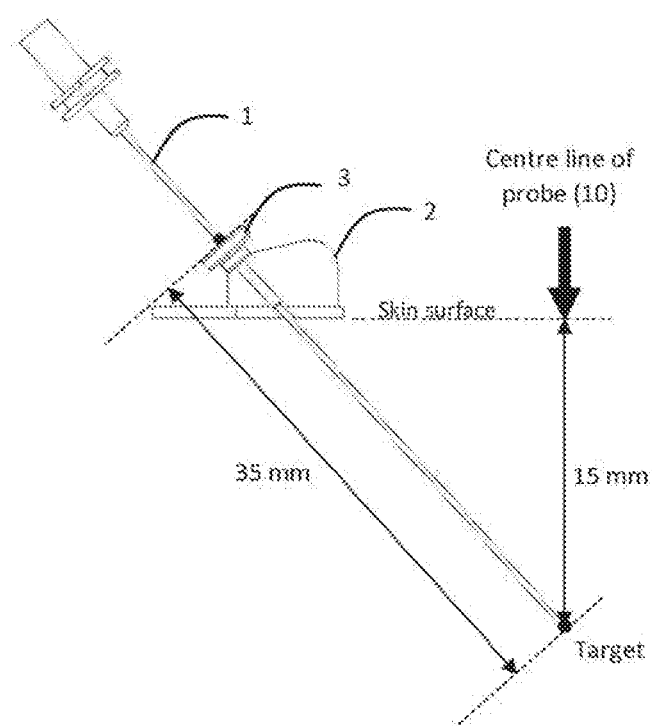
FIG. 11 is a sectioned view showing a needle guide positioned on a skin surface and a needle inserted in the needle guide.

For example, the text '15'& '35' (shown in FIG. 10), for the Key Guide corresponding to the T Marking guide 4 (shown in FIG. 4), indicates that this guide is designed to reach a target at a depth of 15 mm on the centre line 10 of the US probe 6, and the needle 1 should be inserted 35 mm (with respect to the top face of the Needle Gauge Insert) to reach the target as shown in FIG. 11. The L and T denote whether the guide is intended for use with an L or T marking guide 4 respectively. The needle insertion length can be marked using the depth gauge 7 shown in FIG. 8, or any other sterile rule, and sterile marker.

Figure 12:
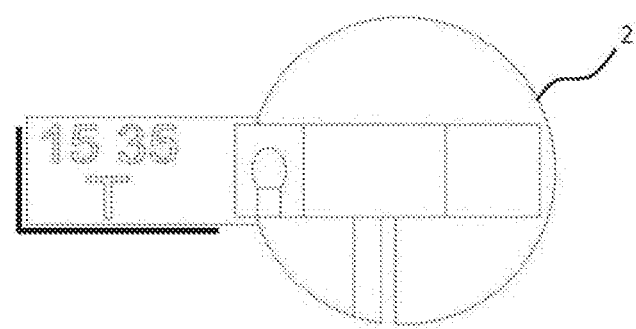
FIG. 12 is a top view of a needle guide and marks made on a body in accordance with an embodiment of the present invention.
Figure 13:
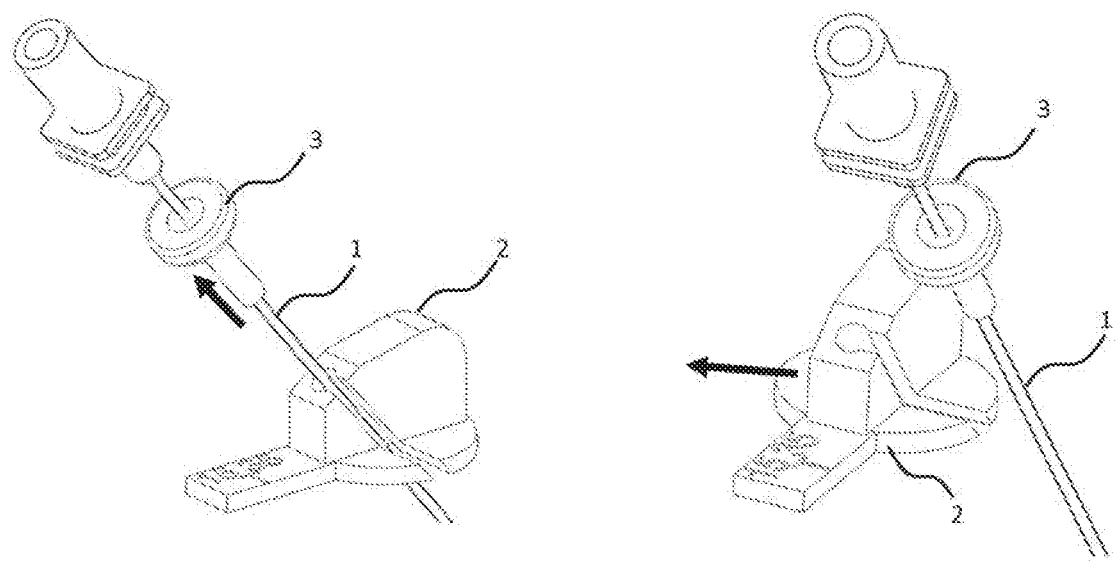
FIG. 13 illustrates the removal of a needle guide from a needle.

7. The Needle Insertion Length Rule is used to make an accurate mark on the needle 1 with a sterile marker using the needle insertion length marked on the Key Needle Guide body for centre line targets as described above in Step 6. The needle is inserted through the hole on the depth gauge 7, as shown in FIG. 8, so that the tip of the needle 1 travels up the scale the further it is inserted. The needle 1 should be inserted until the tip of the needle 1 is in line with the desired value shown in Step 6. The needle 1 is then marked and removed.
8. The alignment strip of the Key Needle Guide Body is then aligned with the ink marks created on the body in Step 4, as typically shown in FIG. 12 (or other methods of marking). The needle guide body is handled by the clinician using, for example, a tab.
9. The clinician will then slide the appropriately sized Needle Gauge Insert 3 (see FIG. 1) for the required needle gauge into the Key Needle Guide Body. This action could be done at any point.
10. The needle 1 (or the introducer needle) is then inserted into the funneled Needle Gauge Insert 3 and the needling procedure is carried out. The needle 1 should be inserted until the depth mark lines up with the edge of the insert.
11. If at any point the needle guide 2 is no longer required, the Needle Gauge Insert 3 can be carefully pushed up the needle 1 to separate it from the Key Needle Guide Body. This will then allow the Needle Guide Body to be moved away from the needling site using the slot as shown in FIG. 13. The Needle Gauge Insert 3 may remain with the needle 1, or it can be removed if it is made of two parts which become loose when pulled out of the Needle Guide Body. Other design methods may be considered to allow the Needle Gauge Insert 3 to be removed from the needle 1 while the needle 1 is in the body; for example, by manufacturing this insert 3 using a flexible material and with a vertical split.
12. The clinician progresses with the procedure as desired. It should be noted that the above sequence/steps is an example that can be modified depending upon the clinician's own experience, preferences or demand of the situation.

Centre Line Fixed Depth (CLFD) System—Target not on US Probe Centre Line

Figure 14:
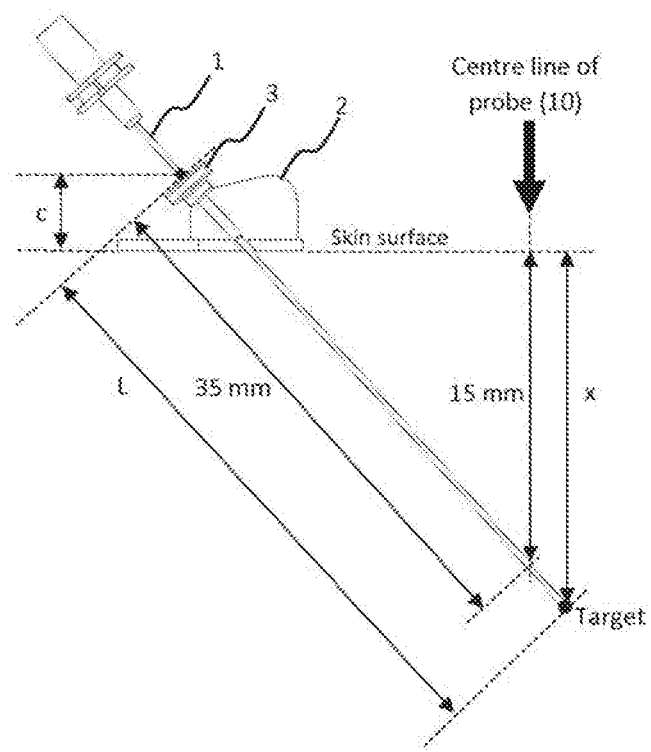
FIG. 14 is a sectioned view showing a needle guide positioned on a skin surface and a needle inserted in the needle guide, where the target is not on the centre line of the ultrasound probe.

If the target is on one of the Needle Trajectory Lines but is not on the Centre line 10 of the US probe 6 as indicated in FIG. 14, then the depth of the target (with respect to the base of the probe 6) must be measured on the ultrasound image and the corresponding needle insertion length is read from a chart provided, typically as shown in Table 1. For example, for a "Fixed" Depth 15 mm Key Needle Guide body, and a target depth of 21 mm, the needle insertion length is given as 44 mm. Such information is dependent on the dimensions of the Needle Guide body and obviously will differ if the relevant dimensions of the Needle Guide body are changed (during the design phase); such dimensions can also be provided automatically on the US image following a "click" on a target placed on any of the needle trajectory lines (described in Step 3 above). It should also be noted that the software may be embedded in other devices.

TABLE 1

| Target Depth (mm)/X | Needle Insertion Length (mm)/L |
|---|---|
| 20 | 42.4 |
| 21 | 43.9 |
| 22 | 45.4 |
| 23 | 46.9 |
| 24 | 48.3 |

The values for Table 1 have been calculated using Equation (1), shown below, for a 15 mm 'fixed' depth Needle guide Body, and with reference to dimensions shown in FIG. 14. It should be noted that the needle insertion length includes the distance traveled through the guide.

$$L = 35\frac{(X+C)}{15+C} \tag{1}$$

It must be noted that a different equation would be used if instead of dimension 'C', a different dimension, such as the dimension along the insertion path from the entry point of the Needle Gauge Insert 3 to the base of the Needle Guide Body, is given.

Centre Line Fixed Depth (CLFD)—Random Depths on the US Probe Centre Line (Using Rule Method)

Figure 15A:
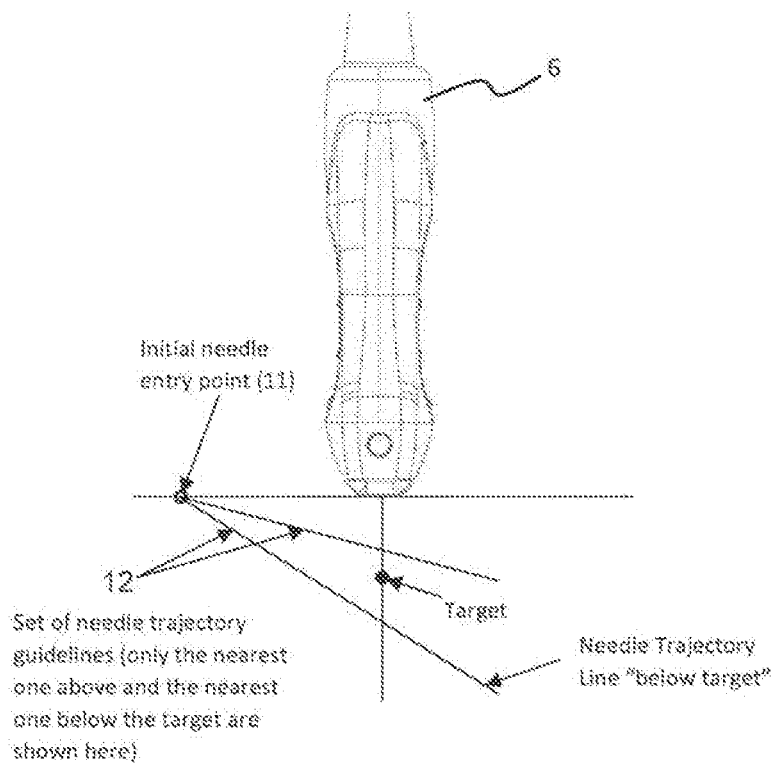
FIG. 15(*a*) is a sectioned view of an ultrasound probe positioned on a skin surface and a section view showing a target, needle entry point and trajectory lines of a Centre Line Fixed Depth needle guide system.
Figure 15B:
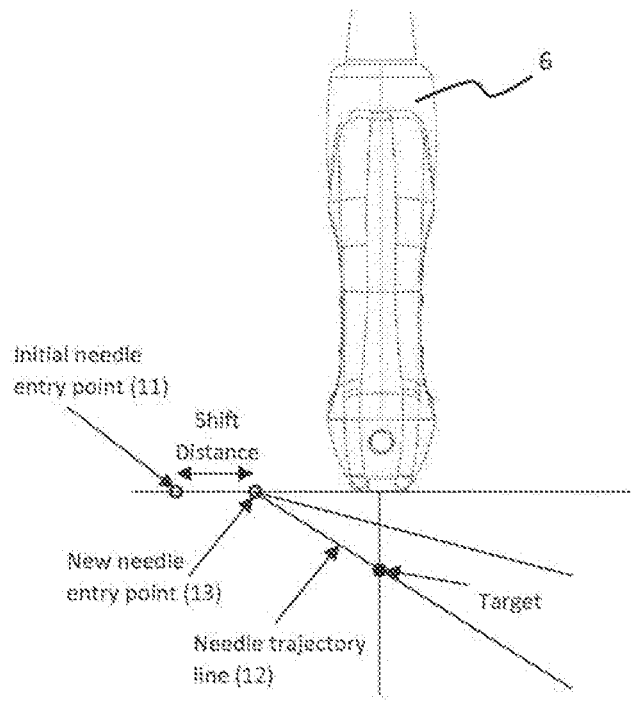

If the target falls in-between the trajectory lines, provided by the US display for the CLFD for different depths (i.e. when the target is not at a fixed depth), then the needle entry point 11 must be moved closer to the US probe 6 in order to reach the target by selecting the Needle Guide Body corresponding the needle trajectory line underneath the target point on the US display (i.e. corresponding to the Needle Guide body for the next larger fixed depth with respect to the target depth). The system calculates how much the Needle Guide Body will need to be shifted to reach the target. The needle trajectory line used (and then shifted) is always the one "below" the target, so that the needle insertion point is moved closer to the US probe centre line 10. This is shown diagrammatically in FIGS. 15(*a*) & (*b*) and FIG. 16. It should be noted that if the trajectory lines are not visible, the depth of the target point is measured and the Needle Guide body corresponding to the next larger fixed depth with respect to the target depth is selected.

Figure 16:
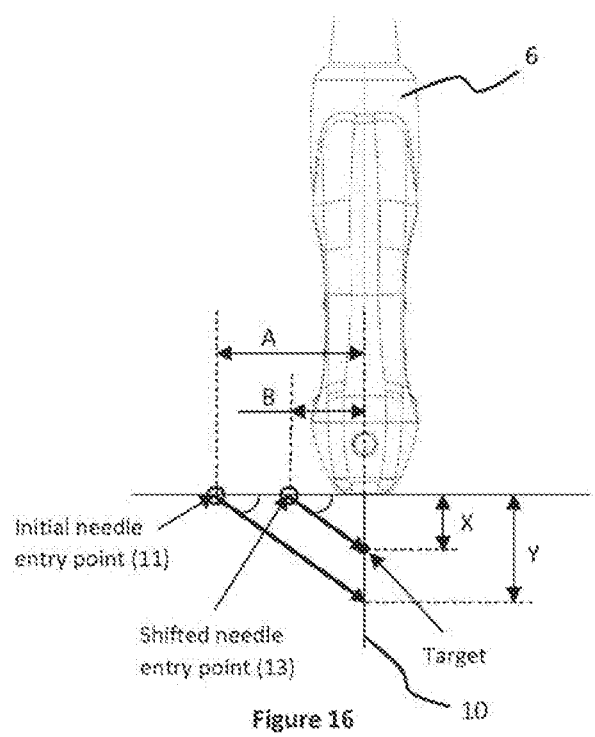
FIG. 16 is a sectioned view of an ultrasound probe positioned on a skin surface and a section view showing a target and trajectory lines of a Centre Line Fixed Depth needle guide system and illustrates a shift of needle entry point required for the system.

With reference to FIG. 16, the 'shift distance' (A–B) is calculated using the measured target depth distance (X), the known depth value for the selected Needle Guide Body (distance Y); the needle entry point distance (A), with respect to the US probe centre line 10, of the selected Needle Guide Body (i.e. the Needle Guide Body corresponding to the trajectory line below the target point, which also corresponds to the Needle Guide body for the next larger fixed depth with respect to the target depth).

The 'shift distance' (A–B) is obtained using equation (2), where A and Y are constants for a given fixed depth needle guide body and X is the depth of the target. It must be noted that different equations can also be used to work out the 'shift distance' (A–B).

$$\text{Shift Distance} = A - B = A - X\frac{A}{Y} \qquad (2)$$

New marks are made on the skin using a similar technique to the one described below for the "Centre Line Fixed Angle (CLFA) Key System—Fixed Angle Needle Insertion", which also describes another alternative by means of a needle guide 2 which incorporates a rule, illustrated in FIGS. 76 and 77.

Centre Line Fixed Angle (CLFA) Key System—Fixed Angle Needle Insertion

This system can be used to approach a certain location at a desired angle (e.g. for venous access). The Centre Line Fixed Angle (CLFA) key system allows a target at any depth on the centre line 10 of the US probe 6 to be reached at any given angle (e.g. 20°, 30°, 40° etc.). This is achieved by shifting the Needle Guide Body placement closer to or further from the US probe centre line 10 when clinically possible/suitable, to hit a target shallower or deeper respectively. A set of rules and marking gauges have been developed for this method to allow the skin position mark, referred to here as the "Gamma" mark, to be positioned into the correct position as described in the process below.

Figure 17:
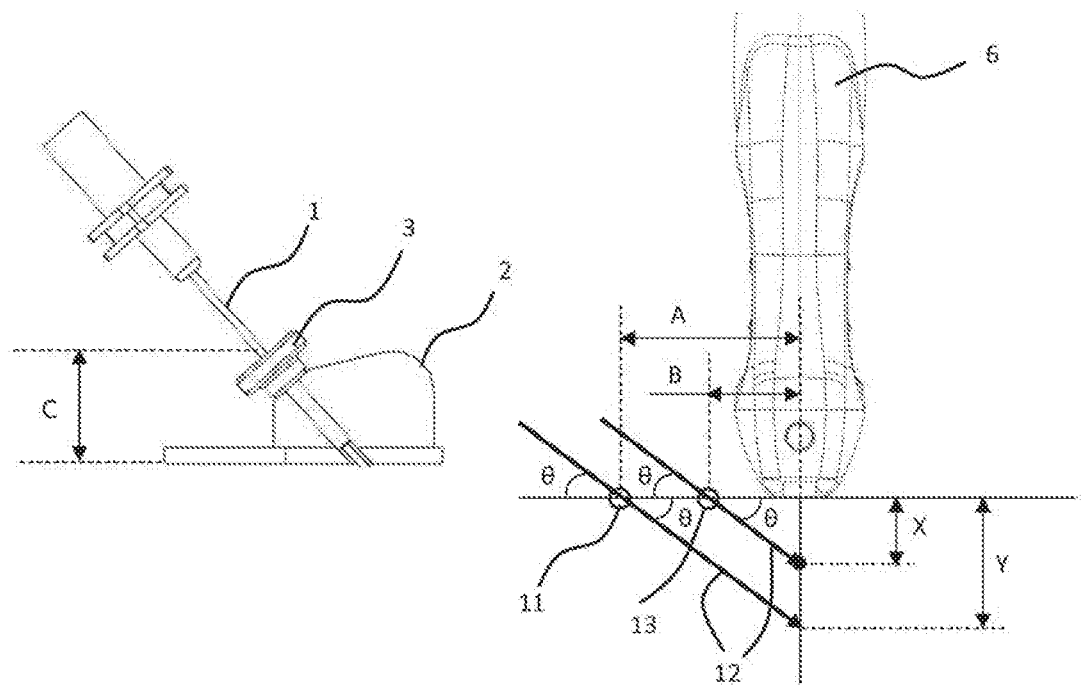
FIG. 17 is a sectioned view showing a needle guide positioned on a skin surface and a needle inserted in the needle guide and a sectioned view of an ultrasound probe positioned on a skin surface and a section view showing a target and trajectory lines of a Centre Line Fixed Depth needle guide system illustrating a shift of needle entry point required for the system.

1. The pre-puncture ultrasound and skin marking processes are undertaken in the same way as described above for the CLFD System with the target on US probe centre line 10 (steps 1 to 5).
2. Having completed the skin marking, the user finds the table (or refers to electronic information) relating to the desired needle insertion angle and checks, on the corresponding chart, that the required depth is within the range of the guide used, then reads the position the Needle Guide Body should be placed at, and the insertion length for the needle 1. Alternatively this information can be programmed to show on the US monitor screen (i.e. using embedded software), or on a separate computer screen, or on a smartphone (and similar devices), and remove the need for the clinician to consult the depth charts.
3. Table 2 shows a small selection of the depth chart for a 40° CLFA needle guide 2. The values are found using equation (3) and equation (4). The dimensions of interest are also shown in FIG. 17.

TABLE 2

Example of Depth Chart for 40° Needle Guide Body (T Alignment)

| Target Depth, X (mm) | Shift Distance for Needle Guide Body (mm) | Needle Insertion Length (mm) |
|---|---|---|
| 10 | 2.0 | 29 |
| 11 | 1.0 | 31 |
| 12 | 0.0 | 32 |
| 13 | −1.0 | 33 |
| 14 | −2.0 | 35 |
| 15 | −3.0 | 36 |
| 16 | −4.0 | 37 |
| 17 | −5.0 | 39 |
| → 18 | −6.0 | 40 ← |
| 19 | −7.0 | 41 |
| 20 | −8.0 | 43 |

Figure 18:
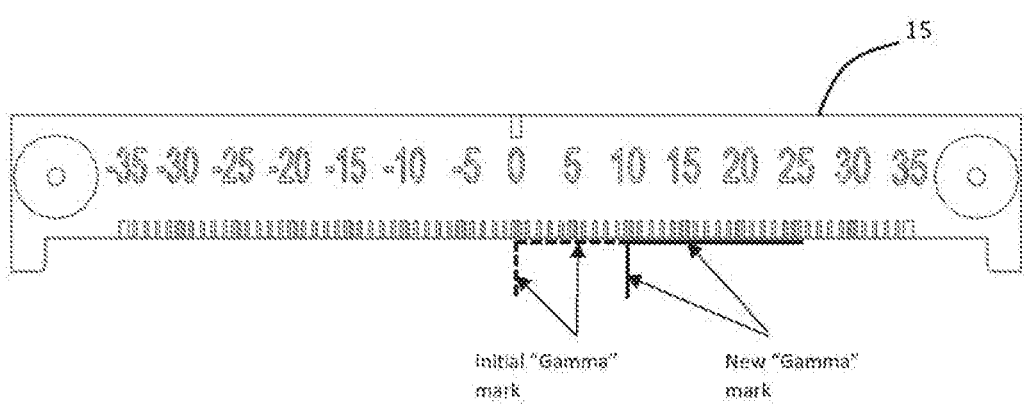
FIG. 18 is a top view of a marking rule illustrating a shift of a mark.

4. If a depth of 18 mm (i.e. the depth of the target measured along the centre line 10 of the US probe 6) is required, the user reads across the corresponding "position" (Shift Distance) value in the second column (which is −6 mm in this case), as well as reading the needle insertion length, given in the third column (which is 40 mm in this case). Alternatively this information can be programmed to be outputted by the US software to give the aforementioned dimensions when the US user selects the target on the US screen.
5. The rule is then used to reposition the marking lines on the skin as shown in FIG. 18.

$$\text{Shift Distance} = A - \frac{X}{\tan(\theta)} \qquad (3)$$

$$\text{Needle Insertion Length} = \frac{X + C}{\sin(\theta)} \qquad (4)$$

where, A=US probe Centre line; X=Target Depth; θ=Needle Guide Angle; and C=Distance between base of Needle Guide Body and the Marking Position on the Needle Gauge Insert Alternatively a slidable extension strip on the marking guide can be incorporated to obtain the modified marking line as per the calculations on the depth chart, or an integrated laser/light pointer can be used to help with skin mark for both with and without shift on the skin.

6. A new position mark is created on the skin using, for example, a different colour/type marker pen at the position noted from the depth chart (in this case −6.0 mm), as shown in FIG. 18.
7. The marker line parallel to the Marking Rule is extended on the skin surface (the marker line is referred to as "marking line" hereafter). The new position mark is drawn as a line on the skin which is perpendicular (or near perpendicular) to the marker line as shown in FIG. 18; such a position can also be drawn as a "dot" and referred to as a "marker dot". It should be noted that different designs of Marking Rule 15 may be used.
8. The needle guide 2 is first positioned on the initial marking line. It is then moved along the surface of the skin until the needle guide 2 is positioned on the new position mark as shown in FIG. 19. Alternatively, the line perpendicular to the "marking line" could be replaced by just a dot on the marking line at the intersection of the two lines, and the needle guide 2 moved along the marking line until the end corner aligns with the dot. It should be noted that the needle guide 2 can be placed directly at the new position mark without having to align it with the initial marking line first. Alternatively Instead of shifting the mark originally made on the body as described above and illustrated in FIGS. 18 and 19, the needle guide 2, shown in FIG. 76, which incorporates a rule, can be placed at the desired position without shifting the original mark made on the skin. In this illustration, depicted in FIG. 77, the positive numbers refer to a shift towards the US probe central axis, and the negative numbers refer to a shift away from the US probe central axis. It should be noted that needle guides with just positive numbers or just negative numbers could also be used.

9. The needle 1 is inserted into the funneled insert 3 and the needling procedure is carried out. The needle should be inserted until the depth mark lines up with the edge of the insert 3 as discussed previously (It should be noted that an introducer needle may be used first to facilitate the needle insertion into the body).

10. If at any point the needle guide 2 is no longer required, the insert 3 can be carefully pushed up the needle 1 to separate the insert 3 from the Needle Guide Body. This will then allow the Needle Guide Body to be moved away from the needle site by exiting the needle via the slot as discussed previously.

11. The clinician progresses with the procedure as desired. It should be noted that the above sequence/steps is an example that can be modified depending upon the clinician's own experience, preferences or demand of the situation.

In the various procedures discussed above, various alternative forms of marker guide and needle guide 2 could be used, with different features defining the marks. Examples are shown in FIGS. 20 to 22.

Figure 20A:
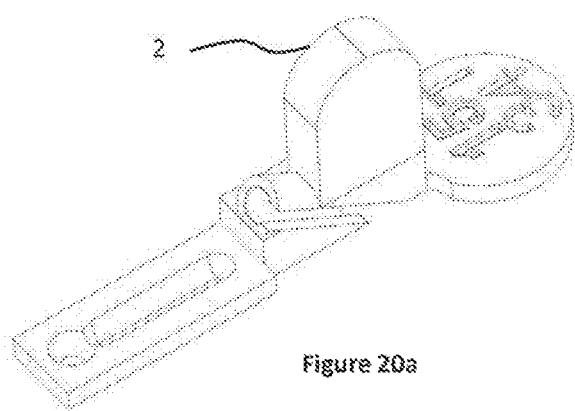
FIG. 20*a* is a perspective view of an alternative needle guide which may be utilised in a needle guide system or method of the present invention.
Figure 20B:
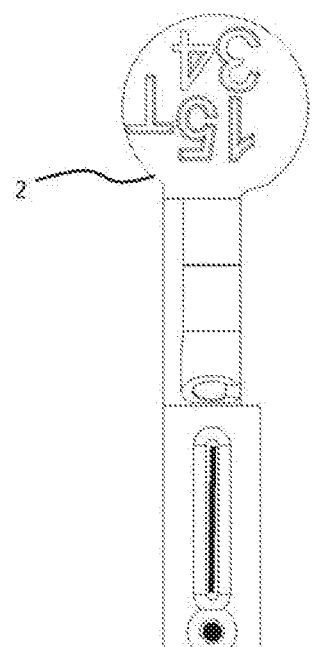
FIG. 20b is a top view of the needle guide of FIG. 20a illustrating marks made in accordance with a method of the present invention.
Figure 20C:
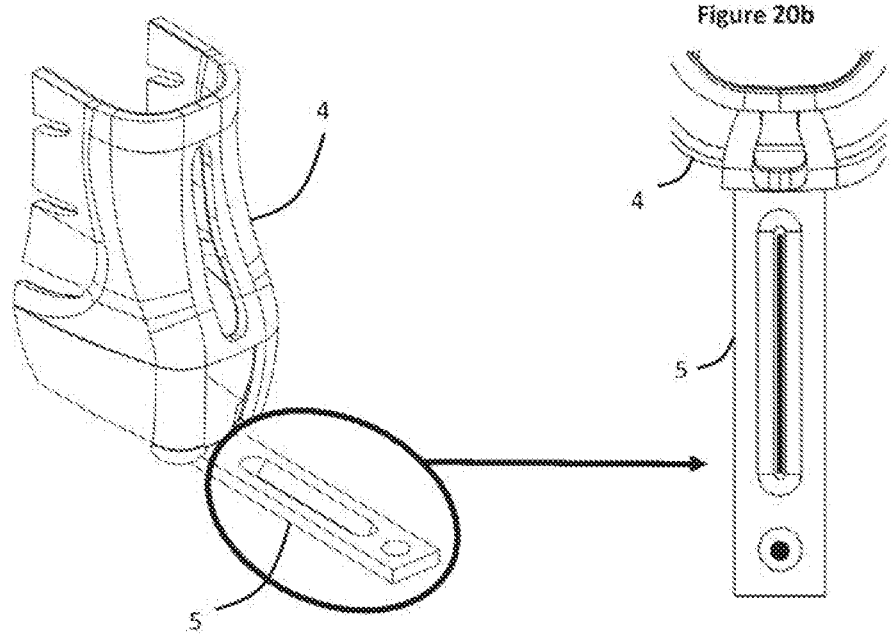
FIG. 20c is a perspective view and top view of a surface marking guide corresponding to the needle guide of FIGS. 20a and 20b.

FIG. 20 shows a line and dot arrangement for marking. The marking guide 4 and the needle guide 2 both have a recessed chamfered slot and hole which the line and dot can be marked in/aligned with respectively. To align the guide, the hole is first aligned with the dot, and then, whilst keeping the dot in position, the guide is rotated such that the line is within the slot. Alternatively, the slot could be aligned with the line first and then the guide is shifted to align it with the dot.

Figure 21A:
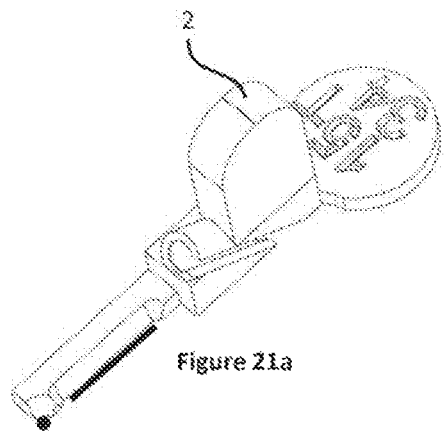
FIG. 21a is a perspective view of another alternative needle guide which may be utilised in a needle guide system or method of the present invention.
Figure 21B:
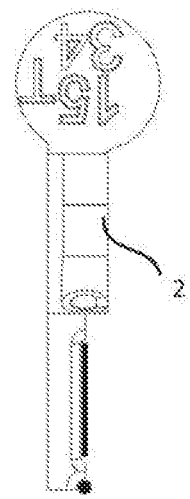
FIG. 21b is a top view of the needle guide of FIG. 20a illustrating marks made in accordance with a method of the present invention.
Figure 21C:
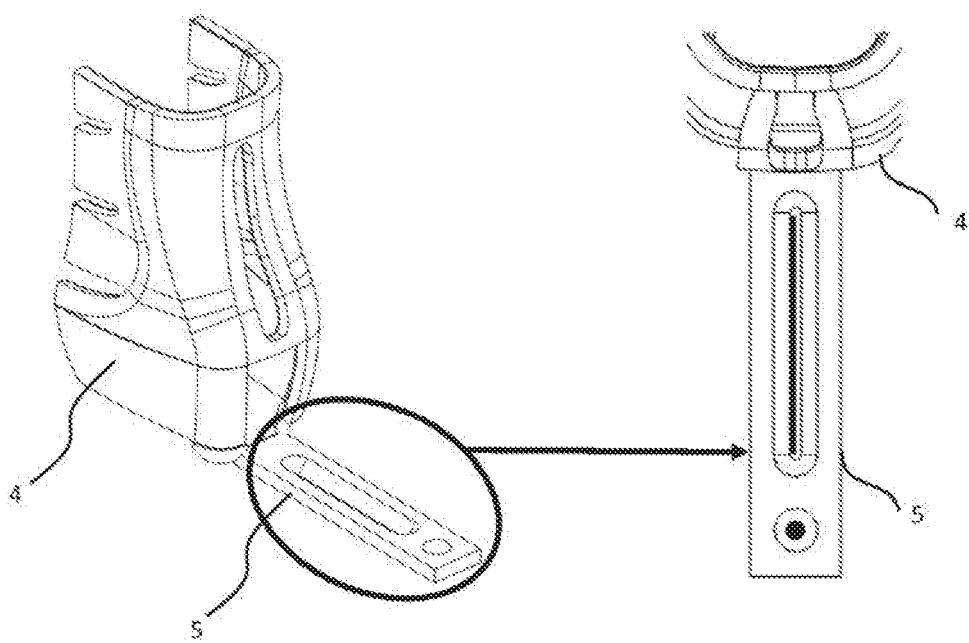
FIG. 21c is a perspective view and top view of a surface marking guide corresponding to the needle guide of FIGS. 20a and 20b.

FIG. 21 shows a similar arrangement but in this case the features on the needle guide 2 are in effect one half of the slot and one quarter of the hole of the arrangement see in FIG. 20, to provide a recessed straight edge and a notch used for lining up with the line and dot respectively. The quarter circle allows the clinician to view the dot easily without obstruction. In this case the marking guide 4 is the same as the one seen in FIG. 20.

Figure 22A:
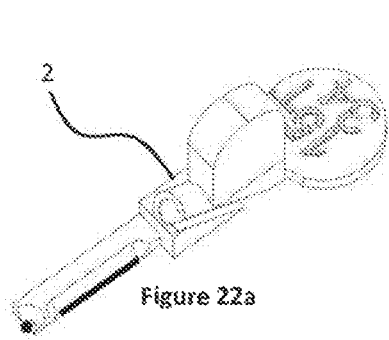
FIG. 22a is a perspective view of a further alternative needle guide which may be utilised in a needle guide system or method of the present invention.
Figure 22B:
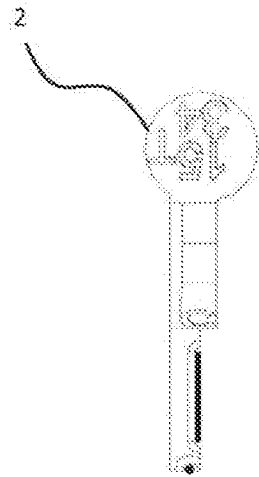
FIG. 22b is a top view of the needle guide of FIG. 20a illustrating marks made in accordance with a method of the present invention.
Figure 22C:
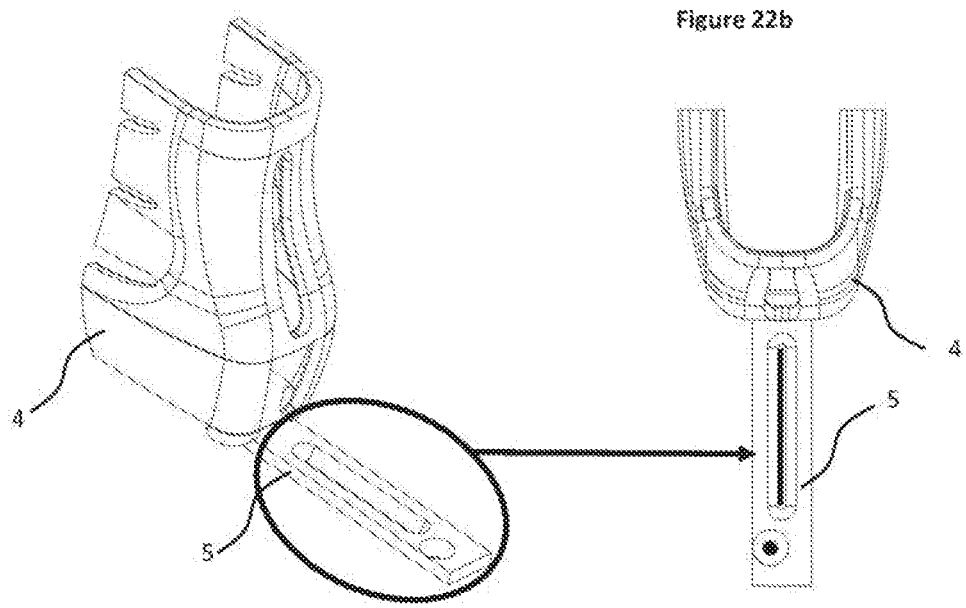
FIG. 22c is a perspective view and top view of a surface marking guide corresponding to the needle guide of FIGS. 20a and 20b.

FIG. 22 shows another variant. In this case, the hole for marking the dot is offset from the line of the slot (the slot being in-line with the US plane). The needle guide 2 has a recessed straight edge (as in FIG. 21) to align with the line, and a semi-circular notch at the end to line up with the dot.

Various other arrangements of features are suitable to achieve the desired marking and alignment. It should be noted that some marking arrangements may provide better alignment accuracy; for example, a 'line and dot' may provide a more accurate and easier alignment arrangement compared to a 'dot and dot' feature.

Figure 23:
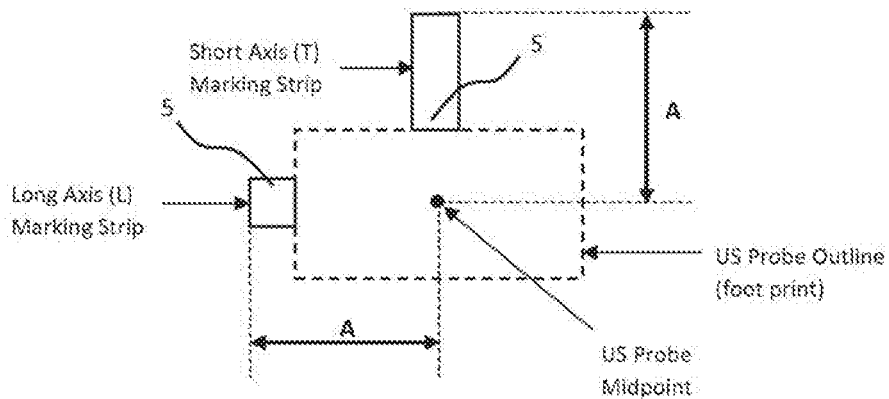
FIG. 23 illustrates the positioning of marking guides on an ultrasound probe in order to enable the use of a common needle guide.

The systems described above have featured different Needle Guides 2 for Longitudinal and Transverse applications. The need for this arises because the same length of marking guide strip 5 is used for both orientations. It is, however, possible to change the dimensions of the marking guide strips in order to have a common Needle Guide for both Longitudinal and Transverse applications. This is achieved by ensuring that the distance of the L and T marking strips furthest edge to the US probe midpoint is equal (shown in FIG. 23). The same also applies to other forms of marking the skin, for example an optical system would be positioned at the same distance with respect to the probe centre line 10 for both orientations.

Making these distances the same means that the needle guides 2 only need to be produced in one size to reach a given depth removing the need for T or L markings on the Needle Guide Bodies 2 thus simplifying the system.

Protractor System

The Protractor system is used for fixed angle procedures similar to the Key CLFA System as outlined above.

There are two methods of positioning the protractor pre-puncture ultrasound system; that will be referred to in the following as the "Gamma" marking method and the "Line & Dot" method respectively.

Figure 24:
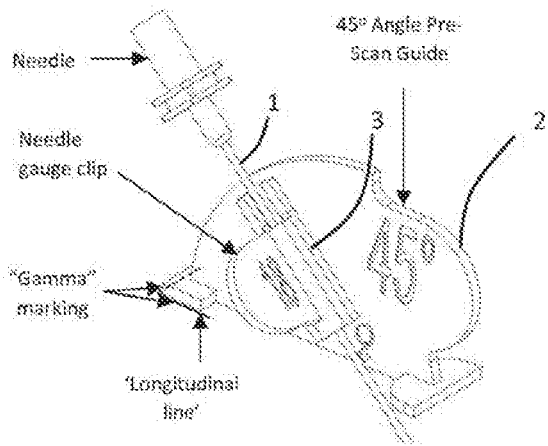
FIG. 24 is a perspective view of a needle guide according to the protractor system with a needle inserted in the needle guide.
Figure 25:
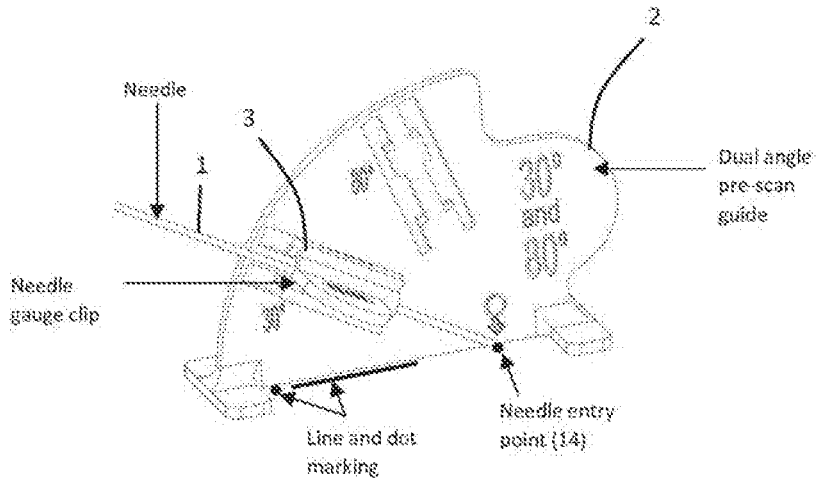
FIG. 25 is a perspective view of a needle guide according to the protractor system and enabling selection of two angle of insertion with a needle inserted in the needle guide.

Typical examples of the protractor system are shown in FIGS. 24 and 25. The system is used with a needle 1, having a depth mark (as in the systems described above). The needle guide 2 includes a needle guide body (referred to as a "protractor" because of the shape) and a quick release needle gauge clip 3 (corresponding to the gauge of the needle 1) that attaches to the needle guide body at the desired angle. This system uses the same other components as the Key Systems, i.e.: a US probe 6, marking guide body 4 and marking strip 5 (for example as shown in FIGS. 4, 5 and 6, and a needle insertion length rule (for example as shown in FIG. 8).

The protractor pre-scan system will be packaged in a sterile pack containing a range of different gauges of Needle Gauge clip 3. The same protractor body can be used for different needle gauges by simply choosing a Needle Gauge clip 3 of the desired gauge. All of the components are designed to be single use and disposable.

The needle guide 2 seen in FIG. 25 differs from the guide in FIG. 24 in that it caters for two different angles of insertion. The needle gauge clip 3 can be attached in a selected one of two different positions depending on the chosen angle. The two needle guides 2 also show different features for alignment with the skin marks, as discussed below. Such alignment features can be used for either of the guides.

Centre Line Fixed Angle (CLFA) System—Gamma Marking

The "Gamma" Protractor system utilises the "Gamma" (Square Edge) marking guide 4 shown in FIG. 24 (although any appropriate marking guide 4 may be used, including those discussed above in the context of the 'key system'). This guide is used in the following manner.

1. The pre-scan and skin marking processes are undertaken in the same way as described above. Alternatively the "Gamma Marking" protractor can be used for the dual marking guide system, shown in FIG. 23 (with appropriate tables).

2. Using the "gamma" marking guide, the "gamma" mark should be drawn such that the longitudinal line is on the same side as the needle 1, shown in FIG. 24.

3. The clinician selects the desired angle needle guide body for the procedure and consults the depth charts to determine the shift distance in order to reach the target. A similar process as stated above, in Step 2 of the "Centre Line Fixed Angle (CLFA) Key System—Fixed Angle Needle Insertion" Section, is undertaken.

4. The Needle Gauge clip 3 of the appropriate gauge is chosen to suit the needle 1 to be used, and is inserted into the needle guide body.

Figure 26:
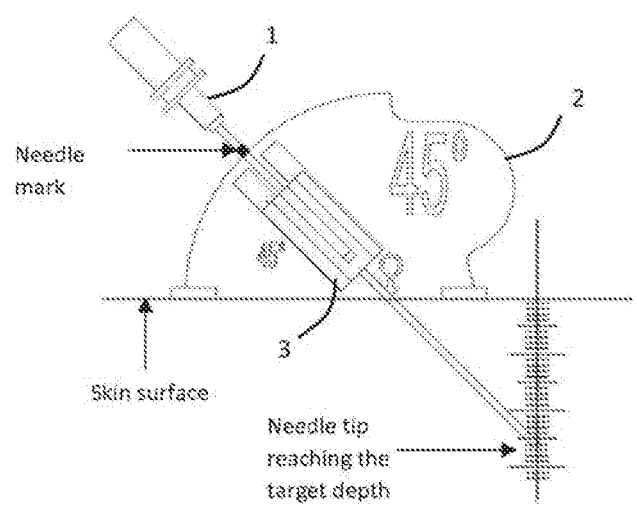
FIG. 26 is a side view of the needle guide of FIG. 24 with a needle inserted within it and extending through a skin surface to a required depth.
Figure 27:
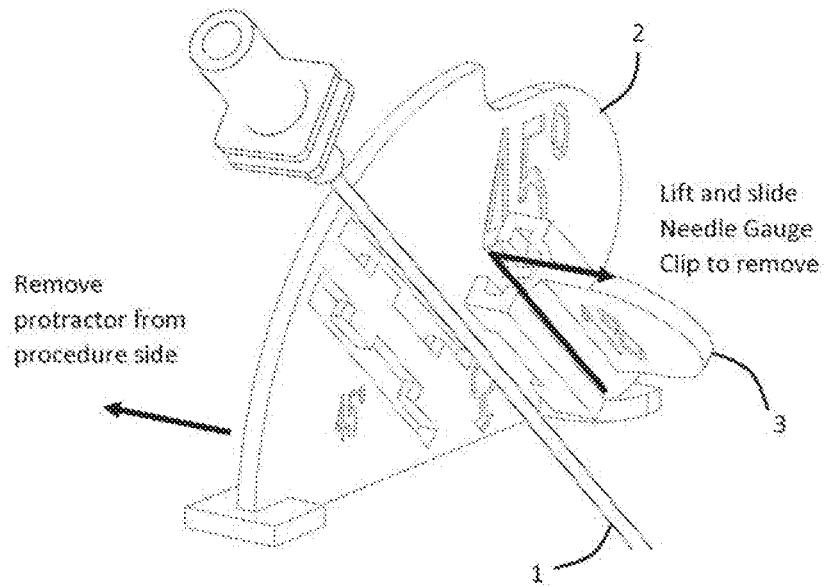
FIG. 27 illustrates the removal of the needle guide of FIG. 26 from the needle.

5. The rule process is then undertaken to shift the gamma mark to the correct "new" position as found in the depth chart in Step 3 above. The needle guide body is then aligned with the marking guide 4 to the side in which the needle 1 is to be inserted as shown in FIG. 24. A key design feature for this step is that the protractor guide marking strip 5 aligns the needle 1 to the central plane of the US probe 6.
6. The final step is to undertake the needling procedure. The needle 1 is inserted until the needle sterile mark lines up with the top of the needle guide 2 as show in FIG. 26.
7. If desired, the protractor guide can be removed leaving the needle 1 in place by sliding the Needle Gauge clip 3 up as shown in FIG. 27.

Centre Line Fixed Angle (CLFA) System—"Line and Dot" System

The "Line and Dot" Protractor system utilises the line dot marking guide 4 shown in FIG. 20 and, in this example, the needle guide 2 shown in FIG. 25.

Figure 28:
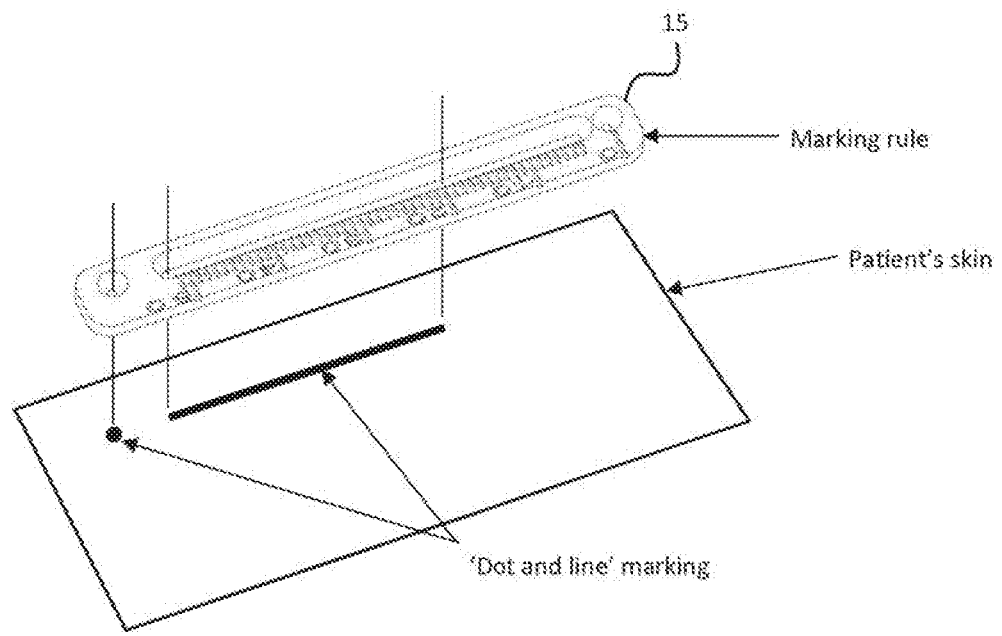
FIG. 28 illustrates a marking rule and mark made on patient's skin in the Centre Line Fixed Angle System.
Figure 29:
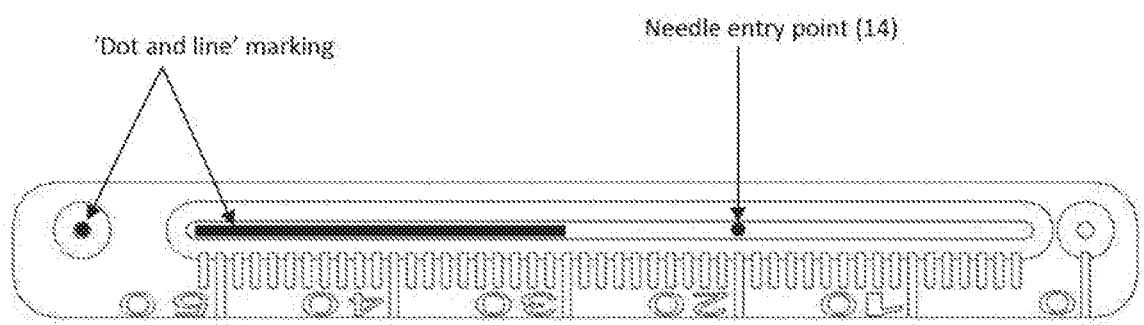
FIG. 29 is a top view of a marking rule and illustrates the positioning of marks made when the marking rule is utilised in a Centre Line Fixed Angle System.

This system is used as follows:
1. The pre-scan and skin marking processes are undertaken in the same way as described above but using the "line & dot" marking guide 4 shown in FIG. 20. The marking rule 15 is then used to locate the needle entry point 14. The rule is aligned with the skin 'dot and line' (drawn using the Marking Guide Body), with the dot being placed into the hole closest to the 50 mm mark. Using the depth chart for a chosen angle, a needle entry point 14 can then be read and marked on the skin using the rule and a different colour marker pen as shown in FIGS. 28 and 29.
2. The Needle Gauge clip 3 of the appropriate gauge is chosen (to suit the needle 1 to be used) and the needle 1 is inserted to the Needle Guide body which is then lined up with the straight skin marker line (done using the marking bracket attached to the US probe). The Needle Guide Body is then shifted along the straight skin marker line until the needle tip is in line with the 'needle entry point' 14 (shown in FIG. 29). This is shown diagrammatically in FIG. 25
3. The final step is to undertake the needling procedure. An introducer-needle may be used to make a hole in skin at the needle entry point 14. The needle 1 is inserted until the needle sterile mark lines up with the top of the needle guide 2 (or a feature in the needle guide body) as in the procedures described above.
4. If desired, the protractor guide can be removed leaving the needle 1 in place by sliding the Needle Gauge clip 3 up as for the gamma guide (see FIG. 27).

Variable Angle and Depth (VAD) System

Figure 30:
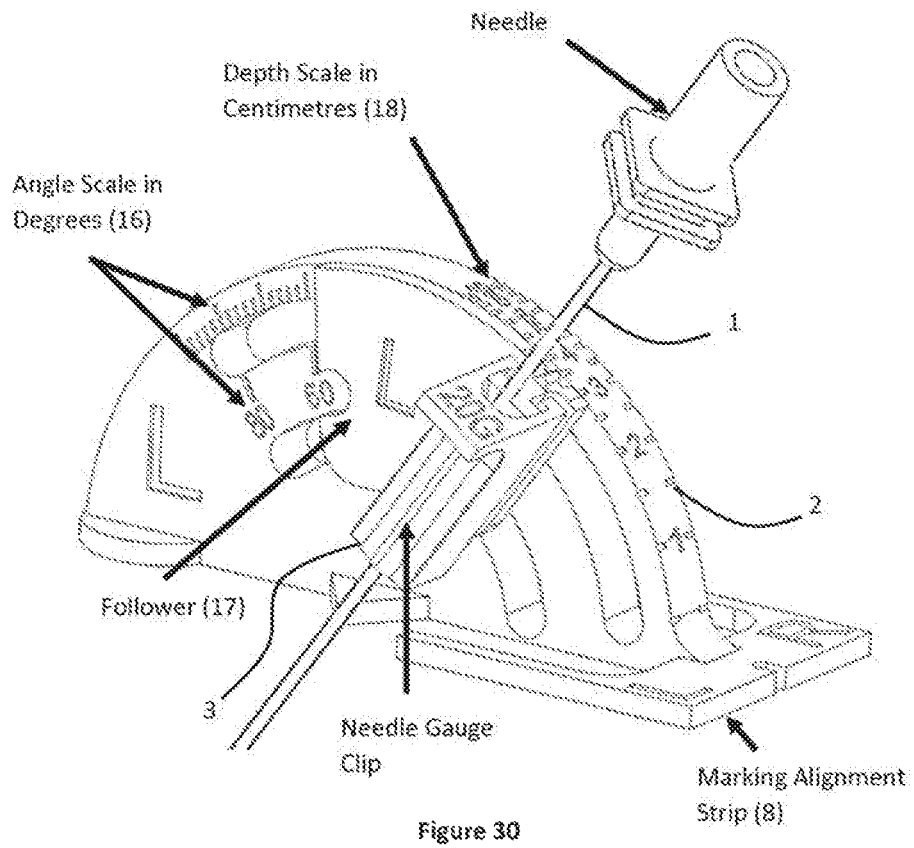
FIG. 30 is a perspective view of a needle guide in a left handed configuration which may be utilised in a needle guide system or method of the present invention with a needle positioned within the guide.
Figure 31:
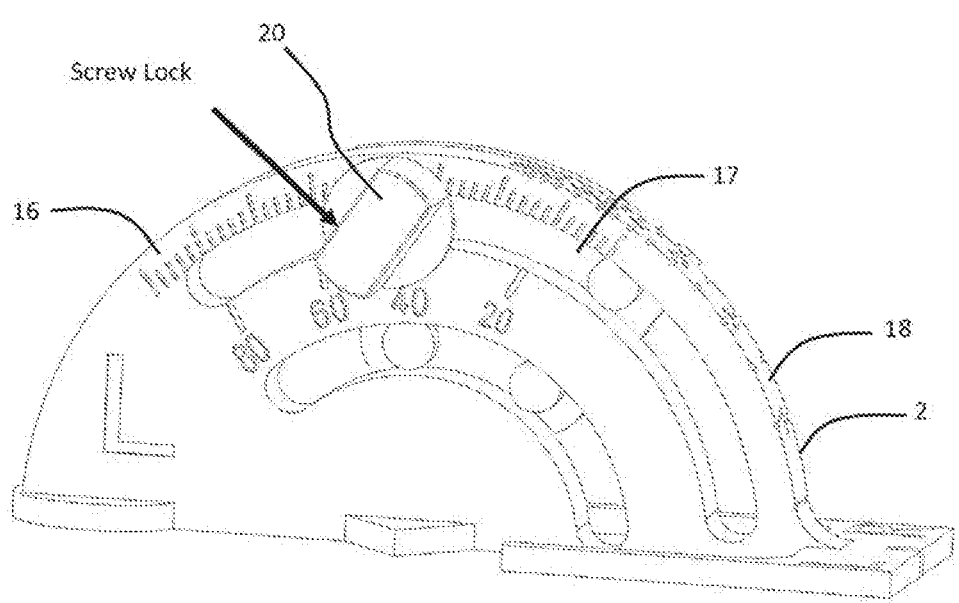
FIG. 31 is a perspective view of a needle guide in a right handed configuration which may be utilised in a needle guide system or method of the present invention with a needle positioned within the guide.

A Variable Angle and Depth (VAD) system has been developed as shown in FIGS. 30 and 31. This allows a single pre-scan needle guide 2 to be used to reach targets at different depths and also for different insertion angles. As seen most clearly in FIG. 31, follower 17 pegs run on tracks on the VAD body. A key feature is that these tracks have a projected centre of curvature at the point where the needle 1 is required to enter the skin. The follower 17 has a number of locating pegs (typically 3 or 4) which provide a stable and smooth movement along the tracks (A single track with just two locating pegs can also be used). The depth scale 18 is marked on the top of the device, and the angular scale 16 is marked on both faces, making it symmetrical.

Figure 32:
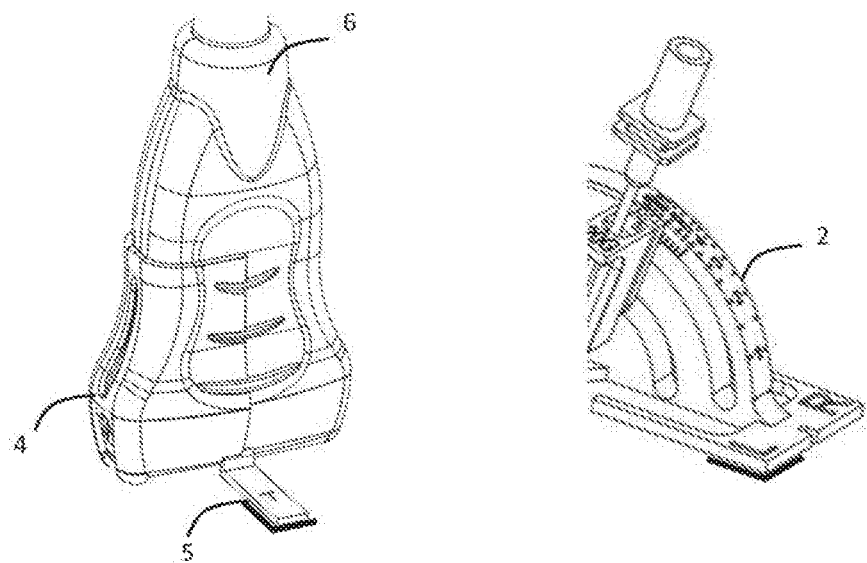
FIG. 32 illustrates the position of a mark in relation to the surface marking guide and needle guide in a needle guide system, the surface marking guide being attached to an ultrasound probe.
Figure 33:
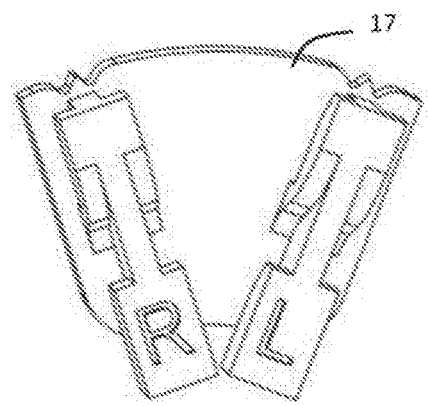
FIG. 33 illustrates a follower with two needle clips for right or left handed use.
Figure 34A:
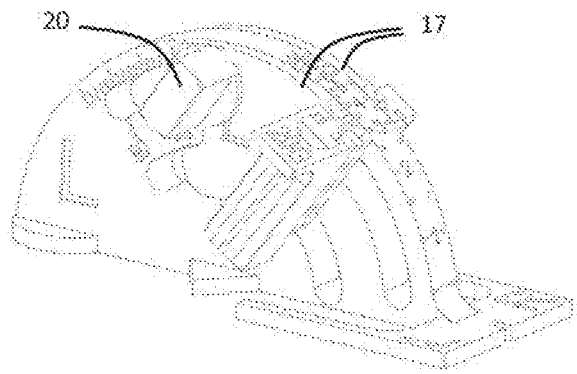
FIG. 34a is a perspective view of a needle guide which may be utilised left or right handedly in a needle guide system or method of the present invention with a needle positioned within the guide.

Key features of this design include:
1. The symmetry in the design allows it to be used easily for left of right handed use.
2. The needle guide 2 can be used for both transverse and longitudinal applications as discussed previously.
3. The needle guide 2 can be used at constant position with respect to the US probe centre axis, for either L or T marking, i.e. allowing the same guide (with the same depth scale marking) to reach any measured depth in L and T marking procedures. This necessitates the "Gamma" marks to be at the same position with respect to the probe axis for both L and T markings. Thus, the strips on the marking guide body will be of different lengths to compensate for the difference between the long axis and short axis thicknesses of the probe footprint (as discussed above with reference to FIG. 23).
4. The device can be locked into the correct position. A typical example of screw lock 20 is shown in FIG. 31.
5. The VAD needle guide 2 can be used to insert the needle 1 at any desired angle, as preferred by the clinician, to reach any depth by shifting the guide, instead of fixed angles provided by the aforementioned Centre Line Fixed Angle systems. If it is desired that the needle 1 reaches a target on the centre-line of the US probe 6, the user measures the depth of the target then selects the desired insertion angle, and uses embedded software, or the aid of a hand-held device, to obtain the guide shift distance, as described previously for the Centre Line Fixed Angle systems.
6. This design has a dual graduated scale; one scale 18 for the target depth (on the US probe centre line 10) and another 16 for the needle insertion angle with respect to the skin. This gives the clinician the choice of entering at a chosen angle, or reaching a target depth independent of angle. If it is desired to know the needle insertion length, a Depth Chart (similar to Table 2), or embedded software displaying such information on the US monitor, electronic information on held hand devices (e.g. smart phones or tablets), can be used.
7. The marking alignment strip is aligned to the "gamma" mark as shown in FIG. 32. A different alignment method, using an optical system (as mentioned previously) can also be used.
8. The needle 1 can be released by removing the needle clip from the VAD body (in the same manner as shown in FIG. 27) to allow the clinician to continue with the procedure without the guide if desired.
9. Variations of the needle follower 17 design are possible. FIGS. 30 and 31 show one variant in which there is a follower 17 with a single needle clip for right-handed use. A mirror image of this follower 17 can be used on the other side of the guide body for left-handed use. FIG. 33 shows a variant where the same follower 17 can be used for either left-handed or right-handed use (the follower 17 being mounted on one or other side of the guide body depending on which handed use is desired). FIG. 34*a* shows a third variant in which left-hand and right-hand needle followers 17 are mounted either side of the guide body. The two followers can fit together using a screw mechanism for example; the screw 20 fits through a straight hole on the follower 17 on one side and into a threaded hole on the follower 17 on the other side; this holds the two followers together and can also be used to lock the followers at the desired angular or depth position. In such arrangements, alternative or additional marking can be provided on the needle followers to indicate the side of the needle guide 2 they are intended to be mounted on.

Figure 34B:
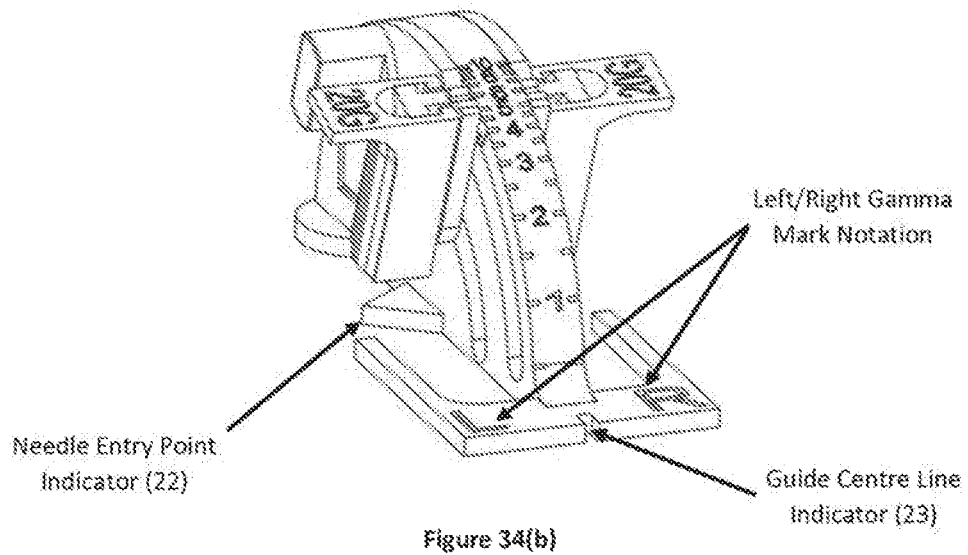
FIG. 34b is a perspective view of a needle guide which may be utilised left or right handedly in a needle guide system or method of the present invention with a needle positioned within the guide.
Figure 35:
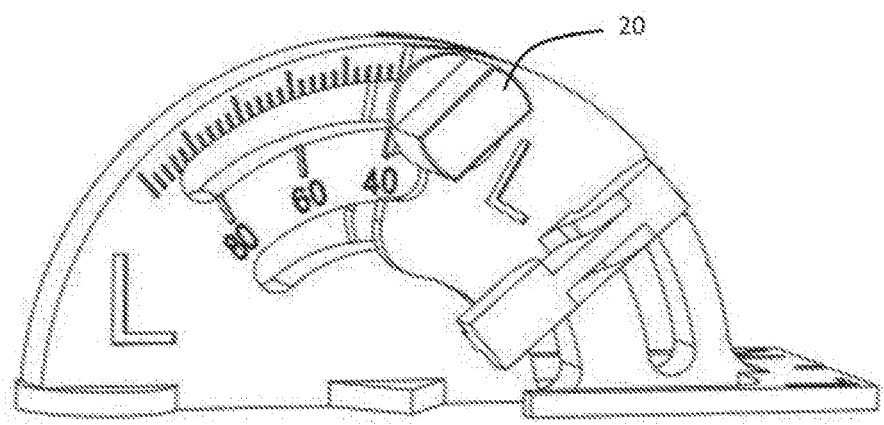
FIG. 35 is a perspective view of a needle guide which may be utilised left or right handedly in a needle guide system or method of the present invention with a needle positioned within the guide.

FIGS. 34*b* and 35 illustrate further optional features that could be incorporated in the VAD system for ease of use, including:

(a) A Guide Centre Line Indicator 23 which allows for a mark to be made at the centre line of the VAD guide if required (shown in FIG. 34*b*).
(b) Left and Right labels are added to the Marking Alignment Strip to reduce any possible confusion (shown in FIG. 34*b*).
(c) The third addition is a triangular indicator 22 which points to the needle entry point 14 on the skin (shown in FIG. 34*b*).
(d) To improve the visibility of the angles on the angular scale 16, and to improve the ease with which they are read, a notch is added to the follower 17, and the angle numbers moved accordingly so that they sit centrally within the notch (shown in FIG. 35).

Epidural Needle Guidance System

Ultrasound guidance is used for the Spinal or Epidural or Combined Spinal epidural anaesthesia to assess the level of vertebra, needle entry direction/path and depth of dura-ligamentum flavum complex. The needle entry point is normally along the midline axis of the US Probe 6 and thus causes difficulties to the clinician in inserting a needle 1 at the correct point and with the correct orientation in real time ultrasound guidance. Also, the Key and the Protractor Needle Guides 2, discussed above may be too restrictive and demand more setting up, so an Epidural Needle Guidance System has been developed to assist with such procedural requirements. The key design feature of the epidural pre-scan system is that the centre of curvature of the needle guide 2 is at the mid-point of the US probe 6 and thus the needle entry point 14. Ideally the needle 1 should follow a chosen path determined during pre-scanning. This requires the pose of the probe 6 to be measured as well as locating the entry point 14. The needle insertion depth can also be determined.

Although it is called the Epidural System, this pre-puncture ultrasound needle guide could be used with any other procedure using a curvilinear or linear probe 6, for example Spinal or Combined Spinal Epidural or liver biopsy or abscess drainage among others.

Epidural procedures normally use a Curvilinear Ultra-sound Probe rather than a Linear Probe; therefore, for demonstration of the principle, an exemplary guide system has been designed to fit a GE Curvilinear Probe 4C. However, the proposed guide systems can be designed to fit any type of ultrasound probes. The Epidural Needle Guidance System and typical epidural process are described below.

It should be noted that there are medical interventions which can be performed using a rotation (tilt) of the probe 6 in just the transverse plane (Single Axis Method), and other interventions, as described later, when for example the vertebra is rotated in the transverse plane, meaning that the optimum pose of the probe necessitate a rotation in the transverse plane as well as in the sagittal plane (Dual Axis Method). The procedure requiring just one angle of rotation/tilt (the Single Axis Method) is described first.

Process (Single Axis Method)

Figure 36A:
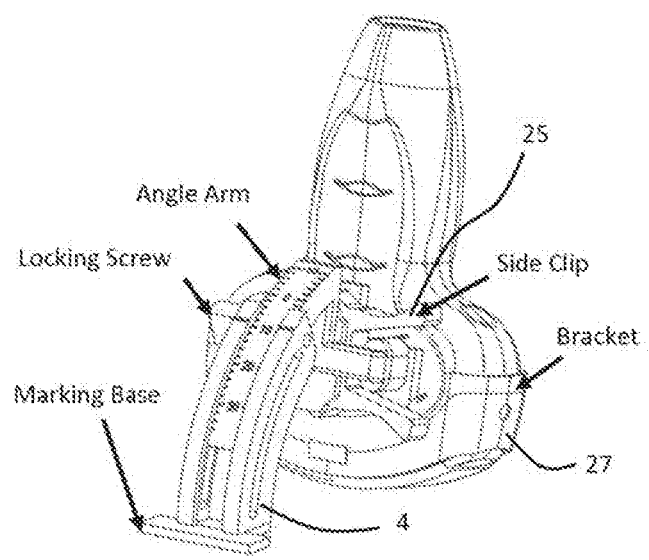
FIG. 36a illustrates an example surface marking guide which may be utilised in the present invention attached to an ultrasound probe.

A typical system is shown in FIG. 36*a*. Using this system the scan is first undertaken with the bracket 27 attached but without the marking guide 4 (i.e. without the angle arm attachment and marking base). This gives the clinician the ability/freedom to rotate/maneuver the probe 6 through a large angular range while performing transverse or longitudinal scans. The marking guide 4 is then attached to the bracket and the procedure is completed as described below. If required, the marking guide 4 can also be removed and re-inserted as and when desired.

The use of a removable Marking Guide System is preferable, compared to a system with the angle arm permanently fixed to the bracket, to give the clinician maximum freedom in the manipulation of the probe 6 during the pre-scan.

Different alternative attachment methods are shown in FIGS. 36*a* and 37, FIGS. 40 and 41, FIGS. 44 and 45, and FIGS. 46 and 47.

Figure 36B:
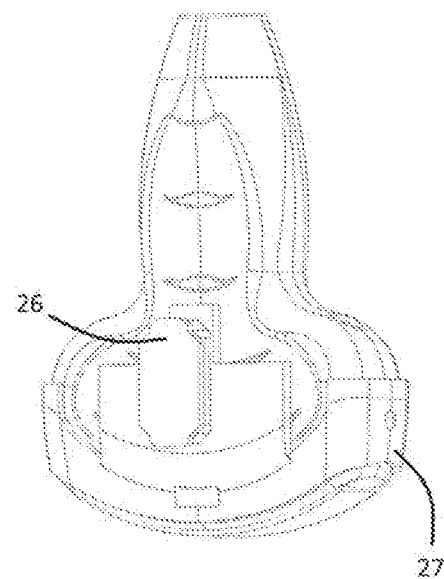
FIG. 36b illustrates an ultrasound probe with a bracket of a surface marking guide fitted.
Figure 38:
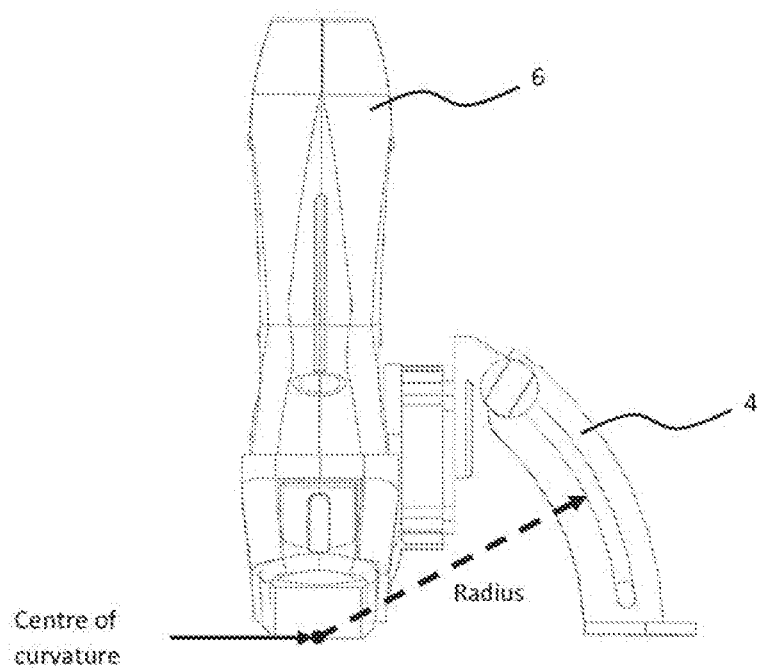
FIG. 38 is a side view of the surface marking guide and ultrasound probe of FIGS. 36a and 37.
Figure 39:
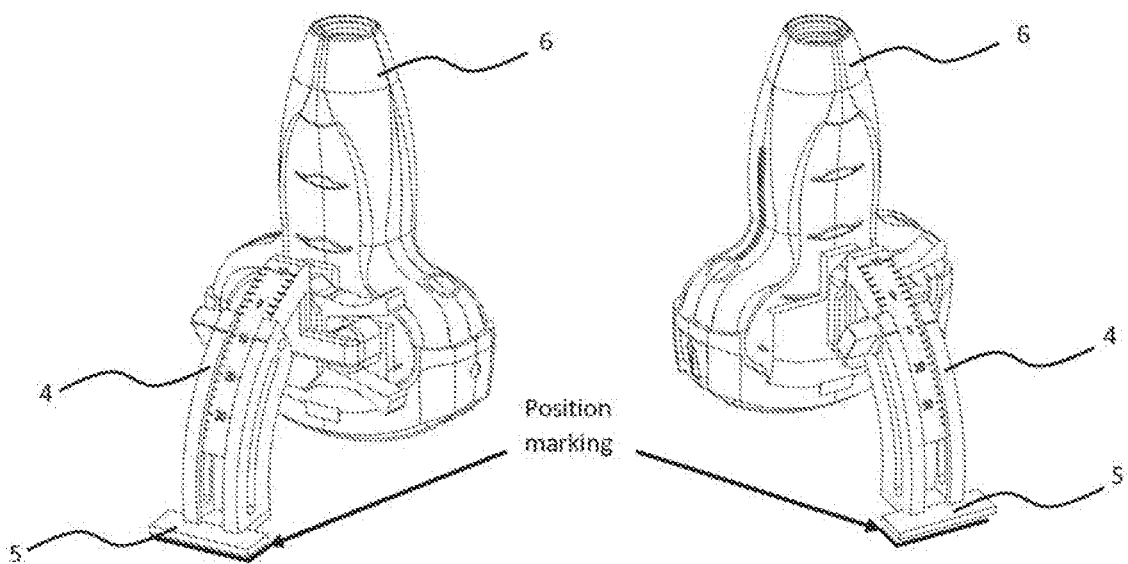
FIG. 39 shows two views of an example surface marking guide which may be utilised in the present invention attached to an ultrasound probe.
Figure 42:
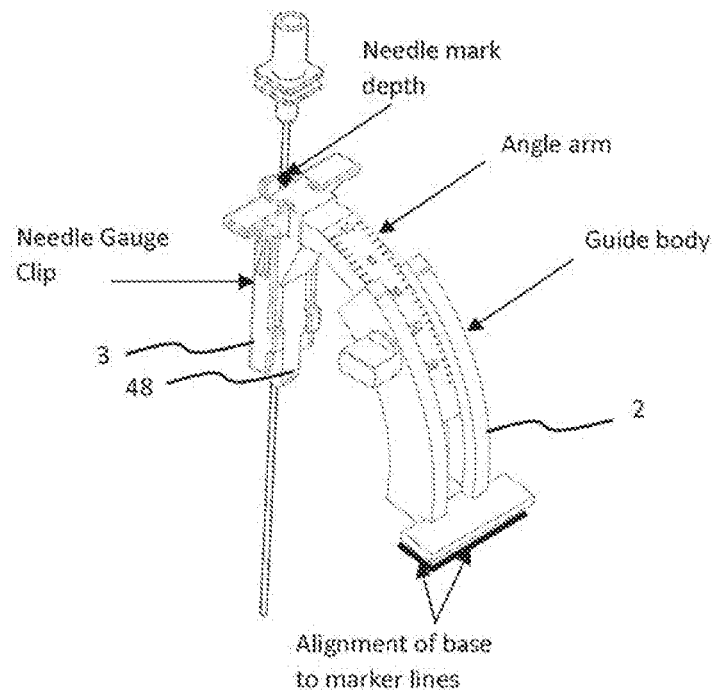
FIG. 42 illustrates a Variable Angle and Depth needle guide which may be utilised in a needle guide system or method of the present invention having a needle inserted in the guide.

1. The bracket 27 of the Epidural Angle Marking Guide 4 is fitted first to (or attached to) the US probe 6 as shown in FIG. 36*b* (note that the profile of the marking base may change, and also a different attachment method of the Epidural Angle Marking Guide 4 to the US probe 6 may be used).
2. A key design feature of this epidural pre-puncture system is that the centre of curvature of the needle guide 2 (shown in FIG. 42), and thus the needle entry point 14, are at the mid-point of the US probe 6 (shown in FIG. 38).
3. A longitudinal pre-scan is undertaken in the paramedian or juxtamedian plane at the position and angle required to avoid spinous processes i.e. to visualize the ligamentum flavum—dura complex through interspinous space or interlaminar space. Subsequently a transverse scan is performed to confirm the needle entry point and needle trajectory for midline or paramedian procedure. The Angle Arm is then attached to the bracket, and with the marking base in contact with the skin the Angle Arm is locked in position (using a locking screw, as shown, or other locking means). It should be noted that the Angle Arm can be fitted before the pre-scan is carried out. It could also feature a spring mechanism that fits inside the Angle Arm body and ensures that the marking base remains in contact with the skin at all times.
4. The insertion length to the epidural space (with respect to skin) is recorded from the US scan screen.
5. A marker is then used to mark (or deposit a "transferable mark sticker") on the skin the location of the position of the Angle Marking Guide 4 as shown in FIG. 39. The position marking can be made on either the left or right hand side of the Angle Marking Guide, as desired by the user, as shown in FIG. 39. An optical (e.g. laser or light pointer) mechanism can also be used to assist in marking the skin and providing the angular pose of the probe.
6. The probe 6, with the Marking Guide attached, is moved away from the patient and the angular measurement is read and recorded.
7. The US probe 6 and Marking Guide 4 are put aside.
8. The marking on the skin may be covered by a sterile transparent tape (so that it does not rub off when the skin is cleaned). The skin is disinfected using the appropriate technique.
9. If desired, the insertion length is then marked onto the needle 1 as described above.
10. A sterile Needle guide 2, shown in FIG. 42, is picked up.
11. The Angle Arm of the sterile Needle guide 2 is locked at the angle recorded in Step 6 (shown in FIG. 42).
12. A sterile Needle Gauge clip 3 of the required gauge (to suit the needle 1 or to suit the Introducer Needle if used) is chosen and fixed to the Angle Arm (shown in FIG. 42).
13. The base is then aligned with the pre-drawn marks on the skin to the edge of the base of the needle guide 2, as shown in FIG. 42.
14. The needle 1 can then be inserted into the funneled guide of the Needle Gauge clip 3, as shown in FIG. 42. If the needle insertion length is marked on the needle 1, the needle 1 is inserted to near the depth marker, and a standard technique as per the operator's preference, e.g.

Loss of resistance is carried out for placing the needle 1 in its final position in order to complete the epidural.

Figure 43:
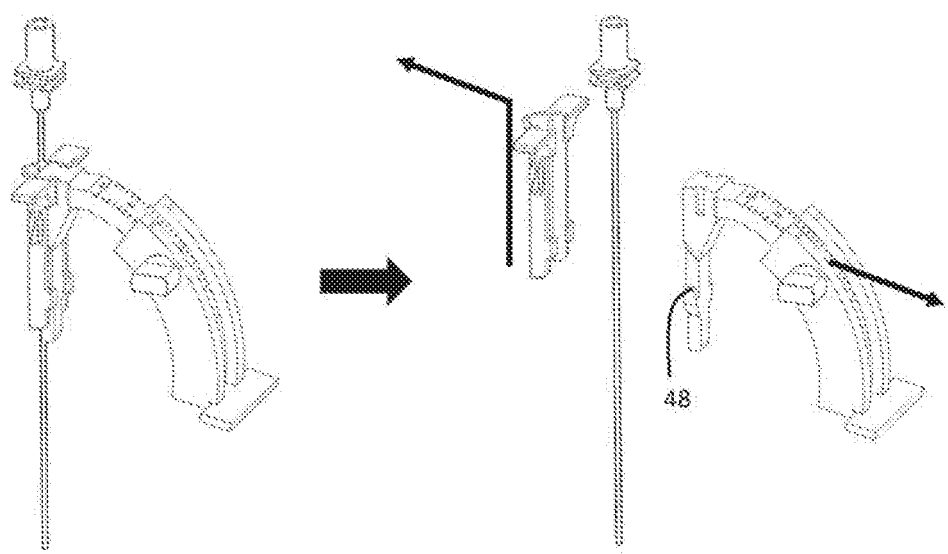
FIG. 43 illustrates the removal of the needle guide of FIG. 42 from the needle.

15. If required, the Needle Gauge clip 3 can be easily removed allowing the Needle guide 2 to be removed, leaving the needle 1 in place and free to be manipulated by the clinician, as shown in FIG. 43.

It should be noted that instead of transferring the angular position, read from the marking guide 4, to a sterile needle guide 2 (as per Steps 6 and 11), the non-sterile pre-scan Angle Arm (locked as describe in Step 3) can be detached from the bracket 27 and placed in an appropriate sterile cover. A needle channel 48, for example similar to the one shown as integral part of the needle guide 2 (FIG. 42), but designed with, for example, a mounting interface 26 can be attached through the sterile cover to the locked pre-scan Angle Arm. This will increase the accuracy and eliminate any potential mistakes during in the reading and transfer of the tilt angle measurement.

It should also be noted the VAD needle guide 2 (shown in FIGS. 30 to 35) can also be used here. However, the alignment gamma marking may be shifted to align the needle axis to be along the centre line 10 of the US probe.

Alternative Angle Arm Attachments

Figure 37:
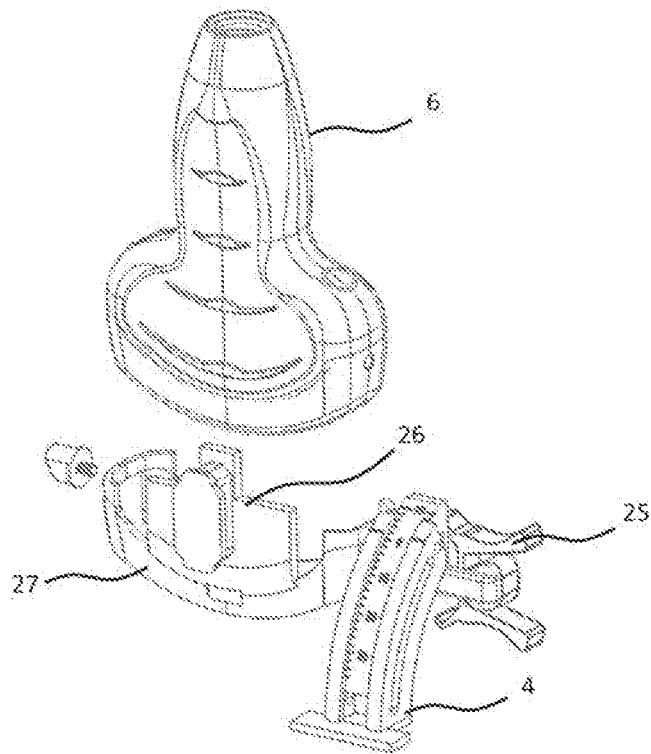
Figure 40A:
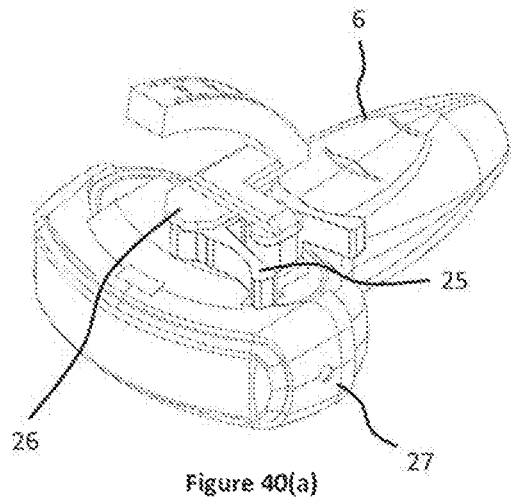
FIG. 40a illustrates a surface marking guide attached to an ultrasound probe.
Figure 40B:
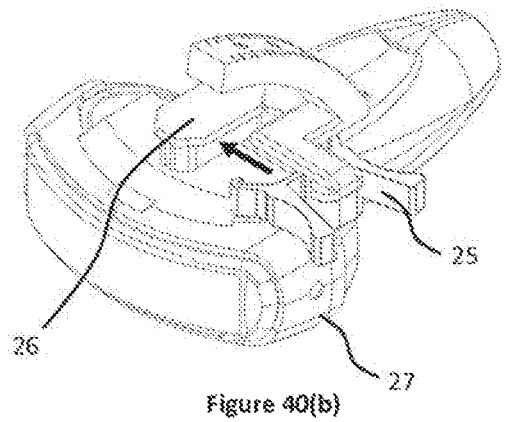
FIG. 40b illustrates attaching of the marking guide of FIG. 40a to a bracket on the ultrasound probe.
Figure 41A:
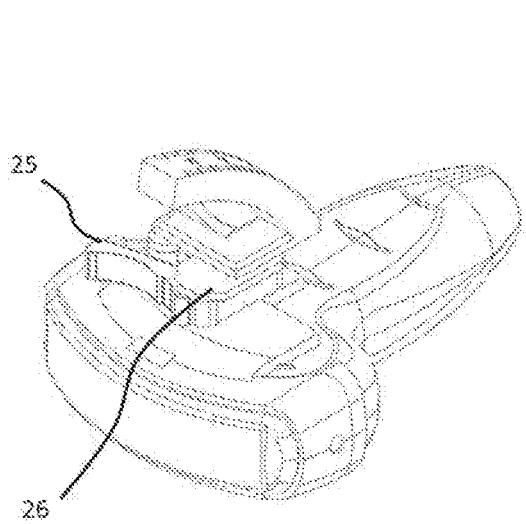
FIG. 41a illustrates a surface marking guide attached to an ultrasound probe.
Figure 41B:
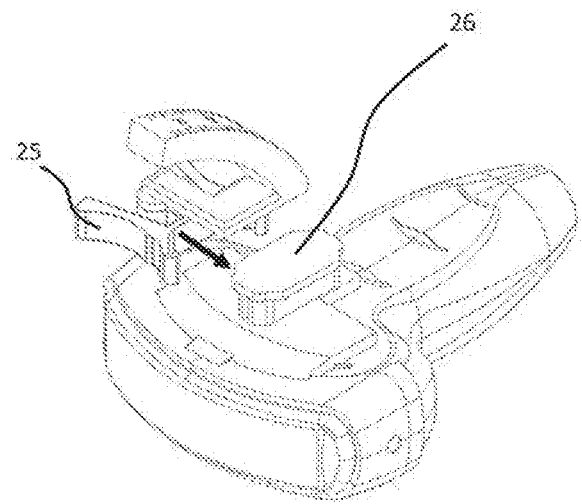
FIG. 41b illustrates attaching of the marking guide of FIG. 41a to the bracket on the ultrasound probe.

There can be different mechanisms for attaching the removable marking guide 4 to the bracket. One such mechanism is shown in FIGS. 36 and 37, and the manner in which it is attached and removed is shown in FIGS. 40 and 41. Two other such mechanisms are shown in FIG. 44 and FIG. 46, and the manners in which they are removed are shown in FIG. 45 and FIG. 47 respectively.

FIG. 37 shows an exploded view of the single axis epidural system shown in FIG. 36. In this example the Angle Arm is mounted onto the Bracket 27 by a clipping arrangement including a Mounting Interface 26 on the Bracket 27 and Clip 25 which is connected to the Angle Arm. The Mounting Interface 26 and Clip 25 have mating faces that locate the two components relative to one another. The Clip 25 has opposed clip portions that engage under opposite ends of the Mounting Interface 26 when the clip is pushed onto the mounting interface. By squeezing the Tabs together the jaws of the Clip 25 are spread apart. This allows the release of Clip 25 from the Mounting Interface 26 and can also be used to reduce the resistance to clip engagement. The Mounting Interface 26 has a wide Backing Plate; when the clip is engaged the side of the clip lies flush with the Backing Plate which adds stability to the connection. The Backing Plate extends out from both sides of the Mounting Interface 26 to allow for left hand or right hand designs of the clip to be used with the same bracket. The Backing Plate also helps locate the Clipping in the same plane as the Mounting Interface 26 during clip engagement.

Figure 44:
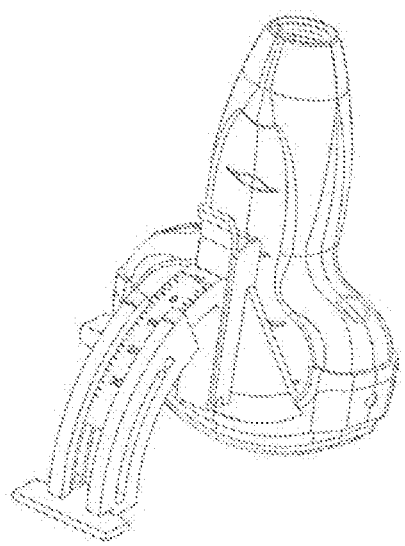
FIG. 44 illustrates a surface marking guide attached to an ultrasound probe.
Figure 45:
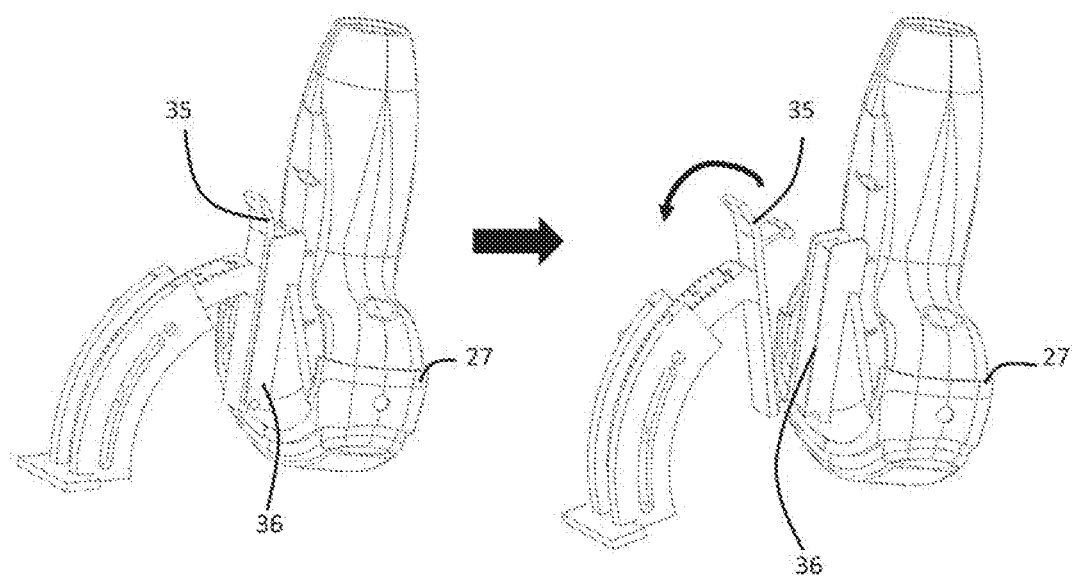
FIG. 45 illustrates removing the marking guide of FIG. 44 from a bracket on the ultrasound probe.

Alternate clipping mechanisms can also be used to connect the Angle Arm to the Bracket; one example mechanism is shown in FIGS. 44 and 45. The design features a pivot point at the bottom of the Mounting Interface 36. During clip engagement the pivot point mating features of the Clip 35 and Mounting Interface 36 are located. The Clip 35 is then rotated into the Mounting Interface 36 until the Clipping Point goes over the upper lip of the Mounting Interface 36 and the Clip is engaged. To release Clip 35, the Tab is pulled outwards as shown in FIG. 45; this lifts the Clipping Point over the upper lip of Mounting Interface 1 and allows Clip 35 to be removed.

Figure 46:
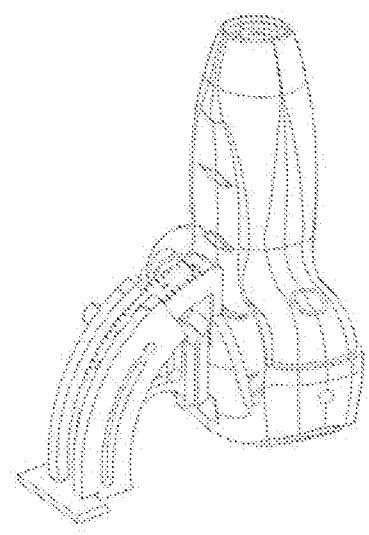
FIG. 46 illustrates a surface marking guide attached to an ultrasound probe.
Figure 47:
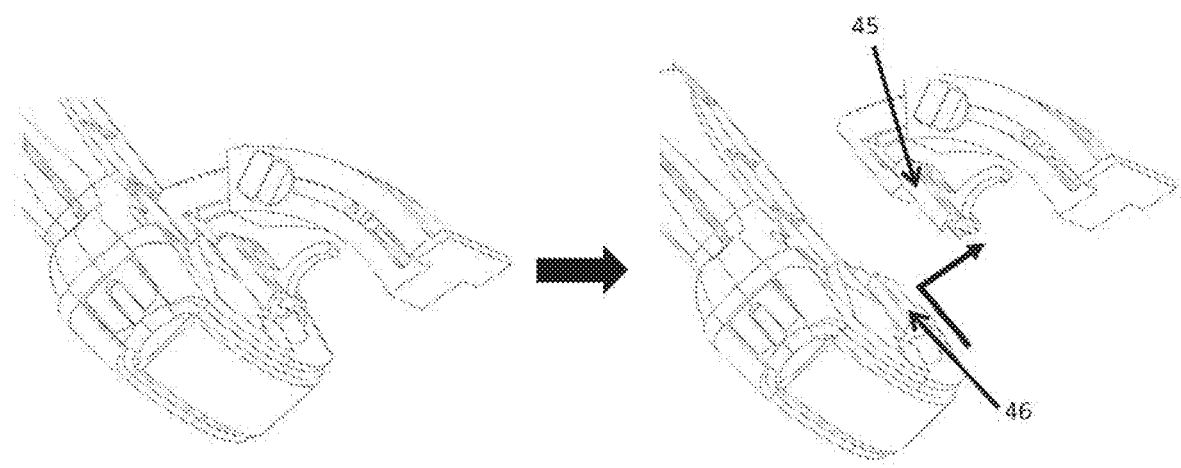
FIG. 47 illustrates removing the marking guide of FIG. 46 from a bracket on the ultrasound probe.

Another clipping mechanism is shown in FIGS. 46 and 47. Clip 45 has angled sides which the sides of the Mounting Interface 46 fit into. There is a Lip on Clip 45 which causes the clipping face to flex outwards as Clip 45 is pushed down into the Mounting Interface 46. Clip 45 is fully engaged when Lip extends over the bottom edge of the Mounting Interface 46 and locates Clip 45 vertically. Clip 45 is released by pulling Tab to lift the lip over the bottom edge of the Mounting Interface 46.

Different Length Angular Scale

These angular length scales on the guides can be designed at different lengths to allow clinicians to choose an angular range at which the system would work between, for example −15° to 25° or −5° to 35°. This increased choice of angular ranges would enable the system to be used in a wider array of applications, and also give greater freedom for epidural procedures, to account for variations of spinal curvature and deformity.

Epidural Needle Guidance for Vertebral Rotation

In scoliotic[1] patients, the vertebra can rotate/bend in the transverse plane, meaning that the optimum angle of insertion may be rotated in the transverse plane as well as the sagittal plane. This means that the angle measured in two planes will provide more information. A needle guide 2 for a scoliotic patient should then be able to record and fix the needle insertion pose in both the transverse and sagittal planes. Two methods, the "Double Axis—Pen system" and the Double Axis—Variable Base Angle system" of accomplishing this are describe below. It should be noted that both methods are equally valid for single axis procedures described above.

[1]Scoliosis: lateral (sideways) deviation of the backbone, caused by congenital or acquired abnormalities of the vertebrae, muscles, and nerves.

Double Axis Pen System

Figure 48:
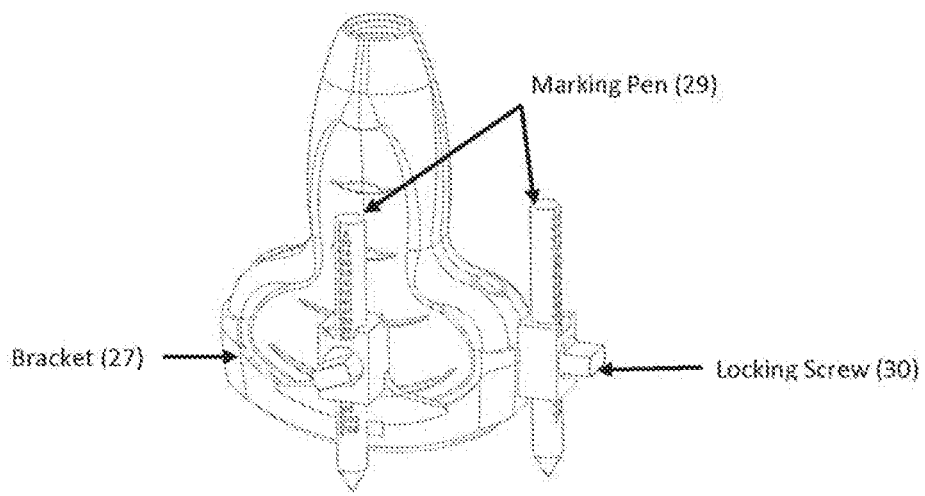
FIG. 48 is a perspective view of a surface marking guide according to the Marking Pen System attached to an ultrasound probe.
Figure 49:
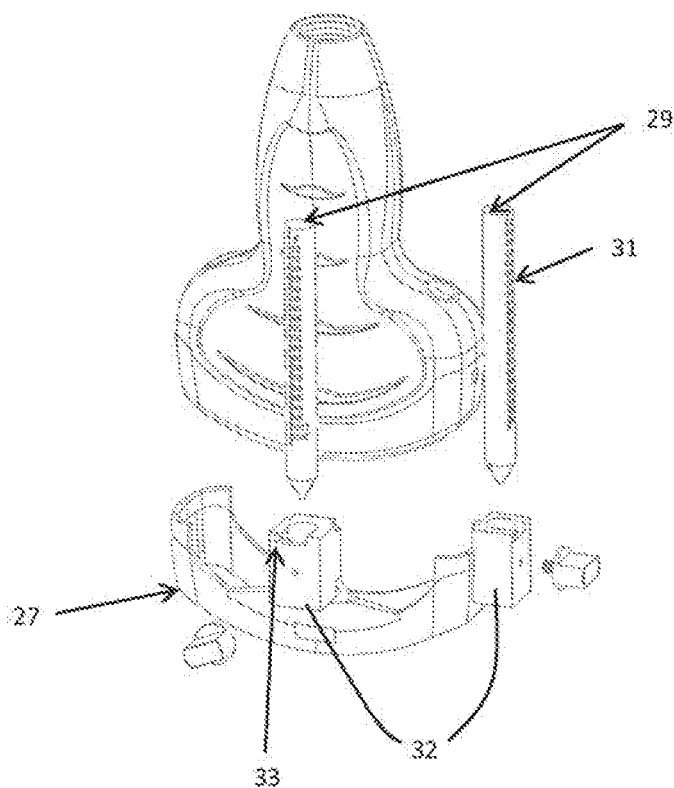
FIG. 49 is an exploded view of the surface marking guide and ultrasound probe of FIG. 48.
Figure 50A:
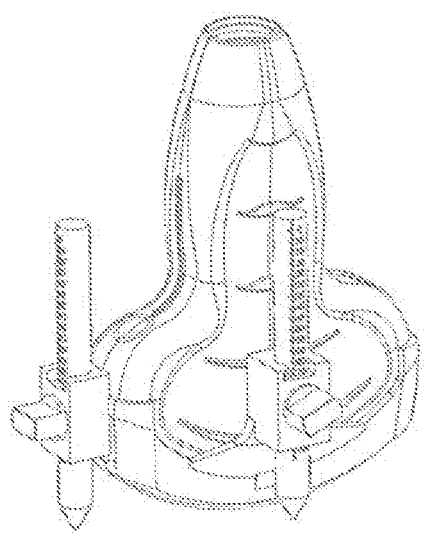
FIG. 50a is a perspective view of a left handed version of the surface marking guide and ultrasound probe of FIG. 48.
Figure 50B:
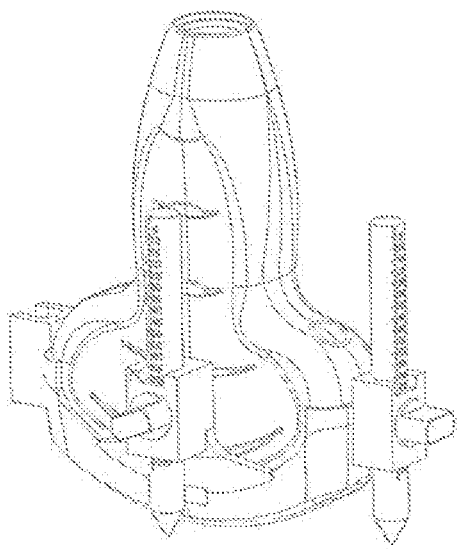
FIG. 50b is a perspective view of an alternative surface marking guide according to the Marking Pen System attached to an ultrasound probe in a right handed configuration.
Figure 50C:
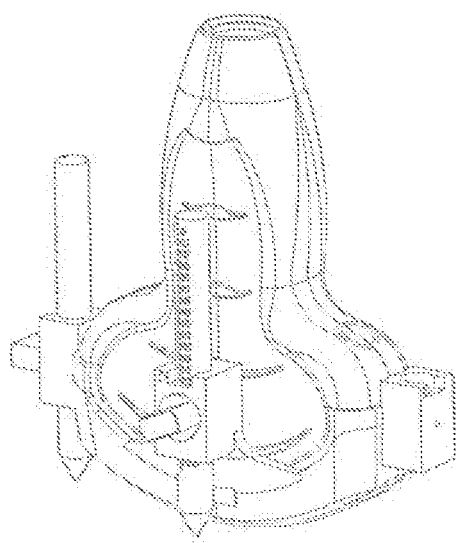
FIG. 50c is a perspective view of the surface marking guide and ultrasound probe of FIG. 50b in a left handed configuration.
Figure 51A:
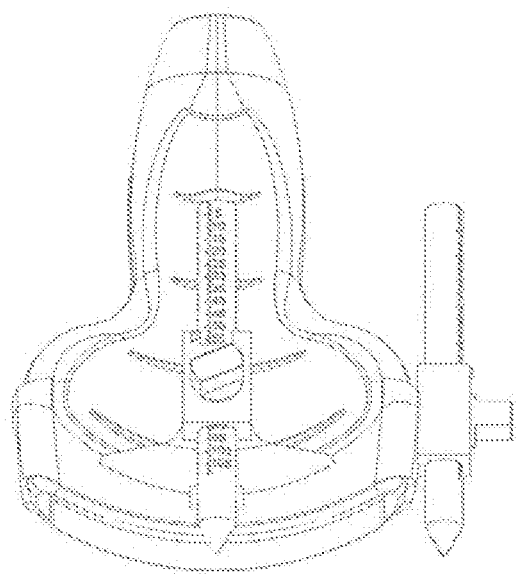
FIG. 51a shows an ultrasound probe and surface marking guide according to the Marking Pen System in a first orientation.
Figure 51B:
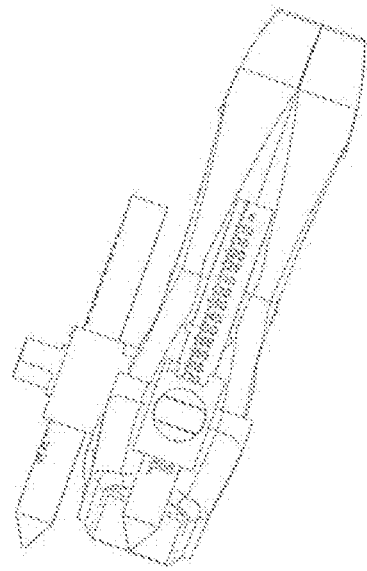
FIG. 51b shows an ultrasound probe and surface marking guide according to the Marking Pen System in a second orientation.
Figure 52A:
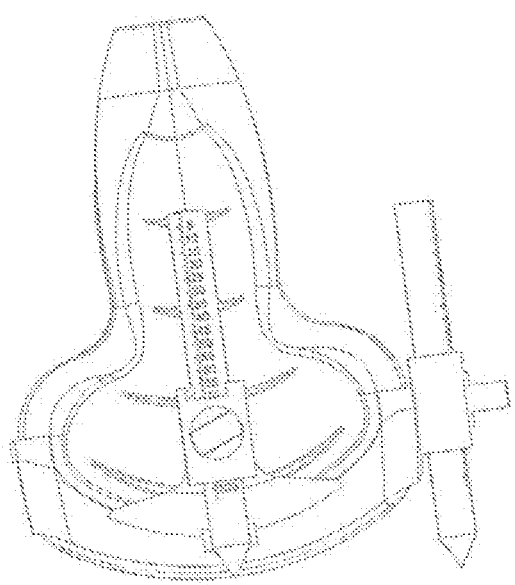
FIG. 52a shows an ultrasound probe and surface marking guide according to the Marking Pen System in a third orientation.
Figure 52B:
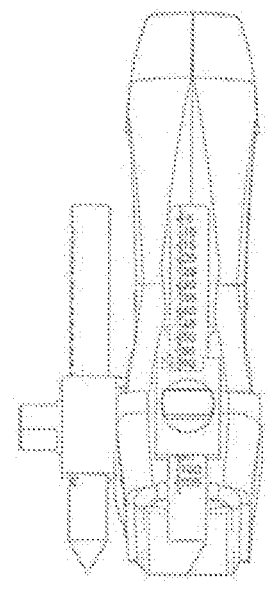
FIG. 52b shows an ultrasound probe and surface marking guide according to the Marking Pen System in a fourth orientation.
Figure 53A:
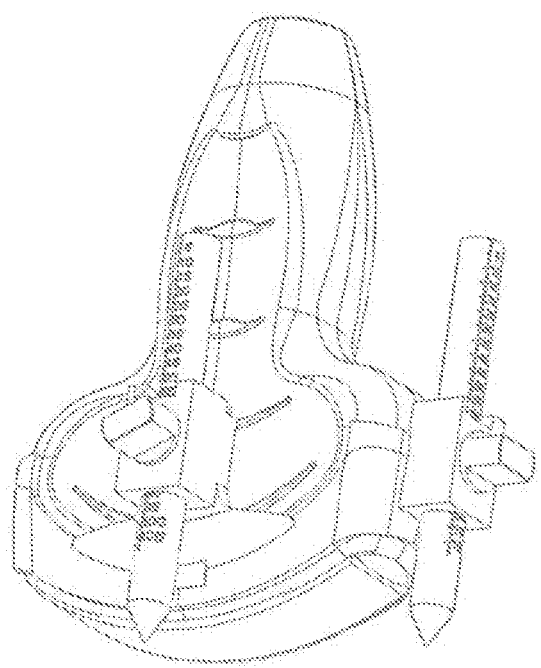
FIG. 53a shows an ultrasound probe and surface marking guide according to the Marking Pen System in a fifth orientation.
Figure 53B:
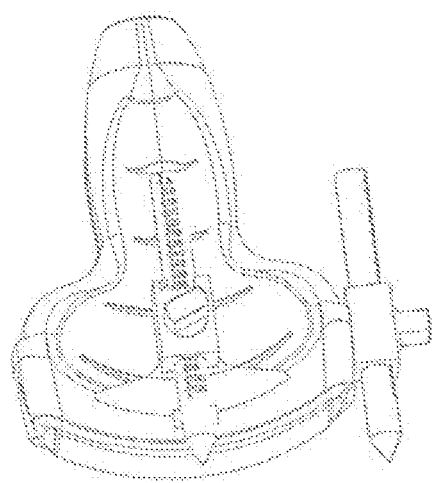
FIG. 53b shows an ultrasound probe and surface marking guide according to the Marking Pen System in a sixth orientation.
Figure 53C:
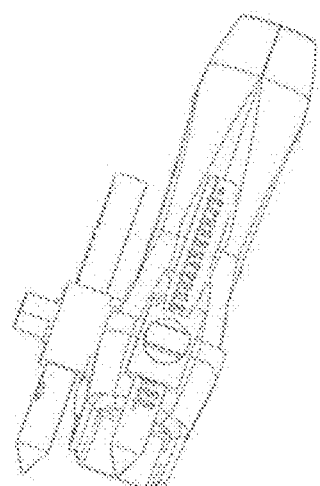
FIG. 53c shows an ultrasound probe and surface marking guide according to the Marking Pen System in a seventh orientation.
Figure 54:
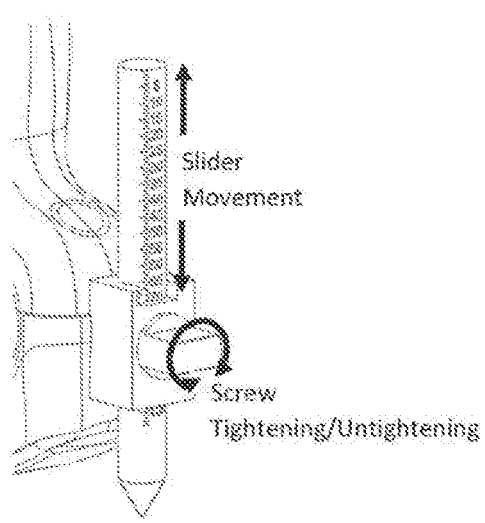
FIG. 54 illustrates the adjustment of a Marking Pen in a surface marking guide according to the Marking Pen System.
Figure 55:
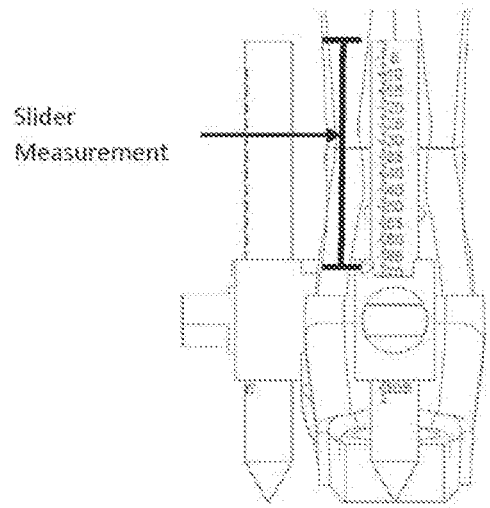
FIG. 55 is a side view of an ultrasound probe and surface marking guide according to the Marking Pen System.

The Marking Pen System, shown in FIGS. 48 and 49, uses a datum point (centre of US probe) and two reference points to set angles in both the transverse and sagittal planes. The example shown in FIGS. 48 and 49 is designed for a right handed user; this may be adapted for a left handed user by moving the transverse plane marker to the opposing side of the bracket as shown in FIG. 50(*a*). An alternate design which would be applicable to both left and right handed users would have a double sided bracket, as shown in FIGS. 50(*b*) and 50(*c*), and the user can choose which side to use as desired. The extension of the pens (also referred to as sliders) is used to define the pose of the probe 6, by locking them in position once pushed to touch the (and mark) the skin as shown in FIGS. 54 and 55. Different orientation scenarios are shown in FIGS. 51 to 53.

An exploded view of the Double Axis Pen System is shown in FIG. 49. The US Probe 6 clips onto to the Marking Bracket 27. Marking Pens 29 slide through the Bracket Marking Pen Housings 32 and can be locked in place by tightening Locking Screws (other locking methods may also be used). There is a Reference Mark 33 on Marking Pen Housing 32 which is used (in this example) to read off the extension of the Marking Pens 29 (also referred to as sliders) on Scale 31 (shown also in FIG. 55). Marking Pens 29 have inked tips to mark to skin. The two marks from the two Marking Pens 29, together with the extension of the Marking Pens (shown in FIG. 55), are used to locate the position of the US probe 6 on the skin of the patient, as well as determine the pose of the US probe 6 with respect to the skin. Additional pen housings (and thus pens) can be used at other locations on the bracket 27 to allow the user flexibility of where to place the pens and/or reduce the effect of skin compression on the measurement (through the pens' depths) of the pose of the probe.

It should be noted that instead reading off the pens' depth from Scales 31, such measurement could be provided automatically using pens with integral linear sensors. The depth position of each pen is then transferred to a screen via wires or wireless.

Another method is by replacing the marking pens 29 and pen housings 32 by optical (e.g. laser) pointers, fixed to the bracket 27, which can project a marking spots on the skin as well as measure the distance from each pointer to the skin. Such measurement can then be used for positioning the reference pens 34 of the Needle Insertion Guidance System (FIG. 56) as described below for the Pen System.

Figure 56:
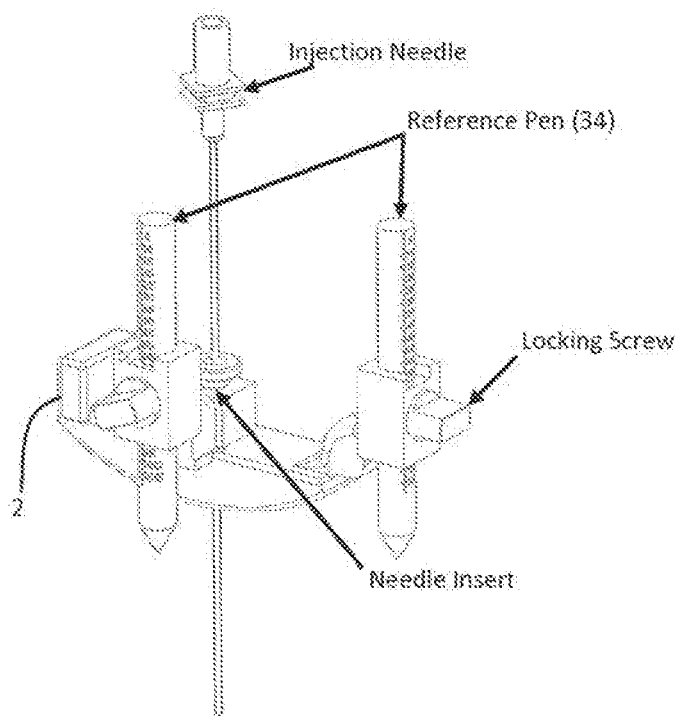
FIG. 56 is a perspective view of a Needle Insertion Guidance System with a needle positioned in the guide.
Figure 57A:
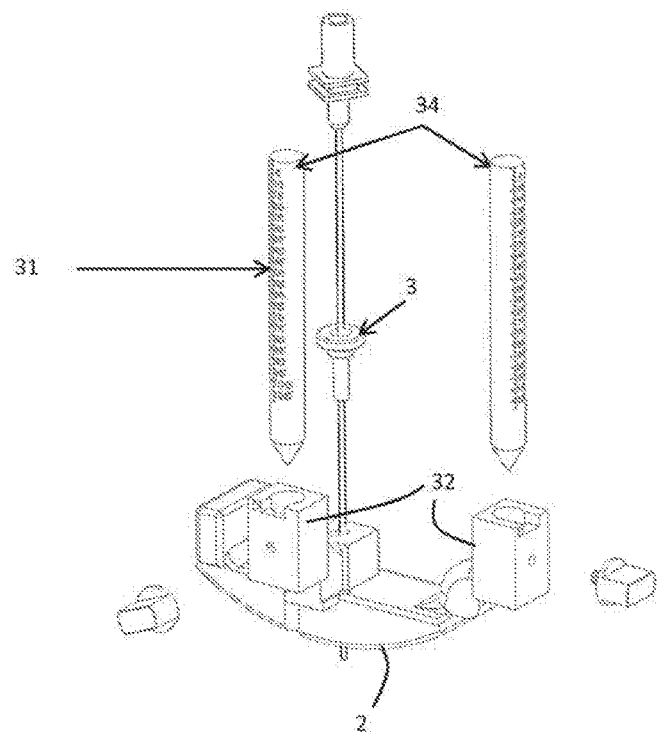
FIG. 57a is an exploded view of a Needle Insertion Guidance System with a needle positioned in the guide.

The Needle Insertion Guidance System is shown in FIG. 56, with the exploded view shown in FIG. 57*a*. The base of the Needle Guide Body 2 has the same curvature/shape as the base of the US probe 6 the Marking System is designed for. The Reference Pen Housings 32 (in FIG. 57*a*) have the same position and orientation with respect to the needle insertion axis and skin insertion point of the Needle Guide 2 (shown complete in FIG. 56) as the Marking Pen Housings 32 of Bracket 27 (in FIG. 49) are with respect to the US Probe axis and base centre. Thus, using the position of the two Marking Pens 29 (in FIG. 49) recorded during the pre-scan (as shown in FIG. 55), and positioning the sterile Reference Pens 34 (with dry tips), in FIG. 57*a* at the respective same depths in the Reference Pen Housings 32 of the sterile Needle Guide 2, the needle insertion trajectory will be the same as the central axis of the US probe 6 obtained during pre-scan when the tips of the Reference Markers are aligned with the two marks on the skin made (using the Marking Pens) during pre-scan.

Figure 57B:
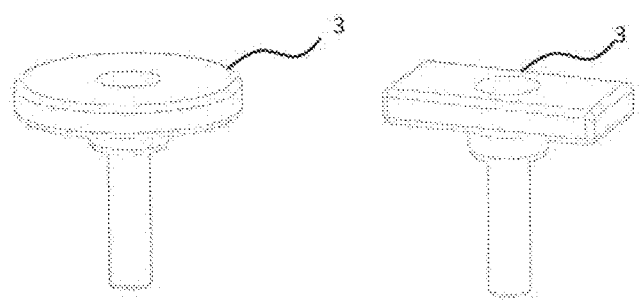
Figure 58A:
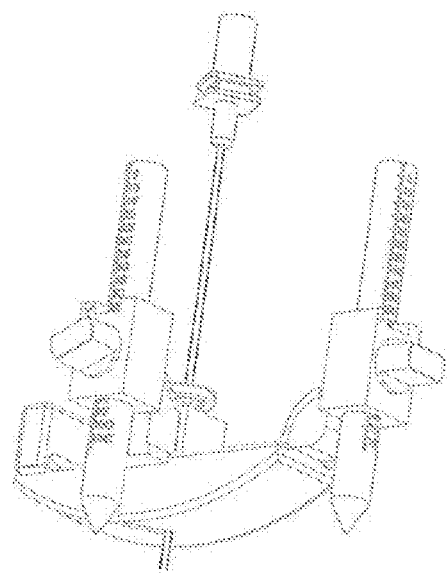
FIG. 58a is a perspective view of a Needle Insertion Guidance System with a needle positioned in the guide set at a certain orientation.
Figure 58B:
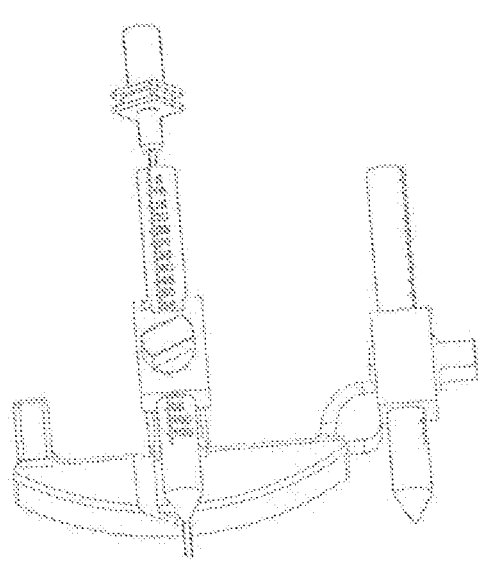
Figure 58C:
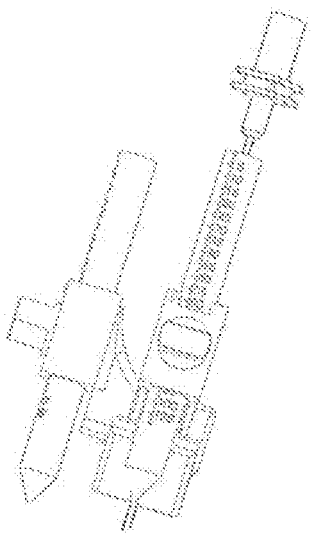

The Needle Insert 3 comes in varying sizes to accommodate different gauges of needle. The insert 3 used in this example is the same as described previously for the Key System, although other methods may be used to channel the needle 1. During the position of the Needle guide 2 and the insertion of the needle 1, the Needle guide 2 may be held between the added Lip and Reference Pen Housing 32 (in FIG. 57*a*) on the opposing side of the Guide. It should be noted that Needle Insert 3 may not have a small external cylindrical shape at the needle entry area; it may have a different shapes, for example, a large cylindrical shape or two rectangular lips as shown in FIG. 57*b*, to ease its removal (using two fingers). The needle insert may also have a slit, or composed of two halves to allow mounting it to needles which do not have a straight tip, e.g. Touhy tip.

It should be noted that, in order to ensure maximum accuracy, the force/pressure applied on the skin of the patient during the needle insertion procedure should be of a similar magnitude as the force/pressure exerted on the US probe 6 during pre-scan skin marking. More than 2 marking pens (and reference pens) may also be used to improve accuracy.

Process

Figure 59A:
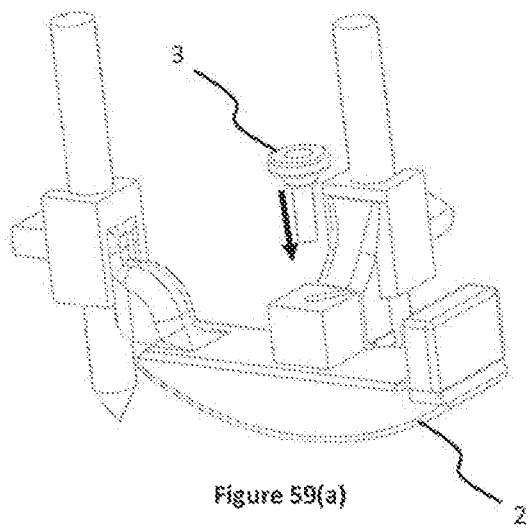
FIG. 59a illustrates the insertion of a needle insert into a Needle Insertion Guidance System.
Figure 59B:
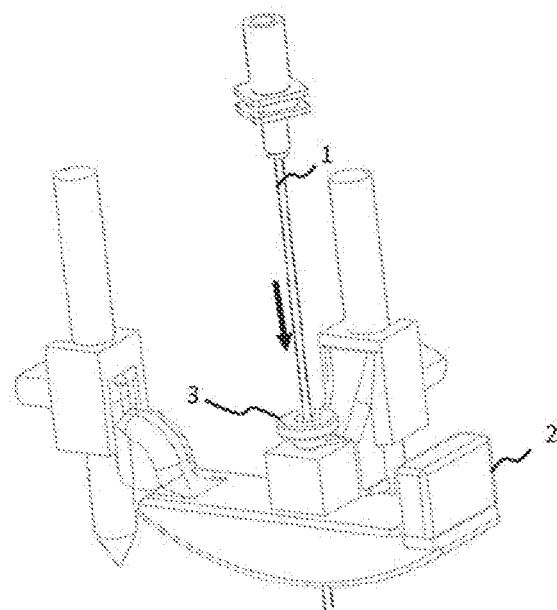
Figure 60A:
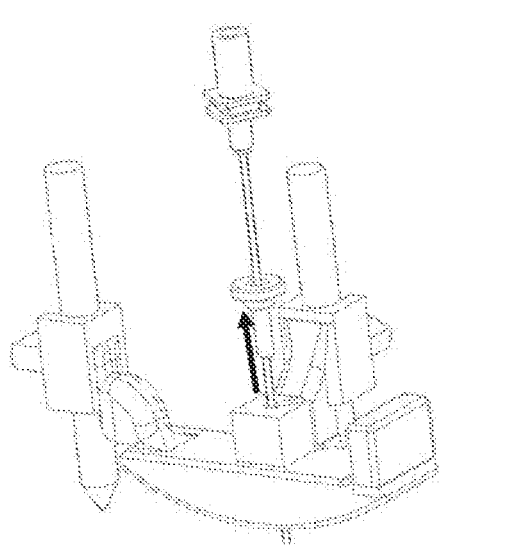
FIG. 60a illustrates the removal of the needle insert from the Needle Insertion Guidance System of FIG. 59b.
Figure 60B:
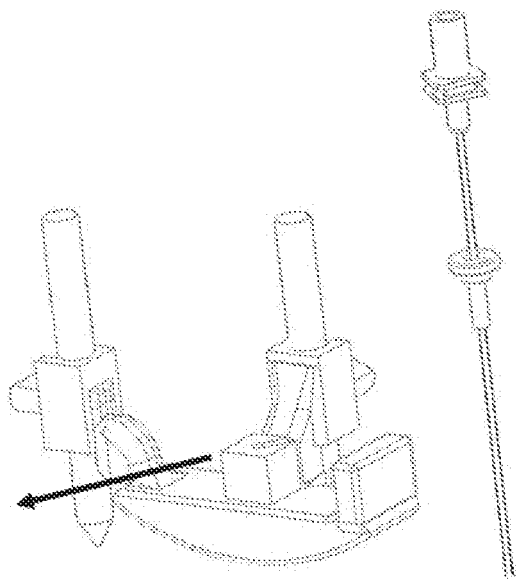
FIG. 60b illustrates the removal of the Needle Insertion Guidance System of FIG. 60a from the needle.

1. The clinician attaches the Marking Bracket 27 (FIG. 49) to the US probe 6 using the locating features of the Marking Bracket, and ensuring that the Marking Pens 29 (FIG. 49) are in an un-extended position (i.e. minimum protrusion with respect to the Marking Pen Housings 32) and locked in place. Alternately, the Marking Pens can be kept separate from the Marking Bracket at this point and attached when the US probe pose marking is required (see Step 3).
2. A pre-puncture scan can then be performed by the clinician.
3. When the US probe 6 is in the desired pose, each Locking Screw (FIG. 49) is loosened, if necessary, and the Marking Pens 29 are slid through the Marking Pen Housings 32 (one at a time) until they come in contact and mark the skin. The extension of each Marking Pen through the Marking Bracket Housing is locked by tightening the Locking Screws 30 (other locking means could be used).
4. The needle insertion length from the base of the US probe 6 to the epidural space is measured from the US scan and recorded. The needle insertion length to the top of the Needle Insert 3 (FIG. 56) can then be obtained either using the accompanying software or manually (simple addition).
5. The US probe 6 (with the Marking System) is then removed from the patient and the graduation measurement at the Reference Mark (item 33 in FIG. 49) for each Marking Pen 29 is recorded (see FIG. 54 and FIG. 55).
6. The US probe 6 and Marking System are put aside.
7. Markings on the skin may be covered at this stage with a transparent sterile tape and the skin can be disinfected using appropriate sterile technique.
8. The insertion length of the needle 1 with respect to the top of the Needle Insert, obtained in Step 4, is marked on the needle 1 using the Needle Insertion Length Rule shown FIG. 8, or by other means.
9. Sterile Needle guide 2 (FIG. 56) can now be used. The sterile Reference Pens are first set to the graduation measurement recorded in Step 5 and locked in place using Locking Screws 30 (or other means). Then a Needle Insert 3 is selected to suit the needle gauge and placed into the central hole in the guide (shown in FIG. 59(*a*)), ensuring the Needle Insert 3 is pushed fully into the Needle guide 2. For needles with a non-straight tip (e.g. Touhy), alternative inserts are used.
10. The sterile Needle guide 2 is then placed on the skin, with the sterile Reference
Pens 34 aligned with the markings on the skin made with the Marking Pens 29 in Step 3, and with a similar push force/pressure as the one applied during pre-scan skin marking. The path of the needle 1 through the needle guide 2 is now collinear with the final pre-scan centre line 10 of the US probe 6.
11. The needle 1 can now be inserted into the Needle guide 2 (see FIG. 59(*b*)) until the marking on the needle 1 made in Step 8 reaches the top of the Needle Insert 3 in the Needle guide 2. The needle (and especially for non-straight tip needles) can also be inserted in Step 9 if desired.
12. If the Needle guide 2 needs to be removed, the Needle Insert 3 can be lifted out of its housing and the Needle guide 2 removed using the cut out, as seen in FIG. 60(*a*) and FIG. 60(*b*). This is a similar method to that used in the Key System described previously.
13. The Needle guide 2 (with the Reference Pens and Screws) must be disposed of after the needling procedure if it is a disposable unit, or sterilised if it is a re-usable unit.

Alternate Marking Position (FIGS. 61, 62, 63, 64, 65*a* and 65*b*)

Figure 61:
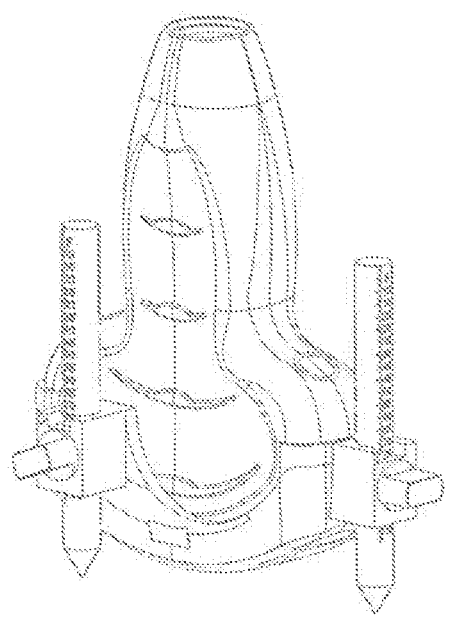
FIG. 61 is a perspective view of an ultrasound probe and surface marking guide according to the Marking Pen System with an offset marker.
Figure 62:
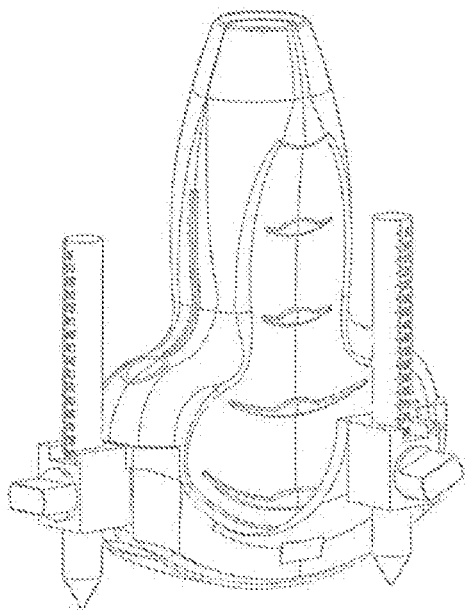
FIG. 62 is a perspective view of another ultrasound probe and surface marking guide according to the Marking Pen System with an offset marker.
Figure 63:
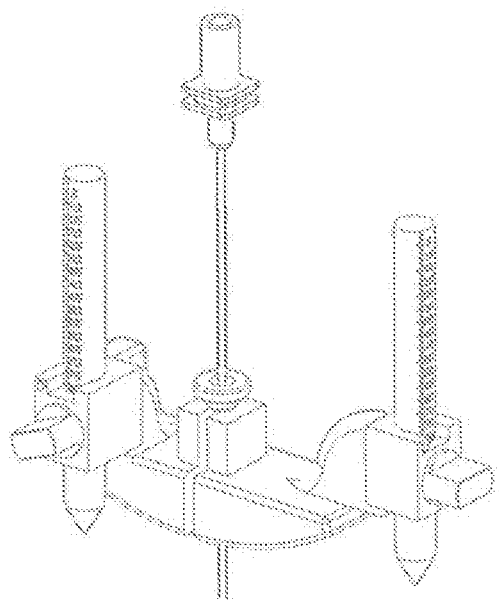
FIG. 63 is a perspective view of a Needle Insertion Guidance System corresponding to the surface marking guide of FIG. 61, with a needle positioned in the guide.
Figure 64:
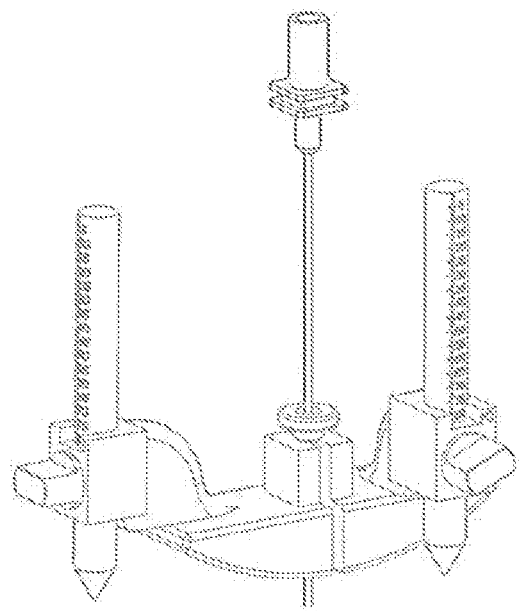
FIG. 64 is a perspective view of a Needle Insertion Guidance System corresponding to the surface marking guide of FIG. 62, with a needle positioned in the guide.
Figure 65A:
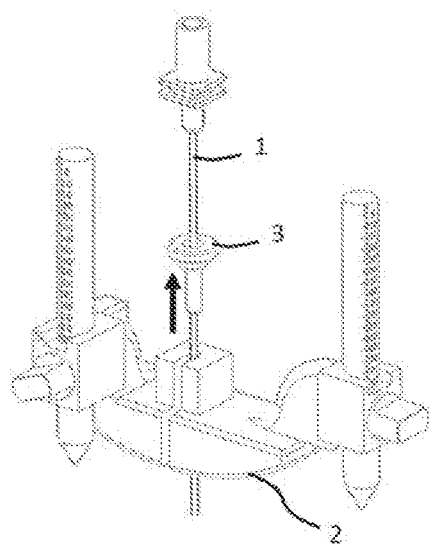
FIG. 65a illustrates removing a needle insert from a Needle Insertion Guidance System.
Figure 65B:
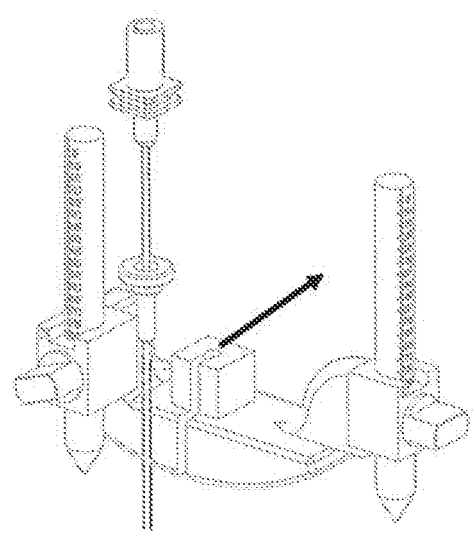
FIG. 65b illustrates removing a Needle Insertion Guidance System from the needle.

Rather than locating the Marking Pen 29 and Reference Pens 34 centrally with respect to the sagittal plane on the Marking Bracket and Needle guide 2 respectively, it may be offset to either side as shown in FIG. 61 and FIG. 62 (left and right hand versions) for the Marking guide 4 and FIG. 63 and FIG. 64 (left and right hand versions) for the Needle guide 2. This would allow the Needle guide 2 to be removed (if required) from the inserted needle 1 with greater ease as it would not require a diagonal motion, as shown in FIG. 65*a* and FIG. 65*b*. This will also help in changing the angle of the needle 1 in the sagittal plane after pulling out the needle insert, when needed.

Alternate Marking Method—Double Axis Pen System

Alternate embodiments of the Marking Pen 29 and Reference Pen 34 may be used.

Figure 71:
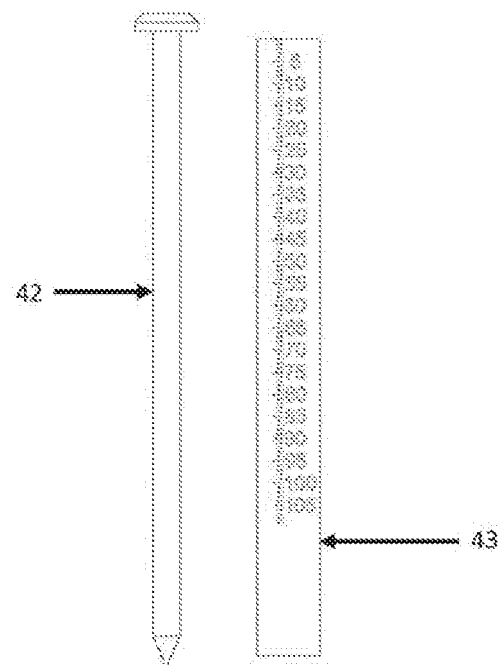
FIG. 71 illustrates an internal pen and outer case of an alternative marking pen.
Figure 72:
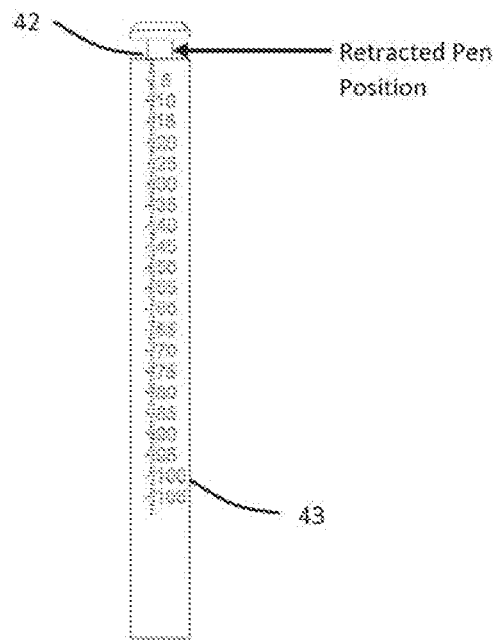
FIG. 72 illustrates the alternative marking pen of FIG. 71 in its retracted position.
Figure 73:
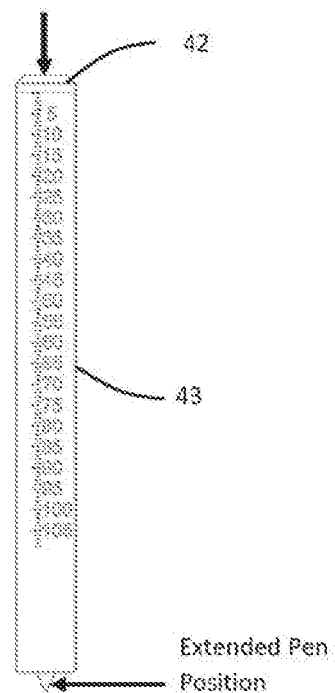
FIG. 73 illustrates the alternative marking pen of FIG. 71 in its extended position.

One further example of how the Marking Pens 29 can be designed is referred to as the Internal Pen Method; the marking part of this method has three parts (shown in FIG. 71): an Internal Pen 42, an Outer Case 43 and an internal spring mechanism between the two parts to allow the engagement (extension) and disengagement (retraction) of the Internal Pen 42 as shown in FIG. 72 and FIG. 73. This method has common features with the previous example such as the Reference Scale on the Outer Case 43 and the Pen Tip which serve the same functions.

One benefit of this method over the previous example is that the user can lower the outer case 43 onto the patient's skin and adjust it without leaving a mark.

Figure 74:
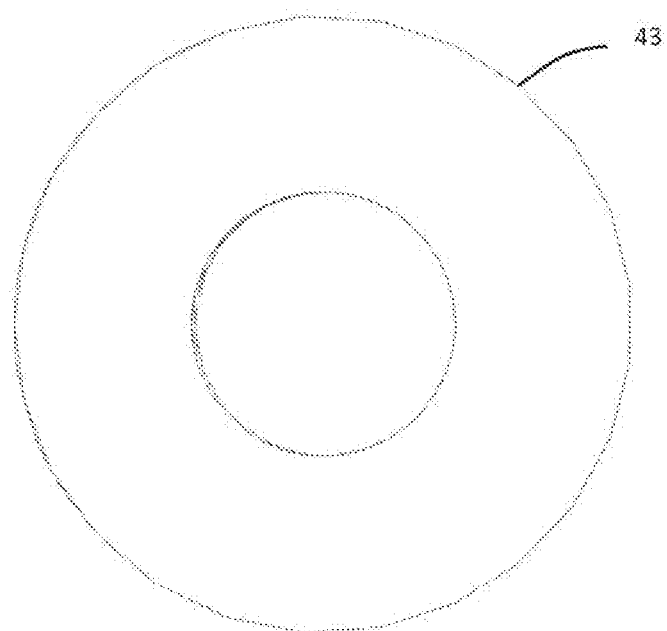
FIG. 74 illustrates the base of the Outer Case of the alternative marking pen of FIG. 71.

In order to mark the patient's skin the top of the Internal Pen 42 is pushed down as shown in FIG. 73. The base of the Outer Case 43, shown in FIG. 74, increases the contact area on the skin during marking compared to the previous example. This reduces the pressure on the skin, and so, may be more comfortable for the patient. Also, as mentioned previously the internal pen could deposit a sticker on the skin.

Figure 75:
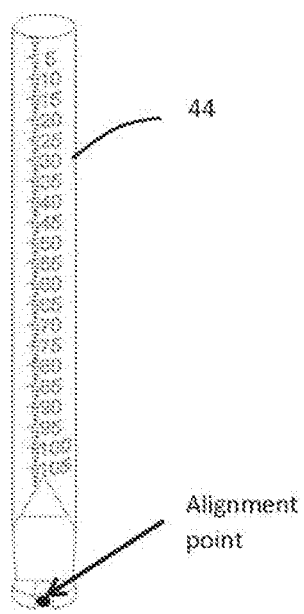
FIG. 75 illustrates an alternative reference pen.

The needle guide 2 is positioned by aligning the marking points with a cut out in the foot of the Reference Pen 44 as shown in FIG. 75.

Different Method of Locking the Marking Pens

Figure 78A:
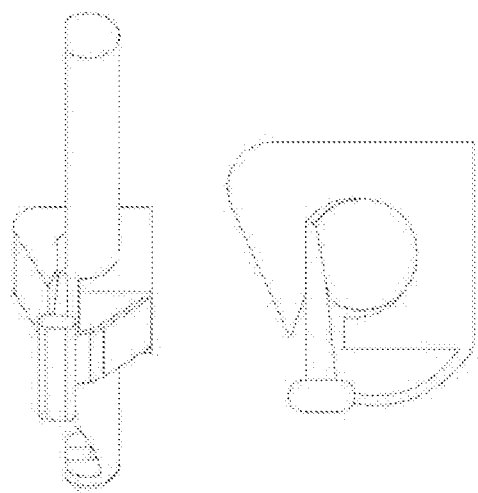
FIGS. 78(a) to (c) illustrate alternative marking pen locking mechanisms.
Figure 78B:
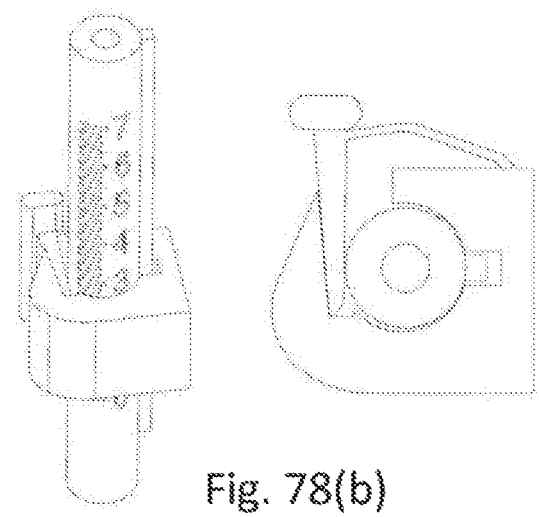
Figure 78C:
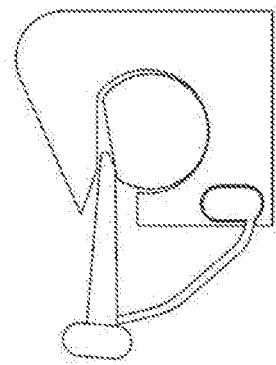

Different methods of locking the Marking and Reference Pens can be used. For example a wedge inserted between the marking pen and the housing. The marking pen can be circular (FIG. 78a) or non-circular (FIG. 78b). The wedge can be an integral part of the body (See FIGS. 78a and 78b) or can be a separate item inserted into the main body (FIG. 78c).

Marking Pen with Large Base

Figure 79:
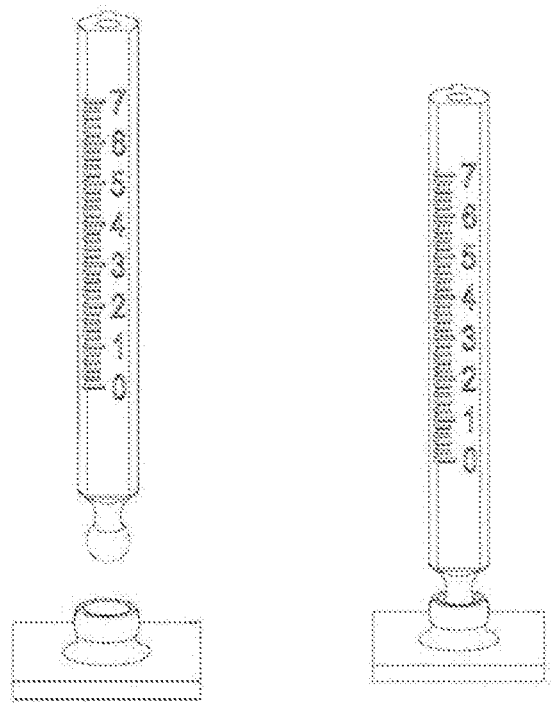
FIG. 79 illustrates a two part marker pen with a large base, with the pen and base separated in one view and connected in the other view.
Figure 80:
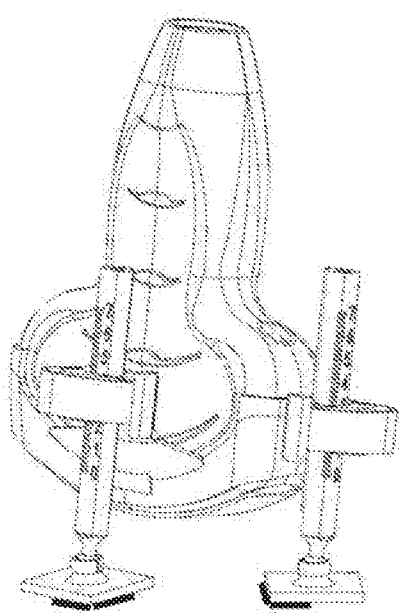
FIG. 80 shows pens with a large base mounted on an US probe for marking the skin.

In order to allow for a larger contact area with the patient's body, a marking pen with a larger surface area base could be used. The marking pen assembly could be in two parts, a support rod (with a measurement scale along its length) and an attachable base (foot), as shown in FIG. 79. The marking pen assemblies are pushed into the bracket without locking them. Once the pose of the probe is finalised, the two marking pen assemblies are pushed against the skin and locked, and the skin is marked using any corner of the base (alternative base designs may also be used), as shown in FIG. 80. A mark around just one corner of each base would be sufficient, but one could mark more than one corner. It should be noted that the base can have any orientation on the skin.

Figure 81:
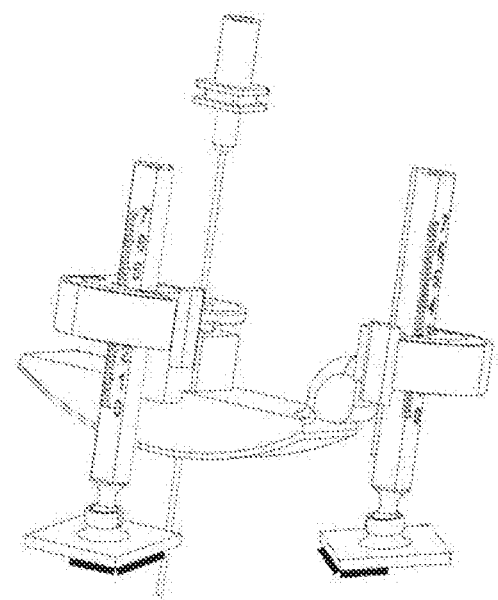
FIG. 81 shows a needle guide positioned using the marking pens having large bases.

The same procedure is followed to position and lock sterile reference assemblies (of the same design and shape as the marking pen assemblies) in a sterile needle insertion guide body as previously described, as shown in FIG. 81. However, for ease of use, the two sterilised bases (without the support rods) can be first stuck on the skin at the marks made and then the needle insertion guide system is positioned on the skin of the patient by placing the tips of the two support rods into the two bases.

Alternate Sterile/Non-Sterile Equipment

The Marking System is non-sterile, it is used during the pre-puncture scan before the insertion area of the skin is sterilised, as such simply disassembling the Marking System and disinfecting, using appropriate sterile technique, between uses is sufficient for reuse. However, for the Needle guide 2 there are two options; (1) the Needle guide 2 may be single-use in which case it will be delivered in sterile packaging and be disposed of after use; or (2) it may be made of a sterilisable material such as for example anodised aluminium or titanium and sterilised after/before use. The Needle Insert 3 is required in many gauge sizes (which may be colour coded) so it may be practical to have a single-use Needle Insert 3 and the rest of the Needle Guide System either reusable (sterilisable) or single-use.

Sterile Bracket with Corresponding Needle Guide

Instead of using a non-sterile bracket, a sterile bracket could be used instead during the skin marking phase. The same bracket with the marking pens locked in position is then used with a corresponding sterile needle guide attachment during the needle insertion phase. This removes any errors that may occur during the transfer of the depth positions of the marking pens from the bracket to the Needle Insertion Guidance System. This method also removes the need for a scale on the marking and reference pens.

Figures 82, 83:
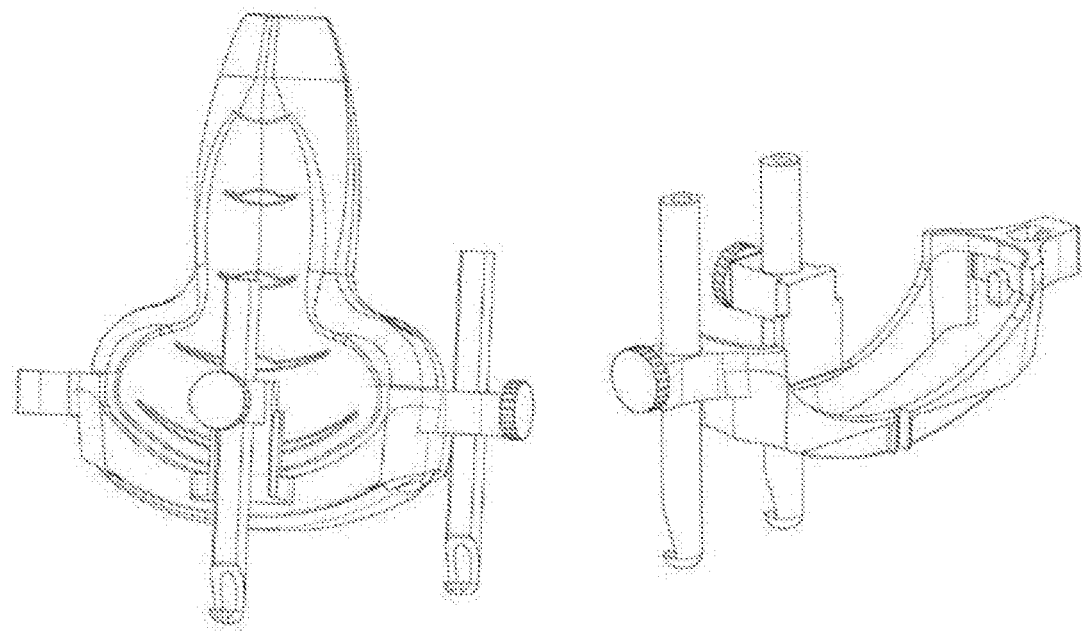
FIG. 82 illustrates a sterile bracket mounted on a US probe—the US probe will typically have a sterile cover but this cover is omitted from FIG. 82 for clarity.
FIGS. 83 to 86 illustrate the steps by which the sterile bracket shown in FIG. 82 is subsequently used in needle guidance.
Figure 84:
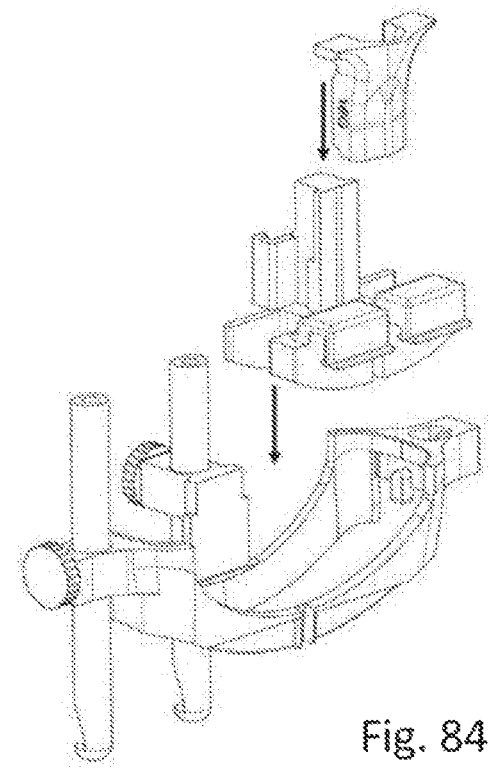
Figure 85:
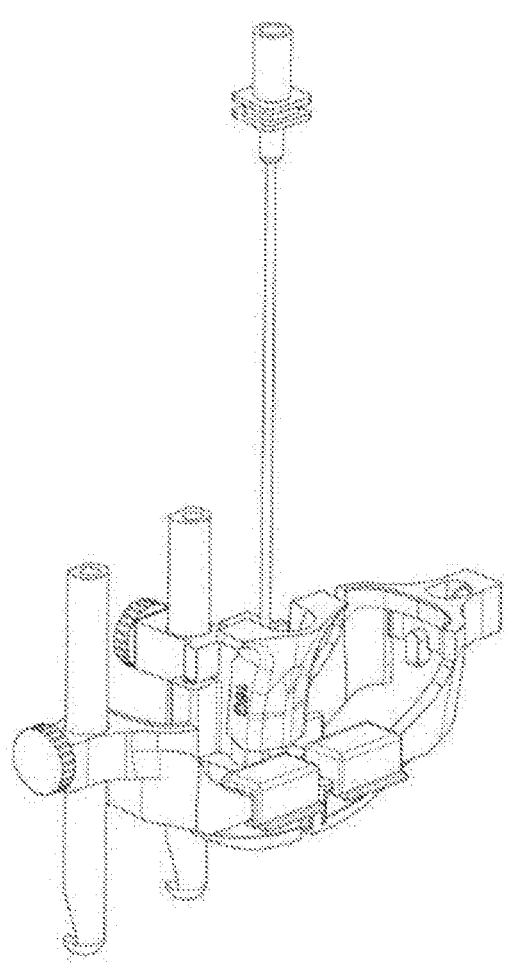
Figure 86:
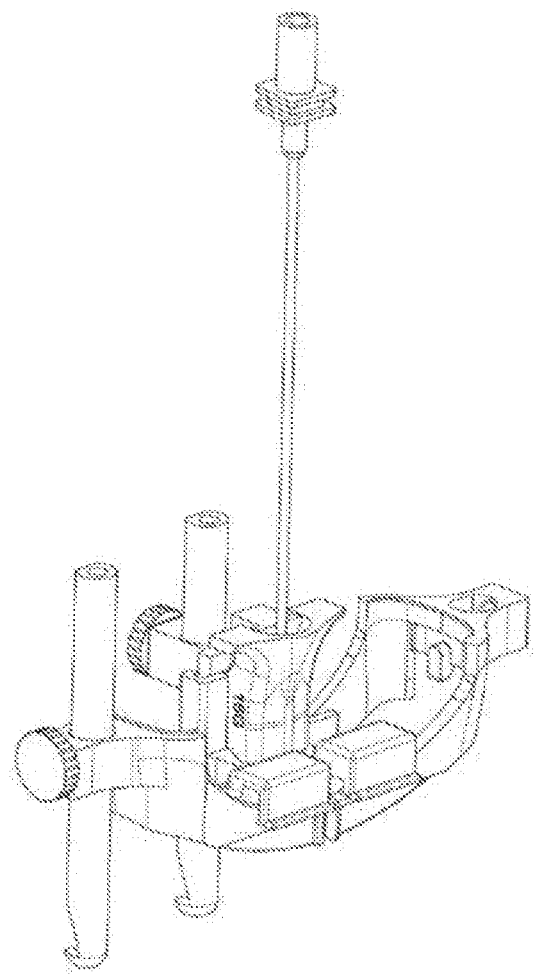

For this system, the skin is first disinfected using appropriate sterile technique, then: the US probe is placed into a sterile cover as per current practices; the sterile bracket is fixed to the US probe (FIG. 82); the pose of the US probe is defined in the usual way; the sterile marking pens (which can also be referred to as Reference Pens) on the sterile bracket are locked in position and the skin is marked in the same manner as previously described. Then, the sterile bracket (FIG. 83) is removed from the US probe and a needle guide body is inserted into the bracket (FIG. 84). The assembly is then positioned on the skin, using the marks on the skin, and the needle is inserted as described previously (FIGS. 85 and 86). The removal of the bracket-guide assembly to release the needle is also carried in the same way as previously described.

Sterile Bracket with Corresponding Needle Guide—Non Skin Marking Method

Some of the designs described above involve marking the body twice, one for each marking pen, and then realigning the epidural guide to the two marks made. Another alternative of the sterile system described immediately above uses "support rods" with "feet" as described further above. For this embodiment, the base (foot) has a loose interference fit to the "support rod", and has a sticky underside (e.g. double sided tape on the underside of the foot) to allow it to be stuck to the body once the pose of the US probe (with the bracket attached) is defined in the usual way, i.e. once the US probe is in the correct pose the "support rods" are pushed towards the skin to stick their corresponding "foot" to the skin. The "support rods" are then locked in position and the US probe together with the bracket is removed, leaving the "feet" in place (stuck to the skin). Then, the sterile bracket is removed (with the "support rods" still locked in position with respect to the bracket) from the US probe and a needle guide body is inserted into the bracket. The assembly (bracket with needle guide body) is then relocated on the skin by inserting each "support rods" into its corresponding "foot", and the needle is inserted into the patient as described previously. The removal of the bracket-guide assembly to release the needle is also carried in the same way as previously described, but in this case with the "feet" remaining in place, stuck to skin, and removed after the procedure is completed.

The "feet" do not need to have straight edges, as shown e.g. in FIG. 79; they can be circular or any other shape. Also, another advantage of this alternative is that there is no need to mark the body, thus making the process more accurate and quicker. Also, the support rods do not need a measurement scale along their length as they remain locked in position.

Double Axis—Variable Angle and Base Design

Figure 66:
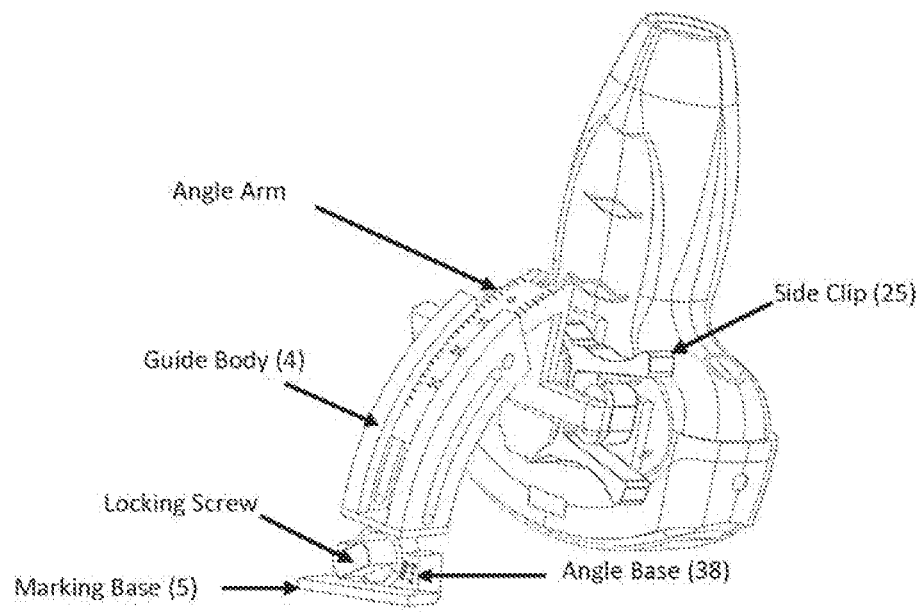
FIG. 66 illustrates an ultrasound probe and surface marking guide according to the Variable Angle and Base Design.
Figure 68:
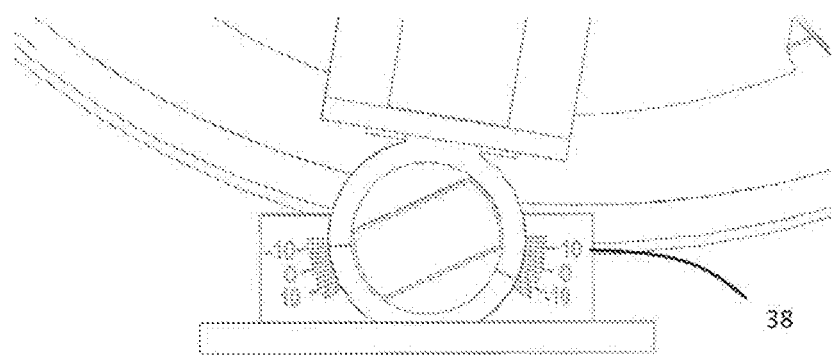
FIG. 68 illustrates a foot of the ultrasound probe and surface marking guide of FIG. 66.

The Variable Angle and Base design comprises two parts: a pre-puncture Marking System and a Needle guide 2. The design and operation is similar to that of the Single Axis epidural needle guidance system described previously. The difference between the Variable Angle and Base design and the Single axis design is that the Marking Base in the Variable Angle and Base system can rotate in the transverse plane as shown in FIG. 66. The Variable Angle and Base design is shown in FIG. 66. Typical graduations on the foot are shown in FIG. 68.

Figure 67:
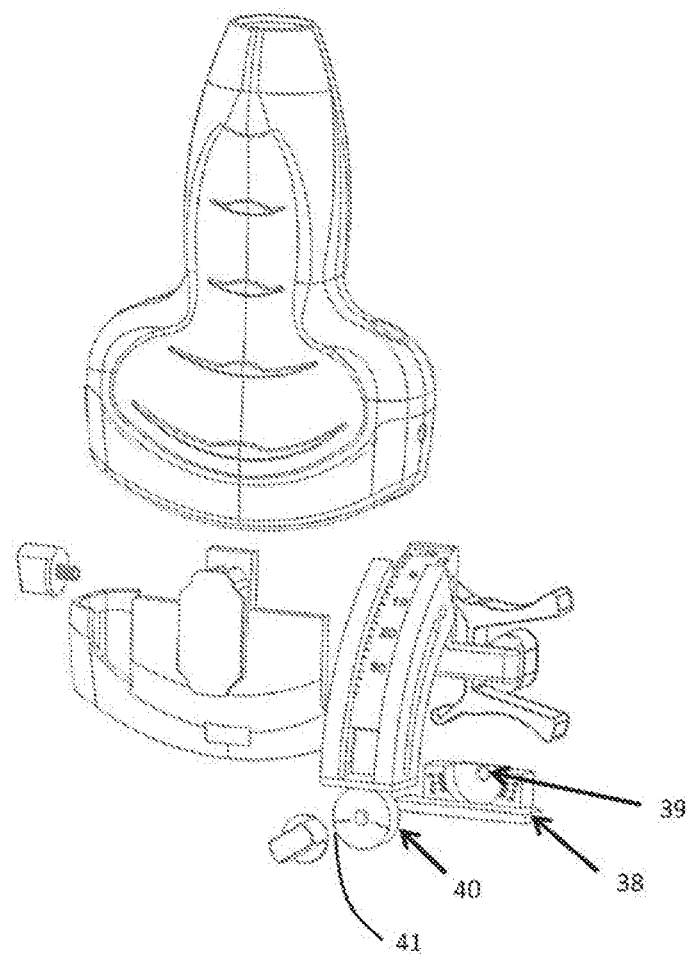
FIG. 67 is an exploded view of the ultrasound probe and surface marking guide of FIG. 66.

An exploded view of the full Marking System is shown in FIG. 67. The Male Part 40 of the cylindrical joint which connects Guide Body to the Marking Base rotates within the Female Part 39. The two parts of the cylindrical joint are locked together once the pose of the US probe 6 is finalised; an example of the locking mechanism may be such that the back plate of the Female Part 39 of the cylindrical joint having a threaded hole, and when a Locking Screw is tightened using the threaded hole a compressive force is exerted onto the cylinder joint, giving a frictional lock (alternative locking methods may be used). The angular position is given on the Angle Scale at either of the Reference Marks 41.

Figure 69:
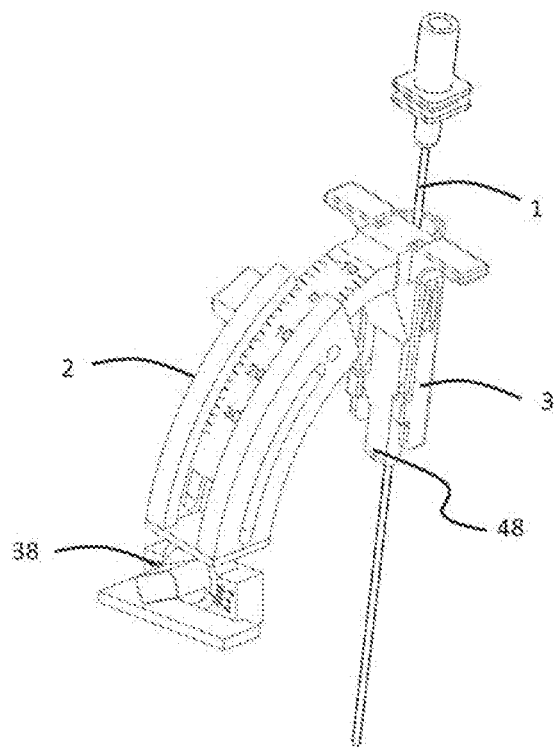
FIG. 69 illustrates a Needle Insertion Guidance System with a needle inserted within the guide which corresponds to the ultrasound probe and surface marking guide of FIG. 66.
Figure 70:
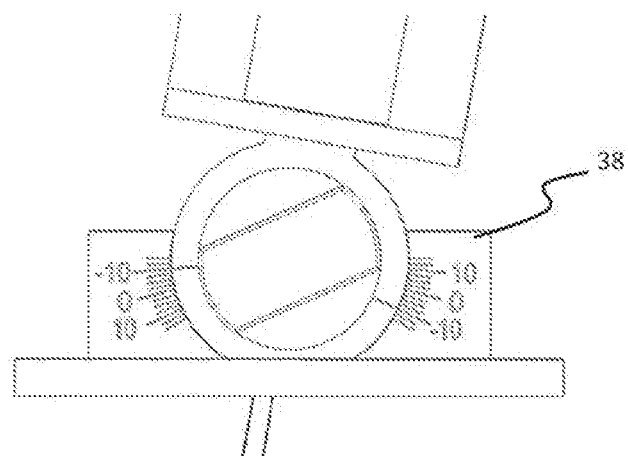
FIG. 70 illustrates a foot of the Needle Insertion Guidance System of FIG. 69.

The Needle Guidance System is shown in FIG. 69. The design is similar to that for the single axis system but with the same modification of the foot as described above for the Variable Angle and Base System design.

Process

1. The Marking Bracket, as shown in FIG. 36*b*, is attached to the US probe 6 using the locating features of the Marking Bracket.
2. The clinician performs a pre-puncture US scan on the patient with the Marking Bracket attached to the US probe 6.
3. Once a suitable needle insertion path to the epidural space is found, the Marking guide 4 is clipped onto the Marking Bracket using the Side Clip.
4. The Marking Base is extended onto the patient's skin and then both the Angle Arm and Angle Base 38 are locked in place with Screw Locks. It should be noted that a spring loaded marking guide 4 may be used to allow the Marking Base to remain against the skin without assistance while manipulating the US Probe 6.
5. The position of the Marking Base is marked on the patient's skin in the same manner as for the Single Axis system shown in FIG. 39.
6. The insertion length to the epidural space (i.e. the depth of epidural space from the skin) is measured from the US scan and recorded. The needle insertion length to the top of the guide can then be calculated either using the accompanying software or manually.
7. The US probe 6 (with the Marking System) is then removed from the patient.
8. The needle 1 is marked using the Needle Insertion Length Rule shown FIG. 8 or by other means.
9. A sterile Needle guide 2 (FIG. 69) can now be picked up. The Angle Arm and the Angle Base 38 are then positioned and locked at the same positions as given on the Marking guide 4 (in Step 4).
10. A Needle Gauge clip 3 of the desired needle gauge is clipped onto the Needle guide 2.
11. The marking on the skin may be covered by a sterile transparent tape (so that it does not rub off when the skin is cleaned). The skin is disinfected using the appropriate sterile technique. It should be noted that Step 11 may be performed before Steps 9 and 10.
12. The sterile Needle guide 2 is placed onto the patient's skin with the base aligned with the positional markings made in Step 5.
13. The needle 1 is inserted into the Needle guide 2 until the Needle Insertion Length Marking aligns with the top of the Needle guide 2, while simultaneously performing loss-of-resistance technique as desired by the clinician.
14. If required, the Needle Gauge clip 3 can be removed from the Needle guide 2, leaving the epidural needle in place and free to be manipulated by the clinician, as shown in FIG. 43. Similar to the Single Axis system, It should be noted that instead of transferring the angular position, read from the marking guide to a sterile needle guide (as per Steps 4 and 9), the non-sterile pre-scan Angle Arm (locked as describe in Step 4) can be detached from the bracket and placed in a suitable sterile cover. A needle channel 48, for example similar to the one shown as integral part of the needle guide 2 (FIG. 69), but designed with, for example, a mounting interface 26 can be attached through the sterile cover to the locked pre-scan Angle Arm.

Pre-Puncture System—Auto Alignment System

The auto alignment system uses a 3-axis accelerometer or gyroscope (the sensor) and works by providing the clinician with up to three angular orientations; one about each of the three perpendicular axes of the probe, which accurately describe the orientation of the US probe in space. Such orientation can then be transferred to a needle guide which is positioned by adjusting its orientation to match the previously acquired US probe orientation. Three angles are needed when the US probe position with respect to the skin is marked at just one location (e.g. with a dot corresponding to a feature on the US probe), and only two angles could be needed when the US probe position with respect to the skin is marked with two marks (e.g. two dots corresponding to two features on the US probe).

Figure 87:
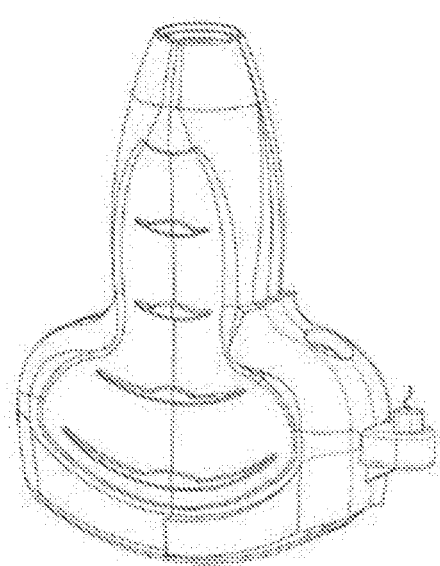
FIG. 87 illustrates an example of an orientation sensor mounted on a US probe.
Figure 88:
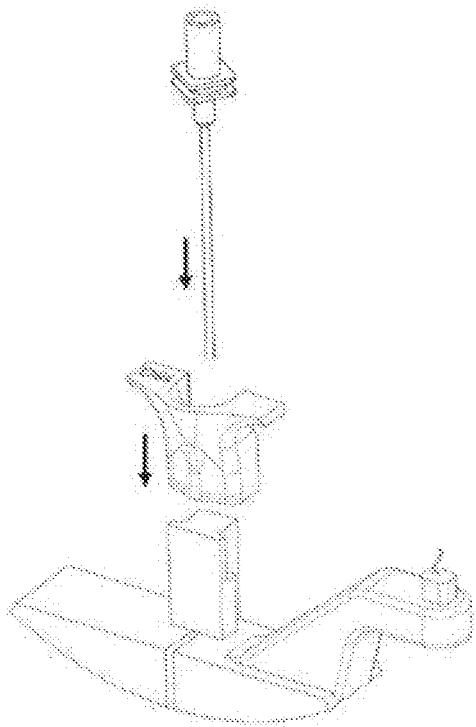
FIG. 88 illustrates a needle guide including an orientation sensor, along with a needle support and needle.

A typical scenario is given as follows. An appropriate sensor holder is clipped to the US probe. The orientation sensor (A 3-axis accelerometer or gyroscope) is fitted to the holder; (FIG. 87 depicts a typical example). The site of interest is scanned and once the pose of the US probe is finalised, a mark (e.g. a dot) is made on the skin at a known position with respect to the US probe, and a button integral with the sensor (or on an accessible pendant or integral with the US machine) is pressed to register of the final orientation of the US probe. The skin is then disinfected, using appropriate sterile technique. The sensor holder is put in a sterile bag and fitted to a sterile needle guide (FIG. 88 shows an example of the needle guide with sensor, a needle support and the needle—the sterile cover on the sensor is not shown for clarity of image). The needle guide is then placed at the same final position of the US probe using the mark on the skin. The clinician then orients the needle guide using one angular adjustment (pan, tilt or roll) at a time. Corresponding lights (LEDs) on the sensor can be used to aid the orientation of the needle guide. For example, the pan light will flicker at a varying frequency to indicate whether the guide is being rotated towards or away from the desired angular orientation until the correct angle is achieved; similarly for the other two angles. A graphical interface on the US machine screen, or on a separate screen, could also be used to assist the clinician to orient the needle guide quickly. Associated interface electronics and software protocols are used.

Figure 89:
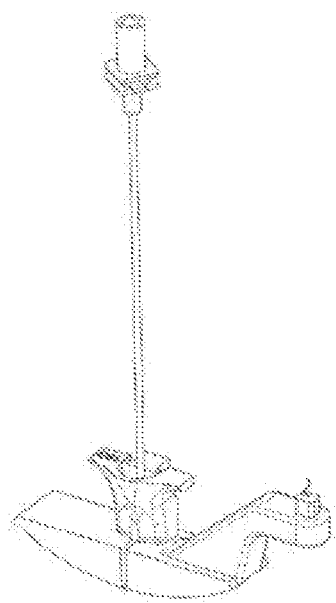
FIG. 89 illustrates the needle guide of FIG. 88 configured as it would be during insertion of the needle into the body of a patient.
Figure 90:
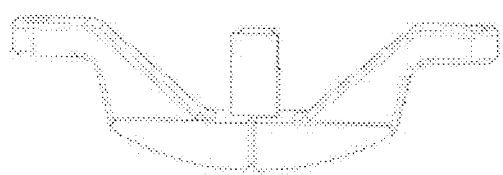
FIG. 90 shows a needle guide including two alternative supports for the orientation sensor.
Figure 91A:
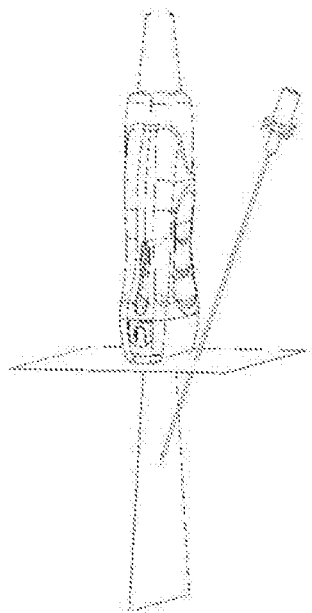
FIG. 91 illustrates a conventional, approach (without the use of a needle guide system) to needle insertion in conjunction with an ultrasound probe, showing an out-of-plane approach (a) and an in-plane approach (b)
Figure 91B:
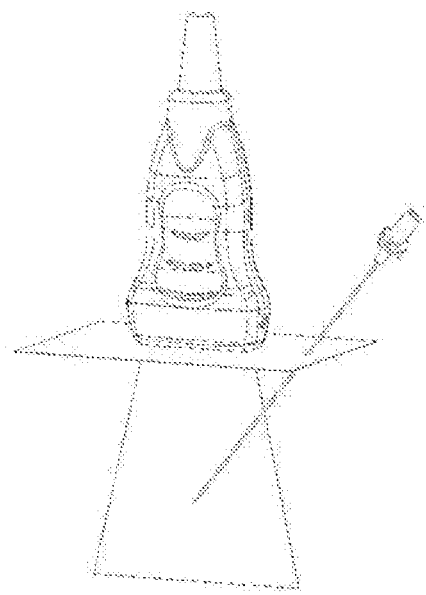

FIG. 89 shows a typical example of the needle guide system during the insertion of the needle into the body. FIG.

90 shows a needle guide composed of two alternative supports for the orientation sensor for ease of use.

A slightly different process can be used if it is desired to scan the body after disinfecting the skin.

Introducer Needle

The needle guide procedures have been described above using a needle 1 of appropriate gauge and the insertion length mark, on the main needle 1, has been referred to the funneled Needle Gauge Insert 3 or the Needle Gauge clip 3 (or the body of the needle guide in the case of the Protractor needle guide). However, it is sometimes necessary/desirable to use an Introducer Needle to make a skin hole, at the main needle insertion point, to facilitate entry of the main needle 1 through the skin; the main needle 1 is then pushed through the Introducer Needle to perform the rest of the procedure. In this case the Needle Gauge Insert 3 or the Needle Gauge clip 3 of appropriate gauge for the Insertion Needle is used. Also, the feature against which the mark for the insertion length of the main needle 1 is positioned may vary when the Introducer Needle is used. For example, the main needle insertion mark may be aligned with the (visible) end of the Introducer Needle when the Introducer Needle is inserted a known depth with respect to the needle guide 2. In this case, the Insertion Needle may be inserted a fixed/known length/depth identified by a mark on its body, or the Insertion Needle is inserted as desired, and the visible part of the Insertion Needle is measured and such length is used (with reference to a chart or inputted in an electronic device) to define the position of the mark on the main needle 1. The approach can be used in all of the embodiments exemplified above.

In addition, in the case of the embodiments exemplified by the Key System, special introducer needles could be provided as part of the package. The non-metallic section of such introducer needles will have the same external profile as the needle gauge insert 3 and thus can fit in the same way, as the needle gauge insert, to the guide, and the provided needle insertion length (described in the embodiments exemplified above) is unaffected. Also, the special introducer needles may project the base of the guide by specific lengths to suit the need of the clinician.

In any of the embodiments described above, the skin/surface contacting surfaces of one or more elements of the system (e.g. the base of the needle guide and/or the surface contact portion of the surface marking guide) may be 'sticky' (e.g. have an adhesive layer or substance applied to them) in order to help provide a stable placement once positioned on the skin/surface.

Real-Time Needle Guide

Figure 92:
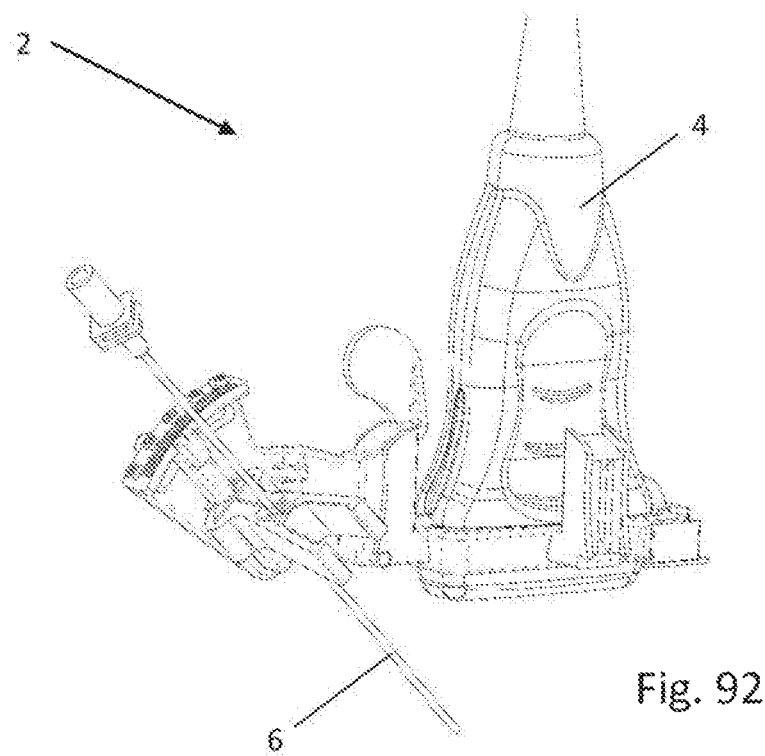
FIG. 92 shows a needle guide system in accordance with an embodiment of the invention.
Figure 93:
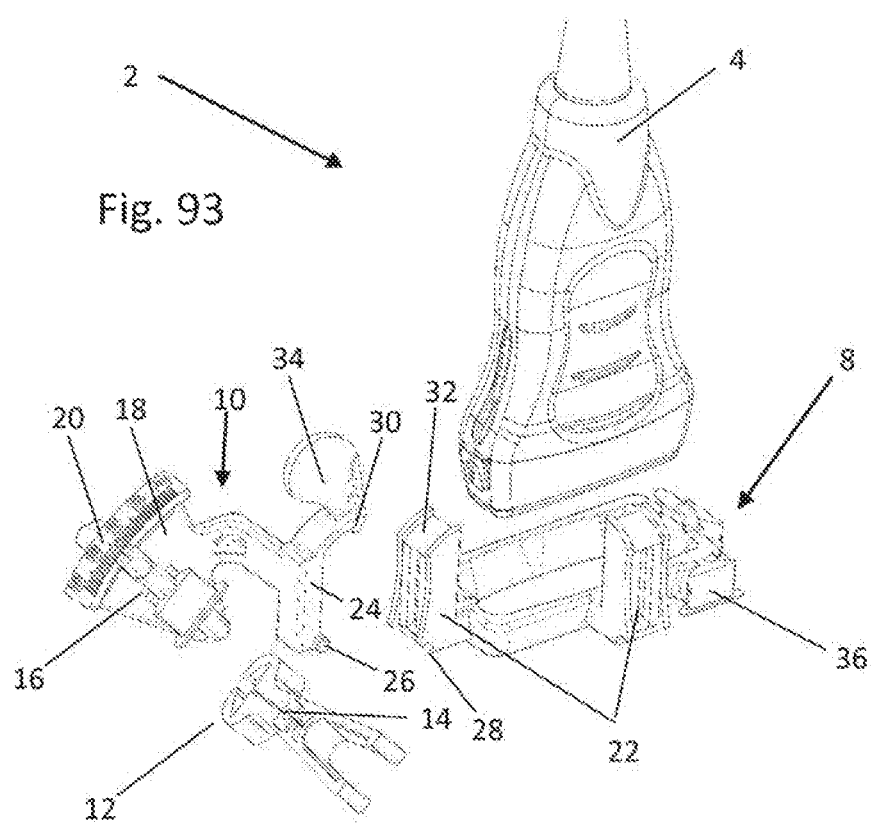
FIG. 93 shows an exploded view of the needle guide system seen in FIG. 92 (with the needle omitted)

FIGS. 92 and 93 show a needle guide system 2 in accordance with a first embodiment of the invention. The needle guide system 2 is mounted on an ultrasound probe 4 (i.e. a hand held ultrasound probe). FIG. 92 shows a needle 6 located in a needle channel in the guide system 2 to be held at a specific position and orientation relative the ultrasound probe 4.

The tip of the needle can be guided to a desired target, e.g. in a human body, beneath the ultrasound probe by appropriate selection of the angle and length of needle insertion. The operator of the system can be provided with tabular information to give them the required angle and needle insertion length for a given depth below the probe or the software driving the ultrasound system, or another device, could be configured to provide this information to the operator.

The needle guide system 2 includes a bracket 8 for mounting on the ultrasound probe 4, a needle guide body 10 that releasably attaches to the bracket 8, and a needle support 12 that, in this example, releasably clips to the needle guide body 10.

The needle 6 is received within a needle channel 14 defined in the needle support 12. The diameter of the channel 14 is only a little large than the diameter of the needle 6, so that when the needle 6 is located within the channel it is free to move up and down through the channel 14 but is held securely with its axis extending along the central axis of the channel to accurately control the trajectory of the needle relative to the probe.

The needle support 12 in this example is clipped to a pivot arm component 16 of the needle guide body 10. The angle of the pivot arm 16 can be adjusted relative to a mounting part 18 of the needle guide body 10 (the mounting part 18 mounting the needle guide body 10 on the bracket 8), about a pivot at the bottom end of the pivot arm 16, in order to adjust the orientation of the needle support 12 relative to the mounting part 18 and hence to change the angle of the needle channel 14 relative to ultrasound probe 4 when the system 2 is mounted on the probe 4 via the bracket 8. A lock element, for example a thumb screw, can be provided to lock the pivot arm 16 at the desired angle.

As the angle of the pivot arm 16 is adjusted, an upper end of the pivot arm 16 moves along a scale 20 on the mounting part 18 of the needle guide body 10, allowing the operator to accurately set the angle of the needle channel 14. The marking on the scale 20 may provide a measure of angle, as seen in FIG. 106 or, in some embodiments, the scale markings can instead show depths of the target taken along the centreline of the ultrasound probe. Taking the latter approach the depth measurement along the ultrasound probe axis is used directly to adjust the angular position of the guide. However, typically two scales are needed in this case, one for in-plane procedures and one for out-of-plane procedures, because the distance between the needle support and the centre line of the probe will tend to be shorter for out-of-plane procedures (although an alternative is to use the same scale for in-plane and out-of-plane procedures by setting the distance from the needle guide attachment to the proce central axis to be the same for both procedures). An exemplary dual depth scale, one for in-plane and one for out-of-plane procedures, is illustrated in FIGS. 107(*a*) and (*b*), which is the same component from opposite sides.

As seen most clearly in FIG. 92, the bracket 8 is shaped to fit snugly on the ultrasound probe 4. Different brackets can be provided for different shapes of probe. Various different designs of bracket are possible, one alternative being a bracket that clips around the probe from the side rather than being pushed onto the probe from the bottom as with the illustrated example. A further example is a bracket in two (or more) parts that can be mounted on the probe and held in position using an appropriate locking mechanism to secure the parts of the bracket to one another and/or to the probe The bracket 8, in this example, has two mounting projections 22 to which the needle guide body 10 can be mounted. In this example, the needle guide body is mounted to the projections 22 on the bracket by a clip portion 24 of the needle guide body 10. Lugs 26 at either side of a bottom end of the clip portion 24 engage recesses 28 at the bottom of the mounting projections 22 and a latch 30 at the top of the clip portion 24 latches over a top end 32 of the projections 22 to securely attach the needle guide body 10 to the bracket 8. In this example, a tab 34 extends from the top of the clip portion 24 and can be manipulated to release the clip portion 24 from the mounting projections 22 to disengage the needle guide body 10 from the bracket 8. The two mounting projections 22 are positioned on the bracket 8 to enable the needle guide to be mounted for in-plane and out-of-plane use respectively. Additional lugs 36 are also provided on the bracket 8 to which the needle support 12 can be clipped to temporarily store the needle support 12 when not clipped to the needle guide body 10, for example when the needle 6 has been released in order to be manipulated.

Figure 94:
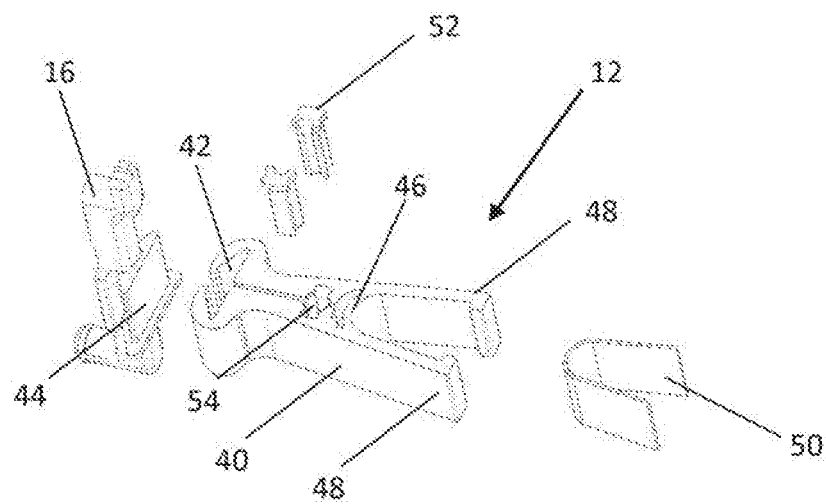
FIG. 94. shows, on an enlarged scale, an exploded view of the needle support clip of the needle guide system seen in FIG. 92, along with the component of the needle guide body to which it attaches.

FIG. 94 shows the needle support 12 on an enlarged scale. In this example, the needle support is a clip having two arms 40. At one end the arms define a socket 42 within which a protrusion 44 on the pivot arm 16 of the needle guide body can be engaged to secure these two components together. The arms 40 are pivoted to one another, in this example by being formed as a unitary component including a flexible bridge portion 46 spanning between the arms 40 to provide a pivot. Grip portions 48 are provided at the ends of the arms opposite the socket 42, with the bridge portion 46 being about half way along the length of the arms 40. By squeezing the grip portions 48 together, the jaws of the socket 42 at the other end are spread apart, allowing them to be clipped over the protrusion 44. The grip portions 48 are resiliently urged apart by a spring 50 (shown separated from the clip in FIG. 94 but in use would be located between the arms 40), so that when they are released, the jaws of the socket 42 close tightly around the protrusion 44 to hold the needle support securely in place on the pivot arm 16.

The needle channel 14 is formed within the needle support between a pair of needle channel inserts 52 that are fixed to respective ones of the arms 40. By using inserts in this way, the needle guide system can be adapted to different needle sizes simply by changing the needle channel inserts 52.

The needle channel inserts are located in the arms on the same side of the bridge portion 46 as the socket 42 (i.e. on the opposite side of the bridge 46 to the grip portions 48), in the passage 54. Consequently, when the grip portions 48 are squeezed together to open the jaws of the socket 42, the two channel inserts are also moved apart. In this way, at the same time as releasing the needle support 12 from the needle guide body 10, the needle support can also be completely removed from the needle 6 itself, for example if it is desired to manipulate the needle to navigate safely around e.g. a vessel, or through tough tissue/ligaments. The clinician will then be able to re-attach the guide component back in place and continue. This process can be reversed to place the needle back in the needle channel 14 and re-attach the needle support 12 to the needle guide body 10, all without disturbing the insertion depth of the needle. This ability to release the needle also allows the clinician to free the needle from the assist device and carry out the procedure without any guidance, when a particular situation demands it.

A needle guide in accordance with a second embodiment of the invention is shown in FIGS. 95 to 97. Similarly to the first example above, the needle guide 60 includes a needle guide body 62 that can be mounted on an ultrasound probe via a bracket (for example as shown in FIGS. 104 and 105) and a needle support 64 that clips to a pivot arm 66 of the needle guide body 62.

In this second example, the clip portion 68 of the needle guide body 62 has a different form to the clip portion 24 in the first example above but it performs the same function of releasably attaching the needle guide body 62 to a selected one of one, two or more mounting protrusions on the bracket in order to hold the needle guide in a predetermined position and orientation relative to the ultrasound probe.

Similarly to the first example, the needle support 64 of this second example includes two arms 70 that are pivoted to one another by a bridge portion 72. Grip portions 74 at one end of the arms can be squeezed together to open up the other end of the arms, which engage with the pivot arm 66. In this example, one of the arms 70 has a straight end 76 that engages a slot 78 in the pivot arm 66. The other arm has a latch 80 at its end that latches around an angled protrusion 82 on the pivot arm 66. By squeezing the grip portions together, similarly to the first example, the latch 80 is disengaged from the protrusion 82, allowing the straight end 76 of the other arm to be withdrawn from the slot 78 to disengage the needle support 64 from the needle guide body 62 (if the needle has been inserted and is to be left in situ, then it must also be released from the needle support in the manner described below).

However, unlike the first example, the needle channel 84 in this example is formed between an inside face of one of the arms 70 (in this case, the arm carrying the latch 80) and a single needle channel insert 86 mounted on that arm. As best seen in FIG. 97, the needle channel insert 86 is pivotally mounted on the arm 70 so that it can be twisted away from the inside surface of the arm to open the needle channel 84 in order that the needle support 64 can be removed from the needle.

The pivot connection between the needle channel insert and the arm is preferably configured so that there is resistance to the insert moving away from the arm to open the channel. For example, one or more detents in the pivot connection may be used to resist movement of the insert until a certain degree of force is applied to 'snap' the insert open. To facilitate this movement, a tab 88 protrudes from the rear of the channel insert, to the opposite side from the needle channel of the inserts pivot connection to the arm, providing a lever for opening and closing the channel insert.

FIGS. 108 (a) and (b) show the needle channel insert 86 separated from the arm 40 and on an enlarged scale. The tab 88 is clearly visible as is the open channel that forms the needle channel 84. Spigot 89 engages with an aperture in the arm 70 to provide the pivot connection.

It will be appreciated that in this example the needle channel 84 can be opened and closed independently of the squeezing together of the grip portions 74 to open the latch 80.

Similarly to the first example, the needle support 64 of this example can be readily adapted to different needle sizes by simply changing the needle channel insert 86.

A third example of a needle guide system is shown in FIGS. 98 to 101. As with the previous examples, the needle guide system includes a bracket 90 for mounting on the ultrasonic probe. A needle guide body 92 clips onto the bracket 90 in one of two different positions, for in-plane and out-of-plane use respectively (see FIGS. 99 and 100). A needle support 94, in which a needle channel 96 is formed, is mounted on a pivot arm 98 of the needle guide body 92.

In this example, the needle guide body 92 is mounted on the bracket 90 by a clip arrangement including a mounting interface 91 on the bracket 90 and a clip 93 on the guide body 92. The mounting interface and clip have mating faces that locate the two components relative to one another. The clip 93 has opposed clip portions that engage under opposite ends of the mounting interface 91 when the clip is pushed down onto the mounting interface. To release the clip from the mounting interface (and hence release the needle guide body 92 from the bracket 90) upwardly extending tabs on the clip 93 are squeezed together to spread apart the clip portions and release them from below the ends of the mounting interface. The guide body 92 can then be lifted directly upwardly away from the bracket.

In this third example, the scale 100 for indicating the angle of the needle channel 96 is carried by the pivot arm 98. The scale 100 moves relative to fixed part 102 of the needle guide body 92 as the pivot arm 98 is moved and the angle can be read off the scale adjacent a marker 104 on the sides of a channel 106 in the fixed part 102 of the needle guide body 92 through which the scale 100 slides.

Figure 99:
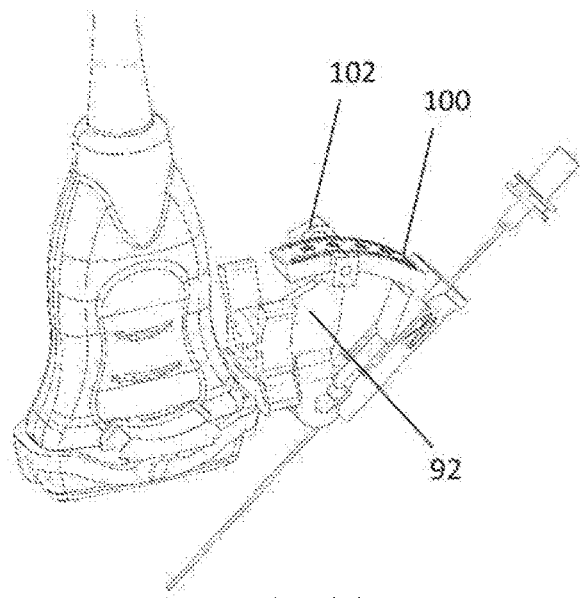
FIG. 99 shows the needle guide system of FIG. 98 mounted on an ultrasound probe in an in-plane configuration.
Figure 100:
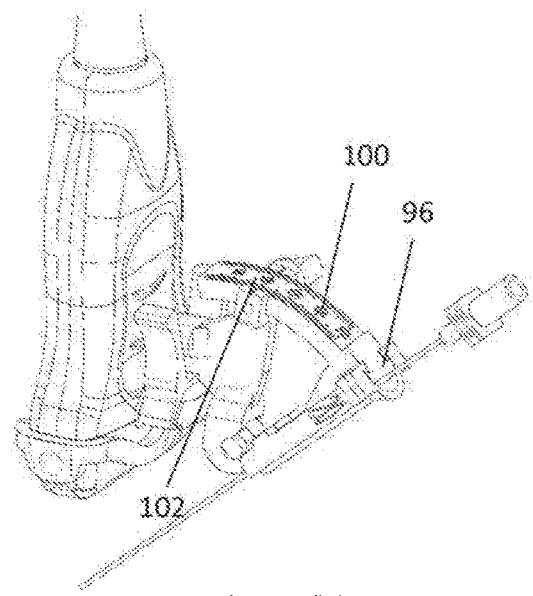

The needle support 94 is mounted on the rear face of the pivot arm 98, rather than on a side of the pivot arm as in the previous examples. This means that when a needle 106 is held in the needle channel 96 it is in-line with the pivot arm, rather than being off-set to one side of the pivot arm (as in the embodiments of FIGS. 92 to 97) and can be in-line with the central plane of the needle guide body, so that the needle, pivot arm and centre line of the needle guide body are all in-line with the ultrasound image plane when the needle guide system is configured as shown in FIG. 99.

In this example, as seen most clearly in FIG. 101(*c*), the needle support 94 is an elongate, channel member that is open on the side 108 that faces the pivot arm 98. The needle channel 96 in the needle support is closed by the rear face of the pivot arm 98 when the needle support 94 is connected to the pivot arm 98. As illustrated in FIGS. 101(*a*) to (*c*), the arrangement means that the needle 107 can easily be released from the needle channel 96, without its position being disturbed, by detaching the needle support 94 from the pivot arm 98. This is achieved by first lifting the needle support 94 upwards relative to the pivot arm, from the position seen in FIG. 101(*a*) to the position seen in FIG. 101(*b*). This disengages tabs 110, 112 on the front face of the needle support 94, from corresponding slots 114 and detents 116 at the top and bottom of the pivot arm 98 respectively. Once these tabs 110, 112 are disengaged, the needle support 94 can be withdrawn backwards away from the pivot arm 98, opening the needle channel 96 and releasing the needle 106. To secure the needle 106 in the channel 96, this procedure is reversed.

Similarly to the previous examples, different size needles can be accommodated by providing a range of needle supports 94 having differently sized needle channels 96 therein.

In cases when the needle tip is not uniform with respect to the rest of the cylindrical section of the needle, for example a Tuohy needle (See FIG. 110), the needle support 94 could be partly positioned on the pivot arm 98, the needle 107 is mounted loosely on the needle channel 96 to allow enough space for the non-uniform part of the needle to be pushed through the needle channel 96. The needle support 94 is then fully engaged into the pivot arm 98.

FIG. 102 shows three different possible configurations for the needle support of the third and/or fourth examples. They differ from one another in the location and size of tabs 118, 119 that help when grasping the needle support 96 to detach it from the pivot arm 98 of the needle guide body 92. The tabs help to stop the user's fingers sliding upwards when the needle support is grasped with two fingers. The needle supports shown in FIGS. 102(*a*) and 102(*b*) can be grasped by the relatively large tab 118 or in the case of the needle support shown in FIG. 102(*b*) the support can be grasped with a finger to either side of the support under or around the two tabs 118, 119. In the case of the needle support shown in FIG. 102(*c*), which has two relatively small tabs 118, 119, it would normally be removed by grasping with a finger to either side of the support under or around the two tabs 118, 119. It can also be seen that, conveniently, these tabs 118 are used to carry an indication of the gauge of needle for which the needle support 94 is intended. Such indications can additionally or alternatively be carried on a side wall of the needle guide as seen in FIGS. 101 (*a*), (*b*) and (*c*) for example, or elsewhere on the needle guide body.

The needle support shown in FIG. 102(*a*) is suitable for use with the fourth example described below. The needle guides shown in FIGS. 102(*b*) and 102(*c*) are suitable for use with the third example described above and the fourth example described below.

FIG. 103 shows a fourth example of needle guide system in accordance with an embodiment of the invention. In this example, the needle support 120 has a similar form to the needle support of the third example, being an elongate channel member, having a needle channel 122 therein, one side of which is closed by the pivot arm 124 of the needle guide body 126. However, in this example, the needle support is mounted on the side of the pivot arm 124.

The angular positioning of needle channel 122 is similar to the first and second examples. The needle support 120 in this example is clipped to the pivot arm 124 of the needle guide body 126. The angle of the pivot arm 124 can be adjusted relative to the main body 128 of the needle guide body 126 about a pivot at the bottom end of the pivot arm 124, in order to adjust the orientation of the needle support 120 relative to the mounting part 128 and hence to change the angle of the needle channel 122 relative to the ultrasound probe. A lock element, for example a thumb screw, can be provided to lock the pivot arm 124 at the desired angle. Another method of locking the pivot arm 124 is using a system which locks the pivot arm at fixed increments with increased resolution using the mechanism shown in FIG. 109. The upper finger grip 137 locks the pivot arm 124 to the upper rack 138, while the lower finger grip 139 locks the pivot arm 124 to the lower rack 140. The upper rack 138 and the lower rack 140 have the same pitch (for example providing 2 degrees rotational increments each). The two racks 138 and 140 are offset by half the pitch (i.e. 1 degree offset for this example). This allows the pivot arm 124 to be rotated in increments of half the pitch of each rack (i.e. 1 degree increment for this example); thus providing higher resolution and an easier locking method.

FIG. 104 shows one example of a bracket 130 that can be used to mount a needle guide to an ultrasound probe. FIG. 105 shows the bracket mounted on a probe 132. The bracket 130 is designed to be a snap fit over the lower end of the probe 132 and is shaped so that it always locates in a fixed position on the probe. This is important to ensure that a needle guide mounted on the bracket is always in a known position relative to the probe.

The bracket can be mounted on the ultrasound probe before a sterilised cover is pulled over the probe, with the needle guide being fixed to the bracket from outside the cover (whilst carefully squeezing, and without damaging, the cover around the needle guide mount). Alternatively, the bracket can be mounted externally to the cover without damaging the cover and can serve to hold the cover tightly around the end of the probe.

Another alternative is a bracket in two (or more) parts that can be mounted on the probe internally or externally of the sterilised cover and held in position using an appropriate locking mechanism.

Different models of ultrasound probe vary in shape from one another so typically a different shape bracket would be provided for each model of probe.

The bracket illustrated here includes two mounting positions for the needle guide, a first position 134 on a long side of the probe 132 and a second position 136 on a short side of the probe, for out-of-plane and in-plane use respectively. The bracket need not have two mounting positions for the needle guide. In some examples it may only have one mounting position for the needle guide. In other examples the bracket may have more than two mounting positions for the needle guide, for example three positions, four positions or more, spaced at intervals around the bracket.

Where practicable, features described above in the context of pre-puncture embodiments can also be used in conjunction with real-time embodiments and vice versa. The skilled person will also appreciate that the needle guides illustrated in the Figures and described above are examples embodying inventive concepts described herein and that many and various modifications can be made without departing from the invention.

REFERENCES

[1] Karthikeyan Kallidaikurichi Srinivasan, Peter John Lee, Gabriella Iohom, US for neuraxial blockade, Med Ultrason 2014, Vol. 16, no. 4, 356-363.
[2] Grau, T., Leipold, R. W., Conradi, R., Martin, E., Motsch, J., *Efficacy of Ultrasound Imaging in Obstetric Epidural Anaesthesia. Journal of Clinical Anesthesia* 2002, V14, 169-175
[3] Chin, K. J., Perlas, A., Chan, V., Brown-Shreves, D., Koshkin, A., and Vaishnav, V. *Ultrasound Imaging Facilitates Spinal Anaesthesia in Adults with Difficult Surface Anatomic Landmarks. Anesthesiology* 2011, V115, No. 1, 94-101.

The invention claimed is:

1. A needle guide system for use with an ultrasound probe, the needle guide system comprising:
   (i) a surface marking guide; and
   (ii) a needle guide;
   (i) the surface marking guide including:
      (a) an attachment portion for removably attaching the surface marking guide onto an end of the ultrasound probe, the end of the ultrasound probe being adapted to hold against a surface to capture one or more ultrasound images; and
      (b) a surface contact portion fixed to the attachment portion, the surface contact portion including one or more marking features for identifying to a user where to make a mark identifying a position on the surface for a positioning component of the needle guide on the surface when the ultrasound probe is held against the surface to reach an internal target inside a subject; and
   (ii) the needle guide including:
      (a) a base to support the needle guide on the surface;
      (b) one or more alignment features on the base for aligning the base with the mark made on the surface using the one or more marking features of the surface marking guide;
      (c) a sensor for measuring an orientation of the surface marking guide in space, wherein the needle guide comprises a corresponding sensor for measuring the orientation of the needle guide, wherein the needle guide is subsequently positioned to have the same orientation as the surface marking guide; and
      (d) a needle support mounted on the base and having a needle channel through which movement of a needle is supported, wherein the needle guide is configured for the needle channel to be positioned and oriented to be pointed at another position on the surface that differs from the position of the imaged target on the surface.

2. The needle guide system according to claim 1, wherein the needle guide further comprises:
   at least one additional alignment feature for aligning the base with the mark made using the one or more marking features of the surface marking guide; and
   wherein the surface marking guide further comprises:
      one or more offset-prompting marking features for identifying to the user where to make a secondary marking offset from the mark made using the one or more marking features of the surface marking guide.

3. The needle guide system according to claim 1, wherein said one or more marking features of the surface contact portion of the surface marking guide define a position relative to a center line of the ultrasound probe and an orientation of the ultrasound probe.

4. The needle guide system according to claim 1, comprising a plurality of needle guides, wherein the plurality of needle guides includes the needle guide, each needle guide of the plurality of needle guides having a base to support the needle guide on the surface and a needle support mounted on the base, the needle support having a needle channel to guide traversal of a needle, wherein the plurality of needle guides differ from one another at least with respect to an angle of the needle channel of the needle guide relative to the bases of the needle guide.

5. The needle guide system according to claim 1, wherein the surface marking guide and needle guide are configured so that when the needle is in the needle channel with the needle guide located by the marks on the surface, the needle is aligned with a virtual probe axis, the virtual probe axis being an axis that was through the center line of the ultrasound probe when the ultrasound probe was positioned on the surface and the surface was marked using the surface marking guide.

6. The needle guide system according to claim 1, wherein the surface contact portion of the surface marking guide is fixed to the attachment portion via a curved arm, a center or curvature of the curved arm being located at a mid-point of the ultrasound probe when the surface marking guide is mounted on the ultrasound probe.

7. The needle guide system according to claim 1, further comprising a needle for insertion in the needle channel.

8. The needle guide system according to claim 1, wherein the needle support includes an orientation-setting component configured to:
   support, when the orientation setting component is in a first state, user manipulation across a particular degree of freedom that changes an orientation of the needle channel relative to the base; and
   fix, when the orientation setting component is in a second state, the orientation of the needle channel relative to the base and to thus remove the particular degree of freedom.

9. The needle guide system according to claim 8, wherein the orientation-setting component includes a pivoting connection that connects an arm of the needle support with the needle channel and that facilitates the orientation-setting component to pivot about a virtual or physical center of rotation.

10. The needle guide system according to claim 8, wherein the orientation-setting component includes:
    (a) a bracket that fixes the needle support to one of a plurality of discrete needle support mounting positions on the base, an angle of the needle channel being different at each mounting position, or
(b) a pivoting component that interfaces that controls a relative angle between the needle support and the base of the needle guide.

11. A method of positioning a needle guide on a surface, the method comprising:
removably attaching a surface marking guide onto an end of an ultrasound probe, the end of the ultrasound probe being adapted for holding against a surface;
configuring the ultrasound probe to image and locate an internal target inside a body of a subject, wherein the configuring includes placing the end of the ultrasound probe at a position on the surface of the body for positioning the needle guide, the ultrasound probe having the surface marking guide attached thereto;
marking the surface for positioning the needle guide on or adjacent to the surface marking guide with one or more primary marks;
removing the ultrasound probe;
aligning a base to support the needle guide on the surface with the one or more primary marks to position the needle guide on the surface;
using the needle guide to guide a needle towards another position on the surface that differs from the position of the imaged target on the surface, wherein the needle guide includes an orientation-setting component to control an angle at which the needle is guided towards the other position; and
measuring an orientation of the surface marking guide in space using a sensor, wherein the surface marking guide comprises the sensor;
wherein the orientation of the surface marking guide and an orientation of the needle guide are used to position the needle guide to have the same orientation as the surface marking guide.

12. The method according to claim 11, comprising using a second marking guide to make one or more secondary marks on the surface at a predetermined position relative to said one or more primary marks, the step of aligning the base comprising aligning the base of the needle guide with one or more of the primary and/or secondary marks.

13. The method according to claim 11, comprising using a chart or software associated with the ultrasound probe to indicate a required needle insertion angle and needle insertion length to reach the internal target, the internal target being at a specific depth on the center line of the ultrasound probe.

14. The method according to claim 13, wherein the chart or software indicates the required needle insertion angle and needle insertion length taking account of needle insertion points at different off-sets from the ultrasound probe center line.

15. The method according to claim 11, wherein the method uses a needle guide system.

16. A needle guide system for use with an ultrasound probe, the needle guide system comprising:
(i) a surface marking guide; and
(ii) a needle guide;
(i) the surface marking guide including:
(a) an attachment portion for removably attaching the surface marking guide onto an end of the ultrasound probe, the end of the ultrasound probe being adapted for holding against a surface; and
(b) either
(A) means for marking the surface for positioning the needle guide when the ultrasound probe is held against the surface; or
(B) means for identifying to a user where to mark a surface for positioning the needle guide when the ultrasound probe is held against the surface; and
(ii) the needle guide including:
(a) a base to support the needle guide on the surface;
(b) one or more alignment features on the base for aligning the base with the mark made on the surface using the one or more marking features of the surface marking guide;
(c) a sensor for measuring an orientation of the surface marking guide in space, wherein the needle guide comprises a corresponding sensor for measuring the orientation of the needle guide, and wherein the needle guide is subsequently positioned to have the same orientation as the surface marking guide; and
(d) a needle support mounted on the base and having a needle channel through which movement of a needle is supported, wherein the needle support includes an orientation-setting component configured to:
support, when the orientation setting component is in a first state, user manipulation across one or more particular degrees of freedom that changes an orientation of the needle channel relative to the base; and
fix, when the orientation setting component is in a second state, the orientation of the needle channel relative to the base and to thus remove the one or more particular degrees of freedom.

17. The needle guide system according to claim 16, wherein the means for identifying to a user where to mark the surface for positioning the needle guide comprise an optical device that projects one or more marking features onto the surface for identifying to the user where to mark the surface for positioning the needle guide.

18. The needle guide system according to claim 16, wherein the means for marking the surface for positioning the needle guide comprises a support foot that is configured to adhere to the surface and to be separated from the surface marking guide to facilitate the means for marking the surface to remain on the surface; and
wherein said one or more alignment features on the base of the needle guide include features that facilitate engagement between the needle guide and the support foot.

19. The needle guide system according to claim 18, wherein the attachment portion for attaching the surface marking guide to the ultrasound probe and the base to support the needle guide on the surface are the same component.

20. The needle guide system according to claim 16, wherein the sensor is mounted on the attachment portion for attaching the surface marking guide to an ultrasound probe and wherein the attachment portion for attaching the surface marking guide to an ultrasound probe and the base to support the needle guide on the surface are the same component.

* * * * *